US006369069B1

(12) United States Patent
Kleemann et al.

(10) Patent No.: US 6,369,069 B1
(45) Date of Patent: Apr. 9, 2002

(54) BIPHENYLSULFONYL CYANAMIDES, METHOD FOR THE PRODUCTION THEREOF AND THEIR UTILIZATION AS A MEDICAMENT

(75) Inventors: Heinz-Werner Kleemann, Bischofsheim; Hans-Jochen Lang, Hofheim; Jan-Robert Schwark, Kelkheim; Andreas Weichert, Egelsbach; Sabine Faber, Idstein; Hans-Willi Jansen, Niedernhausen; Stefan Petry, Frankfurt, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/601,630

(22) PCT Filed: Feb. 4, 1999

(86) PCT No.: PCT/EP99/00724

§ 371 Date: Aug. 4, 2000

§ 102(e) Date: Aug. 4, 2000

(87) PCT Pub. No.: WO99/40064

PCT Pub. Date: Aug. 12, 1999

(30) Foreign Application Priority Data

Feb. 4, 1998 (DE) ........................................ 198 04 251

(51) Int. Cl.[7] ..................... A61K 31/435; C07D 215/02; C07D 263/30; C07D 307/02; C07D 253/02
(52) U.S. Cl. ...................... 514/277; 514/314; 514/374; 514/422; 514/423; 514/395; 514/445; 546/166; 546/251; 548/235; 548/453; 548/579; 548/491; 549/496; 558/392; 564/86
(58) Field of Search ............................ 564/86; 514/603, 514/445, 395, 277, 422, 423, 374, 314; 549/65, 66, 77, 496; 548/235, 453, 579, 491; 546/251, 166; 558/392

(56) References Cited

U.S. PATENT DOCUMENTS 5,807,878 A * 9/1998 Corbier et al. ............... 514/385
5,968,978 A 10/1999 Kleemann et al.

FOREIGN PATENT DOCUMENTS

EP 0 855 392 7/1998
EP 0 903 339 3/1999

OTHER PUBLICATIONS

Derwent Abstract of EP 0 855 392.
Derwent Abstract of EP 0 903 339.
Miller et al., "Stoichiometric Synthesis of Unsymmetrical Mononitrobiphenyls via the Palladium–Catalyzed Cross–Coupling of Arylboronic Acids with Aryl Bromides," Organometallics, vol. 3, pp. 1261–1263 (1984).
Miyaura et al., "The Palladium–Catalyzed Cross–Coupling Reaction of Phenylboronic Acid with Haloarenes in the Presence of Bases," Synthetic Communications, vol. 11, pp. 513–519 (1981).
Jendralla et al., "Efficient, Simple Procedures for the Large–Scale Preparation of Building Blocks for Angiotensin (II) Receptor Antagonists," Liebigs Ann., pp. 1253–1257 (1995).
Lane, "Sodium Cyanoborohydride—A Highly Selective Reducing Agent for Organic Functional Groups," Synthesis, pp. 135–146 (Mar. 1975).
Fruchtel et al., "Organic Chemistry on Solid Supports," Agnew Chem. Int.'l. Ed. Engl., vol. 35, pp. 17–42 (1996).

* cited by examiner

*Primary Examiner*—Floyd D. Higel
*Assistant Examiner*—Ebenezer Sackey
(74) *Attorney, Agent, or Firm*—Finnegan, Henderson, Farabow, Garrett & Dunner, LLP

(57) ABSTRACT

The invention relates to compounds of the formula (I),

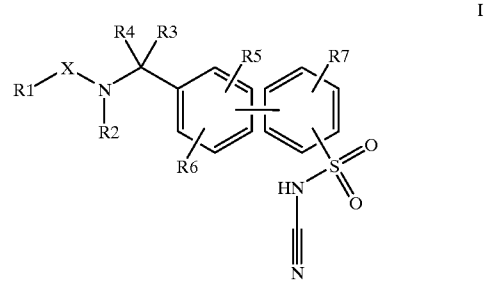

in which the symbols have the following meaning:
R(1) is
1. alkyl having 1, 2, 3, 4, 5, 6, 7 or 8 carbon atoms;
2. alkyl having 1, 2, 3, 4, 5, 6, 7 or 8 carbon atoms, in which one to all hydrogen atoms are replaced by fluorine;
3. alkenyl having 2, 3, 4, 5, 6, 7, 8, 9, 10, 11 or 12 carbon atoms; or
4. —$C_nH_{2n-nn}$—Y,
   nn is zero or 2; and
   n is zero, 1, 2, 3 or 4; where n is unequal to zero or 1 if nn is equal to 2;
5. —$C_nH_{2n-nn}$—Y,
   nn is zero or 2; and
   n is 1, 2, 3 or 4; where n is unequal to 1 if nn is equal to 2.

29 Claims, No Drawings

BIPHENYLSULFONYL CYANAMIDES, METHOD FOR THE PRODUCTION THEREOF AND THEIR UTILIZATION AS A MEDICAMENT

This application is a 371 of PCT/EP 99/0074 filed on Feb. 4, 1999.

The invention relates to compounds of the formula (I), in which the symbols have the following meaning:

R(1) is
1. alkyl having 1, 2, 3, 4, 5, 6, 7 or 8 carbon atoms;
2. alkyl having 1, 2, 3, 4, 5, 6, 7 or 8 carbon atoms, in which one to all hydrogen atoms are replaced by fluorine;
3. alkenyl having 2, 3, 4, 5, 6, 7, 8, 9, 10, 11 or 12 carbon atoms; or
4. —$C_nH_{2n-nn}$—Y,
   nn is zero or 2; and
   n is zero, 1, 2, 3 or 4; where n is unequal to zero or 1 if nn is equal to 2;
5. —$C_nH_{2n-nn}$—Y,
   nn is zero or 2; and
   n is 1, 2, 3 or 4; where n is unequal to 1 if nn is equal to 2;
   where 1, 2 or 3 hydrogen atoms in the divalent radical —$C_nH_{2n-nn}$— independently of one another are replaced by a radical from the group consisting of
     1. aryl having 6, 7, 8, 9, 10, 11, 12, 13 or 14 carbon atoms, preferably phenyl, 1-naphthyl or 2-naphthyl;
     2. amino;
     3. N(R(22)R(23);
     4. alkoxycarbonyl;
     5. COOR(16);
     6. alkyl having 1, 2, 3 or 4 carbon atoms;
     7. ($C_6$–$C_{14}$)-aryl-($C_1$–$C_4$)-alkylcarbonyl, preferably phenylacetyl;

R(2) is
1. hydrogen;
2. alkyl having 1, 2, 3, 4, 5, 6, 7 or 8 carbon atoms;
3. alkyl having 1, 2, 3, 4, 5, 6, 7 or 8 carbon atoms, in which one to all hydrogen atoms are replaced by fluorine;
4. alkenyl having 2, 3, 4, 5, 6, 7, 8, 9, 10, 11 or 12 carbon atoms;
5. alkynyl having 2, 3, 4, 5, 6, 7 or 8 carbon atoms;
6. —$C_nH_{2n-nn}$—Z,
   nn is zero or 2; and
   n is zero, 1, 2, 3 or 4; where n is unequal to zero or 1 if nn is equal to 2;
7. —$C_nH_{2n-nn}$—Z,
   nn is zero or 2; and
   n is 1, 2, 3 or 4, where n is unequal to 1 if nn is equal to 2;
   where 1, 2 or 3 hydrogen atoms in the divalent radical —$C_nH_{2n-nn}$— independently of one another are replaced by a radical from the group consisting of
     1. aryl having 6, 7, 8, 9, 10, 11, 12, 13 or 14 carbon atoms, preferably phenyl, 1-naphthyl or 2-naphthyl;
     2. amino;
     3. N(R(22)R(23);
     4. ($C_1$–$C_4$)-alkoxycarbonyl;
     5. COOR(16);
     6. alkyl having 1, 2, 3 or 4 carbon atoms;

R(3) and R(4) independently of one another are hydrogen or alkyl having 1, 2, 3, 4, 5, 6, 7 or 8 carbon atoms;

R(5), R(6) and R(7) independently of one another are hydrogen, alkyl having 1, 2, 3, 4, 5, 6, 7 or 8 carbon atoms, F, Cl, Br, I, $CF_3$, —CN, —$NO_2$, $SO_q$—R(8), CO—R(21) or O—R(10);

R(8) is alkyl having 1, 2, 3, 4, 5, 6, 7 or 8 carbon atoms, NR(11)R(12) or phenyl which is unsubstituted or is substituted by 1, 2 or 3 identical or different radicals from the group consisting of F, Cl, Br, I, $CF_3$, methyl, methoxy, hydroxyl or NR(11)R(12);

R(9) and R(21) independently of one another are hydrogen, alkyl having 1, 2, 3, 4, 5, 6, 7 or 8 carbon atoms or OR(13);

R(10) is hydrogen, alkyl having 1, 2, 3, 4, 5, 6, 7 or 8 carbon atoms optionally substituted by ($C_1$–$C_4$)-alkoxy; or phenyl which is unsubstituted or is substituted by 1, 2 or 3 identical or different radicals from the group consisting of F, Cl, Br, I, $CF_3$, methyl, methoxy, hydroxyl or NR(11)R(12);

R(11), R(12), R(19) and R(20) independently of one another are hydrogen, alkyl having 1, 2, 3 or 4 carbon atoms or ($C_1$–$C_4$)-alkanoyl, preferably acetyl;

R(13) is hydrogen or alkyl having 1, 2, 3, 4, 5, 6, 7 or 8 carbon atoms;

X is carbonyl, —CO—NH—, —CO—CO— or sulfonyl;

Y and Z independently of one another are
1. aryl having 6, 7, 8, 9, 10, 11, 12, 13 or 14 carbon atoms, preferably phenyl, 1-naphthyl or 2-naphthyl;
2. a radical as defined in 1., which is substituted by 1, 2, 3, 4 or 5 identical or different radicals from the group consisting of alkyl having 1, 2, 3, 4, 5, 6, 7 or 8 carbon atoms, aryl having 6, 7, 8, 9, 10, 11, 12, 13 or 14 carbon atoms, preferably phenyl, 1-naphthyl or 2-naphthyl, F, Cl, Br, I, $CF_3$, $SO_q$R(18), OR(16), NR(19)R(20), —CN, $NO_2$ or CO—R(9); or where two radicals together form a fused heterocyclyl radical, preferably methylenedioxy.
3. heteroaryl having 1, 2, 3, 4, 5, 6, 7, 8 or 9 carbon atoms;
4. a radical as defined in 3., which is substituted by 1, 2 or 3 identical or different radicals from the group consisting of F, Cl, Br, I, $CF_3$, $CH_3$, methoxy, hydroxyl or NR(11)R(12);
5. cycloalkyl having 3, 4, 5, 6, 7, 8, 9 or 10 carbon atoms, preferably cyclopropyl, cyclopentyl, cyclohexyl. 1,2,3,4-tetrahydronaphthyl or indanyl;
6. a radical as defined in 5, substituted by aryl having 6, 7, 8, 9, 10, 11, 12, 13 or 14 carbon atoms, preferably phenyl, 1-naphthyl or 2-naphthyl;
7. O—R(14);
8. O—R(17);

9. —SO$_2$—R(14);
10. arylalkylcarbonyl, preferably phenyl-CH$_2$—CO—; or
11. heterocyclyl;

R(14) and R(17) independently of one another are
1. hydrogen;
2. alkyl having 1, 2, 3, 4, 5, 6, 7 or 8 carbon atoms;
3. alkenyl having 2, 3, 4, 5, 6, 7, 8, 9, 10, 11 or 12 carbon atoms;
4. —C$_n$H$_{2n-nn}$-phenyl,
   nn is zero or 2; and
   n is zero, 1, 2, 3 or 4; where n is unequal to zero or 1 if nn is equal to 2;
5. a radical as defined in 4., where the phenyl moiety is substituted by 1, 2 or 3 identical or different radicals from the group consisting of alkyl having 1, 2, 3, 4, 5, 6, 7 or 8 carbon atoms, F, Cl, Br, I, CF$_3$, SO$_q$R(15), OR(16), NR(11)R(12), —CN, —NO$_2$ or CO—R(9); or R(15) and R(18) independently of one another are alkyl having 1, 2, 3 or 4 carbon atoms, alkyl having 1, 2, 3 or 4 carbon atoms, in which one to all hydrogen atoms are replaced by fluorine, preferably CF$_3$, or NR(11)R(12);

R(16) is
1. hydrogen,
2. alkyl having 1, 2, 3 or 4 carbon atoms,
3. alkyl having 1, 2, 3 or 4 carbon atoms, substituted by (C$_1$–C$_4$)-alkoxy,
4. alkyl having 1, 2, 3 or 4 carbon atoms, in which one to all hydrogen atoms are replaced by fluorine, preferably CF$_3$;
5. aryl having 6, 7, 8, 9, 10, 11, 12, 13 or 14 carbon atoms, preferably phenyl, 1-naphthyl or 2-naphthyl;
6. a radical as defined in 5., which is substituted by 1, 2 or 3 identical or different radicals from the group consisting of F, Cl, Br, I, CF$_3$, NR(19)R(20), —CN, NO$_2$;

R(22) and R(23) independently of one another are hydrogen or CO—OR(24);

R(24) is hydrogen, alkyl having 1, 2, 3, 4, 5, 6, 7 or 8 carbon atoms or —C$_n$H$_{2n}$-phenyl where n is equal to 1, 2, 3 or 4;

q independently of one another is zero, 1 or 2;

and their physiologically tolerable salts.

Preferred compounds of the formula (I) are those where R(1) is
1. alkyl having 1, 2, 3, 4 or 5 carbon atoms;
2. alkyl having 1, 2, 3, 4 or 5 carbon atoms, in which one to all hydrogen atoms are replaced by fluorine;
3. alkenyl having 2, 3, 4, 5, 6, 7, 8, 9, 10, 11 or 12 carbon atoms; or
4. —C$_n$H$_{2n-nn}$—Y,
   nn is zero or 2; and
   n is zero, 1, 2, 3 or 4; where n is unequal to zero or 1 if nn is equal to 2;
5. —C$_n$H$_{2n-nn}$—Y,
   nn is zero or 2; and
   n is 1, 2, 3 or 4; where n is unequal to 1 if nn is equal to 2;
   where 1, 2 or 3 hydrogen atoms in the divalent radical —C$_n$H$_{2n-nn}$— independently of one another are replaced by a radical from the group consisting of
   1. aryl having 6, 7, 8, 9, 10, 11, 12, 13 or 14 carbon atoms, preferably phenyl, 1-naphthyl or 2-naphthyl;
   2. amino;
   3. NR(22)R(23);
   4. alkoxycarbonyl;
   5. COOR(16);
   6. alkyl having 1, 2, 3 or 4 carbon atoms;
   7. (C$_6$–C$_{14}$)-aryl-(C$_1$–C$_4$)-alkylcarbonyl, preferably phenyl-acetyl;

R(2) is
1. hydrogen;
2. alkyl having 1, 2, 3, 4, 5 or 5 carbon atoms;
3. alkyl having 1, 2, 3, 4, or 5 carbon atoms, in which one to all hydrogen atoms are replaced by fluorine;
4. alkenyl having 2, 3, 4, 5, 6, 7, 8, 9, 10, 11 or 12 carbon atoms;
5. alkynyl having 2, 3, 4, or 5 carbon atoms;
6. —C$_n$H$_{2n-nn}$—Z,
   nn is zero or 2; and
   n is zero, 1, 2, 3 or 4; where n is unequal to zero or 1 if nn is equal to 2;
7. —C$_n$H$_{2n-nn}$—Z,
   nn is zero or 2; and
   n is 1, 2, 3 or 4, where n is unequal to 1 if nn is equal to 2;
   where 1, 2 or 3 hydrogen atoms in the divalent radical —C$_n$H$_{2n-nn}$— independently of one another are replaced by a radical from the group consisting of
   1. aryl having 6, 7, 8, 9, 10, 11, 12, 13 or 14 carbon atoms, preferably phenyl, 1-naphthyl or 2-naphthyl;
   2. amino;
   3. N(R(22)R(23);
   4. (C$_1$–C$_4$)-alkoxycarbonyl;
   5. COOR(16);
   6. alkyl having 1, 2, 3 or 4 carbon atoms;

R(3) and R(4) independently of one another are hydrogen or alkyl having 1, 2, 3 or 4 carbon atoms;

R(5), R(6) and R(7) independently of one another are hydrogen, alkyl having 1, 2, 3 or 4 carbon atoms, F, Cl, Br, CF$_3$, —CN, SO$_q$—R(8), CO—R(21) or O—R(10);

R(8) is alkyl having 1, 2, 3 or 4 carbon atoms, NR(11)R(12) or phenyl which is unsubstituted or is substituted by 1 or 2 identical or different radicals from the group consisting of F, Cl, Br, CF$_3$, methyl, methoxy, hydroxyl or NR(11)R(12);

R(9) and R(21) independently of one another are hydrogen, alkyl having 1, 2, 3 or 4 carbon atoms or OR(13);

R(10) is hydrogen, alkyl having 1, 2, 3 or 4 carbon atoms optionally substituted by (C$_1$–C$_4$)-alkoxy; or phenyl which is unsubstituted or is substituted by 1 or 2 identical or different radicals from the group consisting of F, Cl, Br, CF$_3$, methyl, methoxy, hydroxyl or NR(11)R(12);

R(11), R(12), R(19) and R(20) independently of one another are hydrogen, alkyl having 1, 2, 3 or 4 carbon atoms or (C$_1$–C$_4$)-alkanoyl, preferably acetyl;

R(13) is hydrogen or alkyl having 1, 2, 3 or 4 carbon atoms;

X is carbonyl, —CO—NH—, —CO—CO— or sulfonyl;

Y and Z independently of one another are
1. phenyl, 1-naphthyl or 2-naphthyl;
2. a radical as defined in 1., which is substituted by 1, 2, 3, 4 or 5 identical or different radicals from the group consisting of alkyl having 1, 2, 3 or 4 carbon atoms, phenyl, 1-naphthyl or 2-naphthyl, F, Cl, Br, CF$_3$, SO$_q$R(18), OR(16), NR(19)R(20), —CN or CO—R(9); or where two radicals together form a fused heterocyclyl radical, preferably methylenedioxy;
3. heteroaryl having 1, 2, 3, 4, 5, 6, 7, 8 or 9 carbon atoms;

4. a radical as defined in 3., which is substituted by 1 or 2 identical or different radicals from the group consisting of F, Cl, Br, CF$_3$, CH$_3$, methoxy, hydroxyl or NR(11)R(12);
5. cycloalkyl having 3, 4, 5, 6, 7, 8, 9 or 10 carbon atoms, preferably cyclopropyl, cyclopentyl, cyclohexyl, 1,2,3,4-tetrahydronaphthyl or indanyl;
6. a radical as defined in 5., substituted by phenyl, 1-naphthyl or 2-naphthyl;
7. O—R(14);
8. O—R(17);
9. —SO$_2$—R(14);
10. arylalkylcarbonyl, preferably phenyl-CH$_2$—CO—; or
11. heterocyclyl;

R(14) and R(17) independently of one another are
1. hydrogen;
2. alkyl having 1, 2, 3 or 4 carbon atoms;
3. alkenyl having 2, 3, 4, 5 or 6 carbon atoms;
4. —C$_n$H$_{2n-nn}$-phenyl,
   nn is zero or 2; and
   n is zero, 1, 2, 3 or 4; where n is unequal to zero or 1 if nn is equal to 2;
5. a radical as defined in 4., where the phenyl moiety is substituted by 1, 2 or 3 identical or different radicals from the group consisting of alkyl having 1, 2, 3 or 4 carbon atoms, F, Cl, Br, CF$_3$, SO$_q$R(15), OR(16), NR(11)R(12), —CN, or CO—R(9); or R(15) and R(18) independently of one another are alkyl having 1, 2, 3 or 4 carbon atoms, alkyl having 1, 2, 3 or 4 carbon atoms, in which one to all hydrogen atoms are replaced by fluorine, preferably CF$_3$, or NR(11)(R(12);

R(16) is
1. hydrogen,
2. alkyl having 1, 2, 3 or 4 carbon atoms,
3. alkyl having 1, 2, 3 or 4 carbon atoms substituted by (C$_1$–C$_4$)-alkoxy,
4. alkyl having 1, 2, 3 or 4 carbon atoms, in which one to all hydrogen atoms are replaced by fluorine, preferably CF$_3$;
5. phenyl, 1-naphthyl or 2-naphthyl;
6. a radical as defined in 5., which is substituted by 1, 2 or 3 identical or different radicals from the group consisting of F, Cl, Br, CF$_3$, NR(19)R(20), —CN;

R(22) and R(23) independently of one another are hydrogen or CO—OR(24);
R(24) is hydrogen, alkyl having 1, 2, 3 or 4 carbon atoms or —C$_n$H$_{2n}$-phenyl where n is equal to 1, 2 or 3;
q independently of one another is zero, 1 or 2;
and their physiologically tolerable salts.

Particularly preferred compounds of the formula (I) are those where
R(1) is
1. alkyl having 1, 2, 3, 4 or 5 carbon atoms,
2. alkenyl having 2, 3 or 4 carbon atoms,
3. —C$_n$H$_{2n-nn}$—Y;
   Y is
   1. phenyl;
   2. a radical as defined in 1., which [lacuna] by 1, 2, 3, 4 or 5 identical or different radicals from the group consisting of alkyl having 1, 2, 3 or 4 carbon atoms, F, Cl, Br, cyano, CF$_3$, hydroxyl, NO$_2$, SO$_2$R(18), OR(16), SCF$_3$, NR(19)R(20), CO—R(9);
   3. OR(14), or
   4. SO$_2$—R(14);
   5. 1-naphthyl or 2-naphthyl;
   6. a radical as defined in 5., which is substituted by a radical from the group consisting of alkyl having 1, 2, 3 or 4 carbon atoms, F, Cl, CF$_3$, SO$_2$R(18), OR(16), NR(19)R(20) or CO—R(9);
   7. heteroaryl having 1, 2, 3, 4, 5, 6, 7, 8 or 9 carbon atoms; preferably thienyl, benzothiophenyl, indolyl or furyl;
   8. a radical as defined in 3., which is substituted by a radical from the group consisting of F, Cl, CF$_3$, CH$_3$, methoxy or N(CH$_3$)$_2$;
   9. cycloalkyl having 3, 4, 5, 6 or 7 carbon atoms;
   nn is zero or 2; and
   n is zero, 1, 2, 3 or 4, where n is unequal to zero or 1 if nn is equal to 2;
4. —C$_n$H$_{2n-nn}$—Y,
   Y is
   1. phenyl;
   2. OR(14); or
   3. heteroaryl, preferably thienyl;
   nn is zero or 2; and
   n is 1, 2 or 3, where n is unequal to 1 if nn is equal to 2;
   in which 1, 2 or 3 hydrogen atoms in the divalent radical —C$_n$H$_{2n-nn}$— independently of one another are replaced by a radical from the group consisting of
   1. aryl having 6, 7, 8, 9, 10, 11, 12, 13 or 14 carbon atoms, preferably phenyl, 1-naphthyl or 2-naphthyl; or phenylacetyl;
   2. amino;
   3. NR(22)R(23); or
   4. alkyl having 1, 2, 3 or 4 carbon atoms;

R(2) is
1. hydrogen
2. alkyl having 1, 2, 3, 4 or 5 carbon atoms;
3. alkyl having 1, 2, 3, 4 or 5 carbon atoms, in which one to all hydrogen atoms are replaced by fluorine;
4. alkenyl having 2, 3, 4, 5, 6, 7, 8, 9 or 10 carbon atoms;
5. alkynyl having 2, 3, 4 or 5 carbon atoms
6. —C$_n$H$_{2n-nn}$—Z;
   Z is
   1. phenyl;
   2. a radical as defined in 1., which [lacuna] by 1, 2 or 3 identical or different radicals from the group consisting of alkyl having 1, 2, 3 or 4 carbon atoms, phenyl, F, Cl, Br, CF$_3$, SO$_2$R(18), OR(16), nitro, cyano, NR(19)R(20), CO—R(9), or where two radicals together form a methylene-dioxy radical;
   3. 1-naphthyl, or 2-naphthyl;
   4. a radical as defined in 3., which is substituted by a radical from the group consisting of alkyl having 1, 2, 3 or 4 carbon atoms, F, Cl, CF$_3$, SO$_2$R(18), OR(16), nitro, cyano, NR(19)R(20) or CO—R(9);
   5. heteroaryl having 1, 2, 3, 4, 5, 6, 7, 8 or 9 carbon atoms, preferably benzimadozolyl, pyridyl, thienyl, furyl, tetrahydrofuryl, pyrrolidinyl, pyrrolidine-1-carbonyl-4,5-dihydroisoxazolyl, benzofuranyl, for example 1,3-dihydro-1-oxobenzo[c]furanyl, quinazolinyl; for example 3,4-dihydroquinazolinyl;
   6. a radical as defined in 5., which is substituted by a radical from the group consisting of F, Cl, CF$_3$, CH$_3$, methoxy, hydroxyl or N(CH$_3$)$_2$;

7. cycloalkyl having 3, 4, 5, 6, 7, 8, 9 or 10 carbon atoms; preferably, cyclopropyl, cyclopentyl, cyclohexyl, 1,2,3,4-tetrahydronaphthyl or indanyl;
8. a radical as defined in 7., which is substituted by phenyl; preferably phenylcyclopentyl;
nn is zero or 2; and
n is zero, 1, 2 or 3, where n is unequal to zero or 1 if nn is equal to 2;
7. —$C_nH_{2n-nn}$—Z,
Z is
1. phenyl;
2. a radical as defined in 1., which is substituted by 1, 2 or 3 identical or different radicals from the group consisting of alkyl having 1, 2, 3 or 4 carbon atoms, phenyl, F, Cl, $CF_3$, $SO_2R(18)$, —OR(16), nitro, cyano, NR(19)R(20) or CO—R(9);
nn is zero or 2; and
n is 1, 2 or 3, where n is unequal to 1 if nn is equal to 2;
where 1, 2 or 3 hydrogen atoms in the divalent radical —$C_nH_{2n-nn}$— independently of one another are replaced by a radical from the group consisting of
1. ($C_1$–$C_4$)-alkoxycarbonyl;
2. COOR(16); or
3. alkyl having 1, 2, 3 or 4 carbon atoms;
8. —$C_nH_{2n}$—OR(17);
n is zero, 1, 2 or 3;
R(3) and R(4) are hydrogen or methyl;
R(5), R(6) and R(7) independently of one another are hydrogen, alkyl having 1, 2, 3 or 4 carbon atoms, F, Cl, $CF_3$, CN, $SO_2$—R(8), CO—R(21) or O—R(10);
R(8) is alkyl having 1, 2, 3 or 4 carbon atoms, $N(CH_3)_2$ or phenyl which is unsubstituted or is substituted by a radical from the group consisting of F, Cl, $CF_3$, methyl, methoxy, hydroxyl or $N(CH_3)_2$;
R(9) and R(21) independently of one another are hydrogen, methyl or OR(13);
R(10) is hydrogen, alkyl having 1, 2, 3 or 4 carbon atoms, optionally substituted by ($C_1$–$C_4$)-alkoxy, or phenyl which is unsubstituted or is substituted by a radical from the group consisting of F, Cl, $CF_3$, methyl, methoxy or $N(CH_3)_2$;
R(11) and R(12) independently of one another are hydrogen, alkyl having 1, 2, 3 or 4 carbon atoms or ($C_1$–$C_4$)-alkanoyl, preferably acetyl;
R(13) is hydrogen or alkyl having 1, 2, 3 or 4 carbon atoms;
X is carbonyl, —CO—CO—, —NH—CO— or sulfonyl;
R(14) is
1. hydrogen;
2. alkyl having 1, 2, 3 or 4 carbon atoms;
3. alkenyl having 2, 3, 4, 5 or 6 carbon atoms;
4. —$C_nH_{2n-nn}$-phenyl,
nn is zero or 2; and
n is zero, 1, 2, 3 or 4; where n is unequal to zero or 1 if nn is equal to 2;
5. a radical as defined in 4., where the phenyl moiety is substituted by 1, 2 or 3 identical or different radicals from the group consisting of alkyl having 1, 2, 3 or 4 carbon atoms, F, Cl, Br, $CF_3$, $SO_qR(15)$, OR(16), NR(11)R(12), —CN, or CO—R(9);
R(15) is alkyl having 1, 2, 3 or 4 carbon atoms or $N(CH_3)_2$;
R(16) is
1. hydrogen,
2. alkyl having 1, 2, 3 or 4 carbon atoms,
3. alkyl having 1, 2, 3 or 4 carbon atoms substituted by ($C_1$–$C_4$)-alkoxy,
4. alkyl having 1, 2, 3 or 4 carbon atoms, in which one to all hydrogen atoms are replaced by fluorine, preferably $CF_3$;
5. phenyl, 1-naphthyl or 2-naphthyl;
6. a radical as defined in 5., which is substituted by 1, 2 or 3 identical or different radicals from the group consisting of F, Cl, Br, $CF_3$, NR(19)R(20), —CN;
R(17) is
1. hydrogen;
2. alkyl having 1, 2, 3 or 4 carbon atoms;
3. alkenyl having 2, 3, or 4 carbon atoms;
4. —$C_nH_{2n-nn}$-phenyl,
nn is zero or 2; and
n is zero, 1, 2, 3 or 4; where n is unequal to zero or 1 if nn is equal to 2;
5. a radical as defined in 4., where the phenyl moiety is substituted by a radical from the group consisting of alkyl having 1, 2, 3 or 4 carbon atoms, F, Cl, Br, $CF_3$, $SO_qR(15)$, OR(16), NR(11)R(12), —CN, or CO—R(9); or
R(18) is alkyl having 1, 2, 3 or 4 carbon atoms, alkyl having 1, 2, 3 or 4 carbon atoms, in which one to all hydrogen atoms are replaced by fluorine, preferably $CF_3$, or NR(11)R(12);
R(19) and R(20) independently of one another are hydrogen, alkyl having 1, 2, 3 or 4 carbon atoms or ($C_1$–$C_4$)-alkanoyl, preferably acetyl;
R(22) and R(23) independently of one another are hydrogen or CO—OR(24);
R(24) is hydrogen, alkyl having 1, 2, 3 or 4 carbon atoms or —$C_nH_{2n}$-phenyl where n is equal to 1 or 2;
q independently of one another is zero, 1 or 2;
and their physiologically tolerable salts.

Very particularly preferred compounds of the formula (I) are those where
R(t) is
1. alkyl having 1, 2, 3, 4 or 5 carbon atoms,
2. alkenyl having 2, 3 or 4 carbon atoms,
3. —$C_nH_{2n-nn}$—Y;
Y is
1. phenyl;
2. a radical as defined in 1., which is substituted by 1, 2, 3, 4 or 5 identical or different radicals from the group consisting of alkyl having 1, 2, 3 or 4 carbon atoms, F, Cl, Br, cyano, $CF_3$, hydroxyl, $NO_2$, $SO_2R(18)$, $OCH_3$, $OCF_3$, $SCF_3$, $N(CH_3)_2$, NH—CO—$CH_3$, CO—R(9), phenoxy or phenoxy, mono- or polysubstituted by halogen, preferably Cl or F;
3. OR(14), or
4. $S_2$—R(14);
nn is zero or 2; and
n is zero, 1, 2, 3 or 4, where n is unequal to zero or 1 if nn is equal to 2;
4. —$C_nH_{2n-nn}$—Y,
Y is
1. phenyl;
2. OR(14); or
3. heteroaryl, preferably thienyl;
nn is zero or 2; and
n is 1, 2 or 3, where n is unequal to 1 if nn is equal to 2;
in which 1, 2 or 3 hydrogen atoms in the divalent radical —$C_nH_{2n-nn}$— independently of one another are replaced by a radical from the group consisting of
1. aryl having 6, 7, 8, 9, 10, 11, 12, 13 or 14 carbon atoms, preferably phenyl, 1-naphthyl or 2-naphthyl; or phenylacetyl;
2. amino;
3. NR(22)R(23); or
4. alkyl having 1, 2, 3 or 4 carbon atoms;

5. —$C_nH_{2n}$—Y;
Y is
1. 1-naphthyl or 2-naphthyl;
2. a radical as defined in 1., which is substituted by a radical from the group consisting of alkyl having 1, 2, 3 or 4 carbon atoms, F, Cl, $CF_3$, $SO_2R(18)$, $OCH_3$, $N(CH_3)_2$ or CO—R(9);
3. heteroaryl having 1, 2, 3, 4, 5, 6, 7, 8 or 9 carbon atoms; preferably thienyl, benzothio-phenyl, indolyl or furyl;
4. a radical as defined in 3., which is substituted by a radical from the group consisting of F, Cl, $CF_3$, $CH_3$, methoxy or $N(CH_3)_2$;
5. cycloalkyl having 3, 4, 5, 6 or 7 carbon atoms;
n is zero, 1, 2, 3 or 4;

6. —$C_nH_{2n}$—OR(14);
n is zero 1 or 2;

R(2) is
1. alkyl having 1, 2, 3, 4 or 5 carbon atoms;
2. alkyl having 1, 2, 3, 4 or 5 carbon atoms, in which one to all hydrogen atoms are replaced by fluorine;
3. alkenyl having 2, 3, 4, 5, 6, 7, 8, 9 or 10 carbon atoms;
4. alkynyl having 2, 3, 4 or 5 carbon atoms
5. —$C_nH_{2n-nn}$—Z;
Z is
1. phenyl;
2. a radical as defined in 1., which is substituted by 1, 2 or 3 identical or different radicals from the group consisting of alkyl having 1, 2, 3 or 4 carbon atoms, phenyl, F, Cl, Br, $CF_3$, $SO_2R(18)$, —$OCH_3$, —$O(C_2H_4)OCH_3$, ethoxy, hydroxyl, nitro, cyano, $N(CH_3)_2$, —NH—CO—$CH_3$, CO—R(9), phenoxy or phenoxy, monosubstituted or polysubstituted by halogen, preferably Cl or F; or where two radicals together form a methylenedioxy radical;
nn is zero or 2; and
n is zero, 1, 2 or 3, where n is unequal to zero or 1 if nn is equal to 2;

6. —$C_nH_{2n-nn}$—Z,
Z is
1. phenyl;
2. a radical as defined in 1., which is substituted by 1, 2 or 3 identical or different radicals from the group consisting of alkyl having 1, 2, 3 or 4 carbon atoms, phenyl, F, Cl, $CF_3$, $SO_2R(18)$, —$OCH_3$, —$O(C_2H_4)OCH_3$, ethoxy, hydroxyl, nitro, cyano, $N(CH_3)_2$ or CO—R(9);
nn is zero or 2; and
n is 1, 2 or 3, where n is unequal to 1 if nn is equal to 2;
where 1, 2 or 3 hydrogen atoms in the divalent radical —$C_nH_{2n-nn}$— independently of one another are replaced by a radical from the group consisting of
1. ($C_1$–$C_4$)-alkoxycarbonyl;
2. COOR(16); or
3. alkyl having 1, 2, 3 or 4 carbon atoms;

7. —$C_nH_{2n}$—Z;
Z is
1. 1-naphthyl, or 2-naphthyl;
2. a radical as defined in 1., which is substituted by a radical from the group consisting of alkyl having 1, 2, 3 or 4 carbon atoms, F, Cl, $CF_3$, $SO_2R(18)$, $OCH_3$, —$O(C_2H_4)OCH_3$, ethoxy, hydroxyl, nitro, cyano, $N(CH_3)_2$, —$NHCOCH_3$ or CO—R(9);
3. heteroaryl having 1, 2, 3, 4, 5, 6, 7, 8 or 9 carbon atoms, preferably benzimadozolyl, pyridyl, thienyl, furyl, tetrahydrofuryl, pyrrolidinyl, pyrrolidine-1-carbonyl4,5-dihydroisoxazolyl, benzofuranyl, for example 1,3-dihydro-1-oxobenzo[c]furanyl, quinazolinyl; for example 3,4-dihydroquinazolinyl;
4. a radical as defined in 3., which is substituted by a radical from the group consisting of F, Cl, $CF_3$, $CH_3$, methoxy, hydroxyl or $N(CH_3)_2$;
5. cycloalkyl having 3, 4, 5, 6, 7, 8, 9 or 10 carbon atoms; preferably, cyclopropyl, cyclopentyl, cyclohexyl, 1,2,3,4-tetrahydronaphthyl or indanyl;
6. a radical as defined in 5., which is substituted by phenyl; preferably phenylcyclopentyl;
n is zero, 1, 2 or 3;

8. —$C_nH_{2n}$—OR(17);
n is 2 or 3;
R(3) and R(4) are hydrogen;
R(5), R(6) and R(7) independently of one another are hydrogen, alkyl having 1, 2, 3 or 4 carbon atoms, F, Cl, $CF_3$, $SO_2$—R(8), CO—R(21) or O—R(10);
R(8) is methyl or $N(CH_3)_2$;
R(9) and R(21) independently of one another are hydrogen, methyl or OR(13);
R(10) is hydrogen, methyl or ethyl, optionally substituted by methoxy, or phenyl which is unsubstituted or is substituted by a radical from the group consisting of F, Cl, $CF_3$, methyl, methoxy or $N(CH_3)_2$;
R(13) is hydrogen or alkyl having 1, 2, 3 or 4 carbon atoms;
X is carbonyl, —CO—CO—, —NH—CO— or sulfonyl;
R(14) is
1. hydrogen;
2. methyl or ethyl;
3. alkenyl having 2, 3, 4, 5 or 6 carbon atoms, preferably allyl;
4. —$C_nH_{2n}$-phenyl where n is equal to zero or 1;
5. a radical as defined in 4., where the phenyl moiety is substituted by a radical from the group consisting of alkyl having 1, 2, 3 or 4 carbon atoms, F, Cl, $CF_3$, $SO_2R(15)$, $OCH_3$, $N(CH_3)_2$ or CO—R(9); or
6. alkenyl having 2, 3 or 4 carbon atoms;
R(15) is methyl or $N(CH_3)_2$;
R(16) is hydrogen or alkyl having 1, 2, 3, or 4 carbon atoms, preferably methyl or tert-butyl
R(17) is
1. hydrogen;
2. methyl;
3. —$C_nH_{2n}$-phenyl where n is equal to zero or 1;
4. a radical as defined in 3., where the phenyl moiety is substituted by a radical from the group consisting of alkyl having 1, 2, 3 or 4 carbon atoms, F, Cl, $CF_3$, $SO_2R(15)$, $OCH_3$, $N(CH_3)_2$ or CO—R(9); or
5. alkenyl having 2, 3 or 4 carbon atoms;
R(18) is methyl, $CF_3$, amino or $N(CH_3)_2$;
R(22) and R(23) independently of one another are hydrogen or CO—OR(24);

R(24) is hydrogen, alkyl having 1, 2, 3 or 4 carbon atoms or —$C_nH_{2n}$-phenyl where n is equal to 1 or 2;
and their physiologically tolerable salts.

Preferred compounds are also those of the formula Ia,

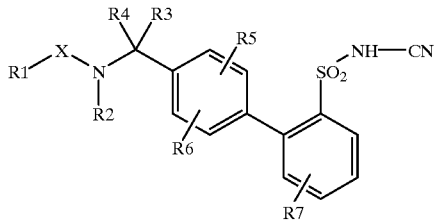

Ia where the radicals X and R(1) to R(7) have the abovementioned meaning, and their physiologically tolerable salts.

Furthermore preferred compounds of the formula I and/or Ia are those in which the radicals X, R(1), R(2), R(3), R(4), R(5), R(6) and R(7) have one of the meaning described in Examples 1–568.

If groups or substituents can occur a number of times in the compounds of the formula I, they can all independently of one another have the meanings indicated and can in each case be identical or different.

Both alkyl, alkenyl and alkynyl can independently of one another be straight-chain or branched. This also applies if they are present in other groups, for example in alkoxy groups, alkoxycarbonyl groups or in amino groups, or if they are substituted.

Examples of alkyl radicals having 1, 2, 3, 4, 5, 6, 7 or 8 carbon atoms are: methyl, ethyl, propyl, butyl, pentyl, hexyl, heptyl, octyl, isopropyl, isobutyl, isopentyl, neopentyl, isohexyl, 3-methylpentyl, sec-butyl, tert-butyl, tert-pentyl.

Examples of alkenyl radicals are vinyl, 1-propenyl, 2-propenyl (allyl), butenyl, 3-methyl-2-butenyl, 2-butenyl, 2-methyl-2-propenyl. The alkenyl radicals can also contain two or more double bonds, such as, for example, butadienyl or $(CH_3)_2C$=CH—$CH_2$—$CH_2$—$C(CH_3)$=CH—$CH_2$—.

Examples of alkynyl radicals are ethynyl, 2-propynyl (propargyl or 3-butynyl. The alkynyl radicals can also contain two or more triple bonds.

Cycloalkyl includes saturated and partially unsaturated cycloalkyl radicals, which can be mono-, bi- or alternatively tricyclic. Examples of such cycloalkyl radicals are cyclopropyl, cyclobutyl, cyclopentyl, cyclohexyl, cycloheptyl, 1,2,3,4-tetrahydronaphthalene and indanyl, which can all be substituted, for example, by one or more identical or different ($C_1$–$C_4$)-alkyl radicals, in particular by methyl. Examples of such substituted cycloalkyl radicals are 4-methylcyclohexyl, 4-tert-butylcyclohexyl or 2,3-dimethyl-cyclopentyl.

Aryl groups having 6, 7, 8, 9, 10, 11, 12, 13 or 14 carbon atoms are, for example, phenyl, naphthyl, biphenyl, antryl or fluorenyl, where 1-naphthyl, 2-naphthyl and in particular phenyl are preferred.

Heteroaryl radicals and heterocyclyl radicals are preferably derived from heterocycles which contain one, two, three or four identical or different ring heteroatoms, particularly preferably from heterocycles which contain one or two or three, in particular one or two, identical or different heteroatoms. If not stated otherwise, the heterocycles can be monocyclic or polycyclic, for example monocyclic, bicyclic or tricyclic. They are preferably monocyclic or bicyclic. The rings are preferably 5-membered rings, 6-membered rings or 7-membered rings. Examples of monocyclic and bicyclic heterocyclic systems, from which radicals occurring in the compounds of the formula I can be derived, are pyrrole, furan, thiophene, imidazole, pyrazole, 1,2,3-triazole, 1,2,4-triazole, 1,3-dioxole, 1,3-oxazole, 1,2-oxazole, 1,3-thiazole, 1,2-thiazole, tetrazole, pyridine, pyridazine, pyrimidine, pyrazine, pyran, thiopyran, 1,4-dioxin, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzimidazole, quinoline, isoquinoline, cinnoline, quinazoline, quinoxaline, phthalazine, thienothiophenes, 1,8-naphthyridine and other naphthyridines, pteridine, or phenothiazine, all in each case in saturated form (perhydro form) or in partially unsaturated form (for example dihydro form and tetrahydro form) or in maximally unsaturated form, if the forms concerned are known and stable. The possible heterocycles thus also include, for example, the saturated heterocycles pyrrolidine, piperidine, piperazine, morpholine and thiomorpholine. Unsaturated heterocycles can contain, for example, one, two or three double bonds in the ring system. 5-membered rings and 6-membered rings in monocyclic and polycyclic heterocycles can in particular also be aromatic.

The radicals derived from these heterocycles can be bonded via any suitable carbon atom. Nitrogen heterocycles which carry a hydrogen atom or a substituent on a ring nitrogen atom, for example pyrrole, imidazole, pyrrolidine, morpholine, piperazine etc., can also be bonded via a ring nitrogen atom, in particular if the nitrogen heterocycle concerned is bonded to a carbon atom. For example, a thienyl radical can be present as a 2-thienyl radical or a 3-thienyl radical, a furan radical as a 2-furyl radical or 3-furyl radical, a pyridyl radical as a 2-pyridyl radical, 3-pyridyl radical or 4-pyridyl radical, a piperidine radical as a 1-piperidyl radical, 2-piperidyl radical, 3-piperidyl radical or 4-piperidyl radical, a thiomorpholine radical as a 2-thiomorpholinyl radical, 3-thiomorpholinyl radical or 4-thiomorpholinyl radical (=thiomorpholino radical). A radical bonded via a carbon atom which is derived from 1,3-thiazole or from imidazole can be bonded via the 2-position, the 4-position or the 5-position.

If not stated otherwise, the heterocyclic groups can be unsubstituted or can carry one or more, for example one, two, three or four, identical or different substituents. The substituents in heterocycles can be located in any desired positions, for example in a 2-thienyl radical or 2-furyl radical in the 3 position and/or in the 4 position and/or in the 5 position, in a 3-thienyl radical or 3-furyl radical in the 2 position and/or in the 4 position and/or in the 5 position, in a 2-pyridyl radical in the 3 position and/or in the 4 position and/or in the 5 position and/or in the 6 position, in a 3-pyridyl radical in the 2 position and/or in the 4 position and/or in the 5 position and/or in the 6 position, in a 4-pyridyl radical in the 2 position and/or in the 3 position and/or in the 5 position and/or in the 6 position. If not stated otherwise, for example, the substituents indicated in the definition of the group aryl can occur as substituents, in the case of saturated or partially unsaturated heterocycles also the oxo group and the thioxo group as further substituents. Substituents on a heterocycle and substituents on a carbocycle can also form a ring, thus further rings can be fused to a ring system so that, for example, cyclopenta-fused, cyclohexa-fused or benzo-fused rings can be present. Possible substituents on a substitutable nitrogen atom of a heterocycle are in particular, for example, unsubstituted $(C_1-C_5)$-alkyl radicals and aryl-substituted alkyl radicals, aryl radicals, acyl radicals such as CO—$(C_1-C_5)$-alkyl, or sulfonyl radicals such as $SO_2$—$(C_1-C_5)$-alkyl. Suitable nitrogen heterocycles can also be present as N-oxides or as quaternary salts having an anion derived from a physiologically tolerable acid as a counterion. Pyridyl radicals can be present, for example, as pyridine N-oxides.

Heteroaryl is, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl.

The heteroaryl radicals can also be completely or partially hydrogenated. Examples which may be mentioned are pyrrolidine-1-carbonyl-4,5 dihydroisoxazolyl, 1,3-dihydro-1-oxobenzo[c]furanyl or 3,4-dihydro-quinazolinyl.

Phenyl radicals, naphthyl radicals and heterocyclic radicals, for example heteroaryl radicals, can, if not stated otherwise, be unsubstituted or can carry one or more, for example one, two, three or four, identical or different substituents, which can be located in any desired positions. If not stated otherwise, for example, the substituents indicated in the definition of the group aryl can occur in these radicals as substituents. If, for example, phenyl radicals, phenoxy radicals, benzyl radicals or benzyloxy radicals are present as substituents in aryl radicals such as, for example, phenyl radicals and/or in heterocyclic radicals, the benzene ring in these can in turn also be unsubstituted or can be substituted by one or more, for example one, two, three or four, identical or different radicals, for example by radicals from the group consisting of $(C_1-C_4)$-alkyl, halogen, hydroxyl, $(C_1-C_4)$-alkoxy, trifluoromethyl, cyano, hydroxycarbonyl, $((C_1-C_4)$-alkoxy$)$carbonyl, aminocarbonyl, nitro, amino, $(C_1-C_4)$-alkylamino, di-$((C_1-C_4)$-alkyl$)$amino and $((C_1-C_4)$-alkyl$)$carbonylamino.

In monosubstituted phenyl radicals, the substituent can be located in the 2 position, the 3 position or the 4 position, in disubstituted phenyl radicals the substituents can be located in the 2,3 position, 2,4 position, 2,5 position, 2,6 position, 3,4 position or 3,5 position. In trisubstituted phenyl radicals, the substituents can be located in the 2,3,4 position, 2,3,5 position, 2,3,6 position, 2,4,5 position, 2,4,6 position or 3,4,5 position. Tolyl (=methylphenyl) is 2-tolyl, 3-tolyl or 4-tolyl. Naphthyl can be 1-napthyl or 2-naphthyl. In monosubstituted 1-naphthyl radicals, the substituent can be located in the 2 position, the 3 position, the 4 position, the 5 position, the 6 position, the 7 position or the 8 position, in monosubstituted 2 naphthyl radicals in the 1 position, the 3 position, the 4 position, the 5 position, the 6 position, the 7 position or the 8 position.

Halogen is fluorine, chlorine, bromine or iodine, preferably fluorine or chlorine.

The present invention includes all stereoisomeric forms of the compounds of the formula I. Asymmetric centers contained in the compounds of the formula I can all independently of one another have the S configuration or the R configuration. The invention includes all possible enantiomers and diastereomers, as well as mixtures of two or more stereoisomeric forms, for example mixtures of enantiomers and/or diastereomers, in all ratios. The invention thus relates to enantiomers in enantiomerically pure form, both as levorotatory and dextrorotatory antipodes, in the form of racemates and in the form of mixtures of the two enantiomers in all ratios. In the presence of cis/trans isomerism, the invention relates both to the cis form and trans form and mixtures of these forms in all ratios. Individual stereoisomers can be prepared, if desired, by resolution of a mixture according to customary methods, for example by chromatography or crystallization, by use of stereochemically uniform starting substances in the synthesis or by stereoselective synthesis. If appropriate, derivatization can be carried out before separation of stereoisomers. A stereoisomer mixture can be separated at the stage of the compounds of the formula I or at the stage of an intermediate in the course of the synthesis. In the presence of mobile hydrogen atoms, the present invention also includes all tautomeric forms of the compounds of the formula I.

If the compounds of the formula I contain one or more acidic or basic groups, the invention also relates to the corresponding physiologically or toxicologically tolerable salts, in particular the pharmaceutically utilizable salts. Thus the compounds of the formula I which contain acidic groups can be present on these groups and used according to the invention as alkali metal salts, alkaline earth metal salts or as ammonium salts. Examples of such salts are sodium salts, potassium salts, calcium salts, magnesium salts or salts with ammonia or organic amines such as, for example, ethylamine, ethanolamine, triethanolamine or amino acids. Compounds of the formula I which contain one or more basic, that is protonatable, groups, can be present and used according to the invention in the form of their acid addition salts with physiologically tolerable inorganic or organic acids, for example as salts with hydrogen chloride, hydrogen bromide, phosphoric acid, sulfuric acid, nitric acid, methanesulfonic acid, p-toluenesulfonic acid, napthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid etc. If the compounds of the formula I simultaneously contain acidic and basic groups in the molecule, the invention also includes internal salts or betaines (zwitterions) in addition to the salt forms described. Salts can be obtained from the compounds of the formula I by customary processes known to the person skilled in the art, for example by combination with an organic or inorganic acid or base in a solvent or dispersant, or alternatively from other salts by anion exchange or cation exchange. The present invention also includes all salts of the compounds of the formula I which are not directly suitable for use in pharmaceuticals because of low physiological tolerability, but are suitable, for example, as intermediates for chemical reactions or for the preparation of physiologically tolerable salts. Physiologically tolerable salts of compounds of the formula (I) are understood as meaning, for example, their organic and inorganic salts, such as are described in Remington's Pharmaceutical Sciences (17th Edition, page 1418 (1985)). On account of the physical and chemical stability and the solubility, sodium, potassium, calcium and ammonium salts, inter alia, are preferred for acidic groups; salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid, inter alia, are preferred for basic groups.

The present invention furthermore includes all solvates of compounds of the formula I, for example hydrates or adducts with alcohols, and also derivatives of the compounds of the formula I such as, for example, esters, and prodrugs and active metabolites.

The invention also relates to processes for the preparation of the novel compounds of the formula (I), and their physiologically tolerable salts.

Thus the compounds of the formula I can be prepared, for example, by means of solid-phase synthesis.

The synthesis is generally carried out here by suitable binding of the benzenesulfonyl structures of the formula (II) via a chemical linker to a polymeric matrix according to the methods of sulfonamide synthesis from sulfonyl chloride and amine known to the person skilled in the art. A suitable polymeric matrix is, for example, polystyrene, polytetrafluoroethylene, polyacrylamide, etc., which can optionally be extended with polyoxyethylene chains (spacers) to improve the swellability. A suitable linker unit is structures which release the synthesized compounds specifically by means of acid, base, reduction, oxidation, by light or using fluoride ions, the linker unit remaining on the polymeric matrix (for a survey of linker groups and polymers in solid-phase synthesis see J. Fruchtel, G. Jung, Angew. Chemie Int. Ed. 1996, 35, 17–42).

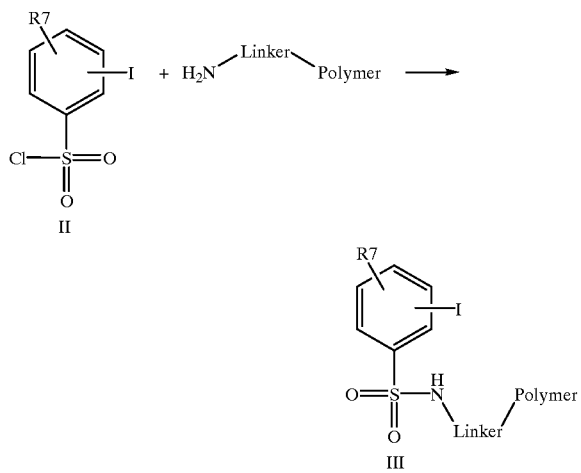

The parent structures of the formula (III) linked to the polymer via the sulfonamide group in this way can be reacted with arylboronic acid 5 derivatives of the formula (IV) to give biphenyl derivatives of the formula (V). For this, the palladium-catalyzed reaction conditions known from the literature are chosen, such as are described, for example, in Organometallics 1984, 3, 1261 or in Synth. Commun. 11 (7), 513 (1981).

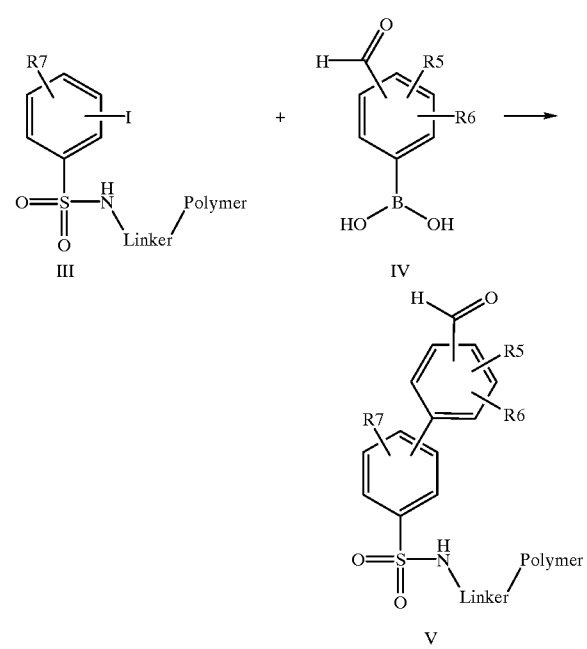

The benzeneboronic acid of the formula (IV) is synthesized, for example, analogously to the synthesis of the 4-formylbenzeneboronic acid, as described in Liebigs Ann. 1995, 1253.

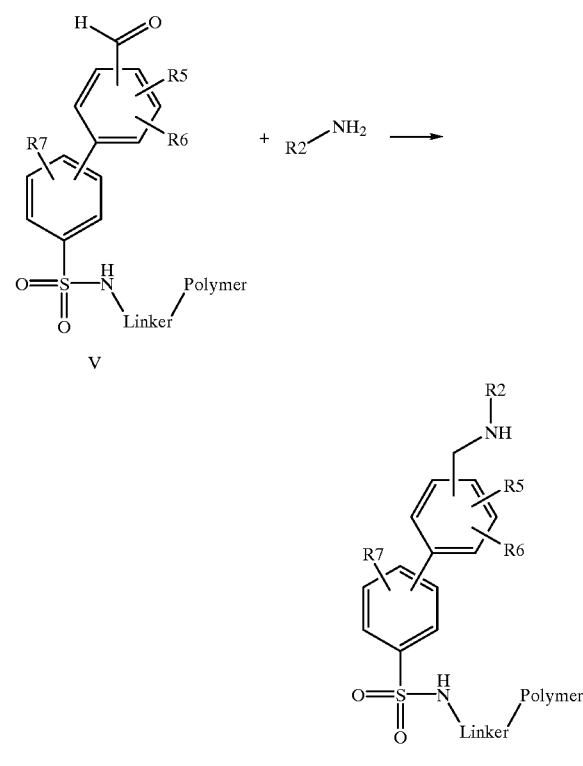

Reductive amination with NaBH₃CN (Review on NaBH₃CN in Synthesis 1975, 135) yields the component (VI), which can be reacted in combination with an acid chloride R¹—X—Cl to give the component of the formula (VII). Synthesis of the solid phase in this case has the advantage that reagents and reactants can be used in a large excess, solvents can be widely varied and purification can be carried out by simple washing of the resin particles.

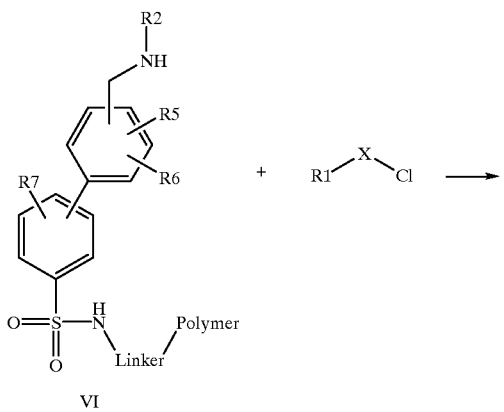

VI

VII

In the case of the radicals R(3), R(4) being unequal to hydrogen, it is necessary to introduce the radicals concerned. This is carried out either by synthesizing the imine of the formula (X), through which the reductive amination proceeds, without reductant from the aldehyde (V) and the appropriate amine and reacting it with an organometallic compound carrying the radical R(3) or the radical R(4) such as, for example, a Grignard compound or an alkyllithium compound in the manner known to the person skilled in the art. Alternatively, the aldehyde function of the compounds of the formula (V) is oxidized to the nitrile of the formula (XI), as is described, for example, in Synthesis 1982, 190 and the radicals R(3) and R(4) are then introduced successively using an organolithium or magnesium compound in a manner known to the person skilled in the art. In the latter case, the radical R(2) must moreover additionally be introduced in the manner known to the person skilled in the art by means of an amine arylation or alkylation.

X

XI

After carrying out the synthesis steps sequentially, the newly synthesized compounds are removed with the aid of specific reagents, according to the choice of linker (for a description of the solid-phase synthesis see: J. Fruchtel. G. Jung, Angew. Chemie Int. Ed. 1996, 35, 17–42). The removal from the resin is carried out as intended for the linker used in a manner known to the person skilled in the art. A suitable preferred polymer is, for example, aminomethylpolystyrene from Fluka (1.1 mmol of amine/g of resin; 2% crosslinked DVB). A preferred suitable linker is, for example, the compound (VIII) known from the literature

VIII (G. Breipohl, J. Knolle, W. Stuber, Int. J. Peptide Protein Res. 34, 1989, 262f). In this case, removal from the resin is carried out under acidic conditions. For this, the compounds of the formula (VII) are treated in an inert solvent, preferably CH₂Cl₂, with an acid having a pKa<5, an acid having a pKa<2 being preferred and trifluoroacetic acid being particularly preferred, and the sulfonamides of the formula (IX) are obtained. A typical reaction time is 5 minutes to 10 hours at a temperature between −30° C. and the boiling point of the solvent, a reaction time between 20 minutes and one hour at room temperature being preferred.

The last synthesis step comprises reacting compounds of the formula (IX)

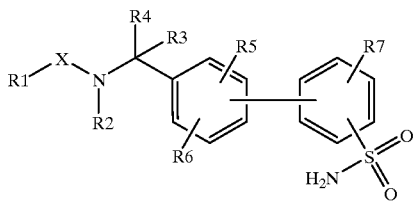

IX in which the radicals are as defined above with cyanogen bromide to give the title compounds of the formula (I). The reaction is carried out in a dipolar aprotic solvent which is stable to cyanogen bromide, for example acetonitrile, DMA, TMU or NMP, using a strong auxiliary base which is not very nucleophilic, such as, for example, $K_2CO_3$ or $Cs_2CO_3$. A suitable reaction temperature is a temperature of between 0° C. and the boiling point of the solvent used, a temperature between 40° C. and 100° C. being preferred.

The compounds of the formula I can also be synthesized by classical synthesis, i.e. in solution, by the methods known to the person skilled in the art.

The compounds of the formula I according to the invention are suitable as inhibitors of the sodium-dependent bicarbonate/chloride exchanger (NCBE) or of the sodium/bicarbonate symporter.

In EP-A 855392, imidazole derivatives having a biphenylsulfonylcyanamide side chain are described as NCBE inhibitors.

In European patent application 98117529.2, biphenylsulfonylcyanamides have been proposed as NCBE inhibitors which differ in the substitution on the biphenyl ring system from the compounds of the formula I.

In addition, the invention relates to the use of a compound of the formula I for the production of a medicament for the treatment or prophylaxis of illnesses caused by ischemic conditions;

and the use of a compound of the formula I for the production of a medicament for the treatment or prophylaxis of cardiac infarct;

and the use of a compound of the formula I for the production of a medicament for the treatment or prophylaxis of angina pectoris;

and the use of a compound for the formula I for the production of a medicament for the treatment or prophylaxis of ischemic conditions of the heart;

and the use of a compound of the formula I for the production of a medicament for the treatment or prophylaxis of ischemic conditions of the peripheral and central nervous system and of stroke;

and the use of a compound of the formula I for the production of a medicament for the treatment or prophylaxis of ischemic conditions of peripheral organs and limbs;

and the use of a compound of the formula I for the production of a medicament for the treatment of states of shock;

and the use of a compound of the formula I for the production of a medicament for use in surgical operations and organ transplantations;

and the use of a compound of the formula I for the production of a medicament for the preservation and storage of transplants for surgical measures;

and the use of a compound of the formula I for the production of a medicament for the treatment of illnesses in which cell proliferation is a primary or secondary cause; and thus its use for the production of an antiatherosclerotic, an agent against diabetic late complications, carcinomatous disorders, fibrotic disorders such as pulmonary fibrosis, liver fibrosis or kidney fibrosis, prostate hyperplasia;

and the use of a compound of the formula I for the production of a medicament for the treatment of impaired respiratory drive;

and a pharmaceutical comprising an efficacious amount of a compound of the formula I.

The compounds of the formula I according to the invention exhibit very good antiarrhythmic properties, such as are important, for example, for the treatment of illnesses which occur in the case of oxygen deficiency symptoms.

On account of their pharmacological properties, the compounds I are outstandingly suitable as antiarrhythmic pharmaceuticals having a cardioprotective component for infarct prophylaxis and infarct treatment and for the treatment of angina pectoris, where they also inhibit or greatly decrease, in a preventive manner, the pathophysiological processes in the formation of ischemically induced damage, in particular in the elicitation of ischemically induced cardiac arrhythmias.

Because of their protective actions against pathological hypoxic and ischemic situations, the compounds of the formula I according to the invention can be used, on account of inhibition of the cellular $Na^+$-dependent $Cl^-/HCO_3^-$ exchange mechanism or of the sodium/bicarbonate symporter as pharmaceuticals for the treatment of all acute or chronic damage caused by ischemia or illnesses induced primarily or secondarily thereby. They protect organs acutely or chronically undersupplied with oxygen by lowering or preventing ischemically induced damage and are thus suitable as pharmaceuticals, for example, in thromboses, vascular spasms, atherosclerosis or in surgical interventions (e.g. in liver and kidney organ transplantations, where the compounds can be used both for the protection of the organs in the donor before and during removal, for the protection of removed organs, for example during treatment with or storage thereof in physiological bath fluids, and during transfer to the recipient's body) or chronic or acute kidney failure.

The compounds of the formula I are also valuable pharmaceuticals having a protective action when carrying out angioplastic surgical interventions, for example on the heart and on peripheral vessels. Corresponding to their protective action against ischemically induced damage, the compounds are also suitable as pharmaceuticals for the treatment of ischemias of the nervous system, in particular of the CNS, where they are suitable, for example, for the treatment of stroke or of cerebral edema. Moreover, the compounds of the formula I according to the invention are also suitable for the treatment of forms of shock, such as, for example, of allergic, cardiogenic, hypovolemic and of bacterial shock.

Moreover, the compounds of the formula I according to the invention are distinguished by strong inhibitory action on the proliferation of cells, for example on fibroblast cell proliferation and on the proliferation of the smooth vascular muscle cells. The compounds of the formula I are therefore suitable as valuable therapeutics for illnesses in which cell proliferation is a primary or secondary cause, and can therefore be used as antiatherosclerotics, agents against diabetic late complications, carcinomatous disorders, fibrotic disorders such as pulmonary fibrosis, liver fibrosis or kidney fibrosis, organ hypertrophies and hyperplasias, in particular in prostate hyperplasia or prostate hypertrophy.

It has been found that inhibitors of the $Na^+$-dependent $Cl^-/HCO_3^-$ exchanger or of the sodium/bicarbonate symporter can stimulate the respiration by means of an increase in the chemosensitivity of the respiratory chemoreceptors. These chemoreceptors are responsible to a considerable extent for the maintenance of an orderly respiratory activity. They are activated in the body by hypoxia, pH decrease and increase in $CO_2$ (hypercapnia) and result in an adjustment of the respiratory minute volume. During sleep, the respiration is particularly susceptible to interference and to a great extent dependent on the activity of the chemoreceptors.

An improvement in the respiratory drive as a result of stimulation of the chemoreceptors with substances which inhibit the $Na^+$-dependent $Cl^-/HCO_3^-$ exchange results in an improvement of the respiration in the following clinical conditions and illnesses: impaired central respiratory drive (e.g. central sleep apnea, sudden infant death, postoperative hypoxia), muscle-related respiratory disorders, respiratory disorders after long-term ventilation, respiratory disorders during adaptation in a high mountain area, obstructive and mixed forms of sleep apneas, acute and chronic lung diseases with hypoxia and hypercapnia.

The compounds of the formula I according to the invention and their physiologically tolerable salts can be used in animals, preferably in mammals, and in particular in man, as pharmaceuticals per se, in mixtures with one another or in the form of pharmaceutical preparations. The present invention also relates to the compounds of the formula I and their physiologically tolerable salts for use as pharmaceuticals, their use in the therapy and prophylaxis of the syndromes mentioned and the production of medicaments therefor. The present invention furthermore relates to pharmaceutical preparations which as active constituent contain an efficacious dose of at least one compound of the formula I and/or of a physiologically tolerable salt thereof in addition to customary pharmaceutically innocuous excipients and auxiliaries. The pharmaceutical preparations normally contain 0.1 to 99 percent by weight, preferably 0.5 to 95 percent by weight, of the compounds of the formula I and/or their physiologically tolerable salts. The pharmaceutical preparations can be prepared in a manner known per se. To this end, the compounds of the formula I and/or their physiologically tolerable salts are brought, together with one or more solid or liquid pharmaceutical vehicles and/or excipients and, if desired, in combination with other pharmaceutical active compounds, into a suitable administration form or dose form, which can then be used as a pharmaceutical in human medicine or veterinary medicine.

Pharmaceuticals which contain a compound of the formula (I) and/or its physiologically tolerable salts can be administered orally, parenterally, intravenously, rectally or by inhalation, the preferred administration being dependent on the particular symptoms of the disorder. The compounds of the formula I can be used here on their own or together with pharmaceutical excipients, namely both in veterinary and in human medicine.

The person skilled in the art is familiar on the basis of his expert knowledge with the excipients which are suitable for the desired pharmaceutical formulation. In addition to solvents, gel-forming agents, suppository bases, tablet excipients and other active compound carriers, it is possible to use, for example, antioxidants, dispersants, emulsifiers, antifoams, flavor corrigents, preservatives, solubilizers or colorants.

For an oral administration form, the active compounds are mixed with the additives suitable therefor, such as vehicles, stabilizers or inert diluents and are brought by means of the customary methods into the suitable administration forms, such as tablets, coated tablets, hard capsules, aqueous, alcoholic or oily solutions. Inert carriers which can be used are, for example, gum arabic, magnesia, magnesium carbonate, potassium phosphate, lactose, glucose or starch, in particular corn starch. Preparation can take place here both as dry and as moist granules. Possible oily vehicles or solvents are, for example, vegetable or animal oils, such as sunflower oil or codliver oil.

For subcutaneous or intravenous administration, the active compounds are brought into solution, suspension or emulsion, if desired with the substances customary therefor such as solubilizers, emulsifiers or other excipients. Suitable solvents, for example, are: water, physiological saline solution or alcohols, e.g. ethanol, propanol, glycerol, and additionally also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of such solvents. If required, the formulation can also contain other pharmaceutical excipients such as surfactants, emulsifiers and stabilizers, and also a propellant. Such a preparation customarily contains the active compound in a concentration from approximately 0.1 to 10, in particular from approximately 0.3 to 3% by weight.

The dose of the active compound of the formula I to be administered and the frequency of administration depend on the potency and duration of action of the compounds used; additionally also on the nature and severity of the illness to be treated and on the sex, age, weight and individual responsiveness of the mammal to be treated. On average, the daily dose of a compound of the formula I in a patient weighing approximately 75 kg is at least 0.001 mg/kg, preferably 0.01 mg/kg, to at most 10 mg/kg, preferably 1 mg/kg, of body weight. In acute episodes of the disease, for example immediately after suffering a cardiac infarct, even higher and, especially, more frequent doses may also be necessary, e.g. up to 4 individual doses per day. In particular on i.v. administration, for example in the case of an infarct patient in the intensive care unit, up to 200 mg per day may be necessary.

The compounds of the formula I can be employed as individual active compounds or in combination with other pharmacologically active compounds.

The compounds of the formula I and/or their physiologically tolerable salts can also be used to achieve an advantageous therapeutic action together with other pharmacologically active compounds for the treatment or prophylaxis of the abovementioned syndromes, in particular for the treatment of cardiovascular disorders. Combination with inhibitors of the sodium/hydrogen exchanger (NHE) and/or with active substances from other classes of cardiovascular active compound is preferred.

The invention additionally relates to the combination of a) NCBE inhibitors of the formula I and/or their physiologically tolerable salts with NHE inhibitors and/or their physiologically tolerable salts; b) NCBE inhibitors of the formula I and/or their physiologically tolerable salts with active substances from other classes of cardiovascular active compound and/or their physiologically tolerable salts and c) of NCBE inhibitors of the formula I and/or their physiologically tolerable salts with NHE inhibitors and/or their physiologically tolerable salts and with active substances from other classes of cardiovascular active compound and/or their physiologically tolerable salts.

The active compounds known and identified as NHE inhibitors are guanidine derivatives, preferably acylguanidines, inter alia as are described in Edward J. Cragoe, Jr., "DIURETICS, Chemistry, Pharmacology and Medicine", J. WILEY & Sons (1983), 303–341 or the NHE inhibitors mentioned in EP98115754.8.

Suitable NHE inhibitors are, for example, also benzoylguanidines, such as are described in U.S. Pat. Nos. 5,292,755, 5,373,024, 5,364,868, 5,591,754, 5,516,805, 5,559,153, 5,571,842, 5,641,792, 5,631,293, EP-A 577024, EP-A 602522, EP-A 602523, EP-A 603650, EP-A 604852, EP-A612723, EP-A627413, EP-A628543, EP-A 640593, EP-A640588, EP-A702001, EP-A 713864, EP-A 723956, EP-A 754680, EP-A 765868, EP-A774459, EP-A794171, EP-A814077, EP-A869116; ortho-substituted benzoylguanidines, such as are described in EP-A 556673, EP-A 791577, EP-A 794172; ortho-amino-substituted benzoylguanidines, such as are described in EP-A 690048; isoquinolines, such as are described in EP-A 590455; benzofused 5-membered ring heterocycles, such as are described in EP-A 639573; diacyl-substituted guanidines, such as are described in EP-A 640587; acylguanidines, such as are described in U.S. Pat. No. 5,547,953; phenyl-substituted alkyl- or alkenylcarbonylguanidines carrying perfluoroalkyl groups, such as are described in U.S. Pat. No. 5,567,734, EP-A 688766; heteroaroylguanidines, such as are described in EP-A 676395; bicyclic heteroaroylguanidines, such as are described in EP-A 682017; indenoylguanidines, such as are described in EP-A 738712; benzyloxycarbonylguanidines, such as are described in EP-A 748795; phenyl-substituted alkenylcarbonylguanidines carrying fluorophenyl groups, such as are described in EP-A 744397; substituted cinnamoylguanidines, such as are described in EP-A 755919; sulfonimidamides, such as are described in EP-A 771788; benzenedicarbonyldiguanidines, such as are described in EP-A 774458, EP-A 774457; diarylcarbonyidiguanidines, such as are described in EP-A 787717; substituted thiophenylalkenylcarbonyl-guanidines, such as are described in EP-A 790245; bis-ortho-substituted benzoylguanidines, such as are described in EP-A 810207; substituted 1- or 2-naphthylguanidines, such as are described in EP-A 810205 and EP-A 810206; indanylidineacetylguanidines, such as are described in EP-A 837055; phenyl-substituted alkenylcarbonylguanidines, such as are described in EP-A 825178; aminopiperidylbenzoylguanidines, such as are described in EP-A 667341; heterocycloxybenzylguanidines, such as are described in EP-A 694537; ortho-substituted benzoylguanidines, such as are described in EP704431; ortho-substituted alkylbenzylguanidines, such as are described in EP-A 699660; ortho-substituted heterocyclylbenzoylguanidines, such as are described in EP-A 699666; ortho-substituted 5-methylsulfonylbenzoylguanidines, such as are described in EP-A 708088; ortho-substituted 5-alkylsulfonylbenzoylguanidines having 4-amino substituents, such as are described in EP-A 723963; ortho-substituted 5-alkylsulfonylbenzoylguanidines having 4-mercapto substituents, such as are described in EP-A 743301; 4-sulfonyl- or 4-sulfinylbenzylguanidines, such as are described in EP-A 758644; alkenylbenzoylguanidines, such as are described in EP-A 760365; benzoylguanidines with fused, cyclic sulfones, such as are described in DE 19548708; benzoyl-, polycyclic aroyl- and heteroaroylguanidines, such as are described in WO 9426709; 3-aryl/heteroarylbenzoylguanidines, such as are described in WO 9604241; 3-phenylbenzoylguanidines having a basic amide in the 5-position, such as are described in WO 9725310; 3-dihalothienyl- or 3-dihalophenyl-benzoylguanidines having a basic substituent in the 5-position, such as are described in WO 9727183; 3-methylsulfonylbenzoylguanidines having specific amino substituents in the 4-position, such as are described in WO 9512584; amiloride derivatives, such as are described in WO 9512592; 3-methylsulfonylbenzoylguanidines having specific amino substituents in the 4-position, such as are described in WO 9726253; indoloylguanidines, such as are described in EP-A 622356 and EP-A 708091; indoloylguanidines having a fused additional ring system, such as are described in EP 787728; methylguanidine derivatives, such as are described in WO 9504052; 1,4-benzoxazinoylguanidines, such as are described in EP-A 719766; 5-bromo-2-naphthoylguanidines, such as are described in JP 8225513; quinoline-4-carbonylguanidines having a phenyl radical in the 2-position, such as are described in EP-A 726254; cinnamoylguanidines, such as are described in JP 09059245; propenoylguanidines having a naphthalene substituent, such as are described in JP 9067332; propenoylguanidines having indole substituents, such as are described in JP 9067340; or heteroaryl-substituted acryloylguanidines, such as are described in WO 9711055, and their physiologically tolerable salts.

Preferred NHE inhibitors are the compounds emphasized as preferred in the publications mentioned. Very particularly preferred compounds are cariporide (HOE642), HOE 694, EMD 96785, FR 168888, FR 183998, SM-20550, KBR-9032, and their physiologically tolerable salts. The most preferred is cariporide or another physiologically tolerable salt of N-(4-isopropyl-3-methanesulfonylbenzoyl) guanidine.

Examples of classes of active compound having cardiovascular activity which can therapeutically be advantageously combined with NCBE inhibitors or can additionally be combined with combinations of NCBE inhibitors and NHE inhibitors are beta-receptor blockers, calcium antagonists, angiotensin-converting enzyme inhibitors, angiotensin receptor blockers, loop diuretics, thiazide diuretics, potassium-sparing diuretics, aldosterone antagonists, such as are employed, for example, in lowering blood pressure, and also cardiac glycosides or other contractile force-increasing agents in the treatment of cardiac insufficiency and of congestive heart failure, as well as antiarrhythmics of the classes I–IV, nitrates, $K_{ATP}$ openers, $K_{ATP}$ blockers, inhibitors of the veratridine-activatable sodium channel, etc. Thus the following, for example, are suitable: the beta-blockers propanolol, atenolol, metoprolol; the calcium antagonists diltiazem hydrochloride, verapamil hydrochloride, nifedipine; the ACE inhibitors captopril, enalapril, ramipril; trandolapril, quinapril, spirapril, preferably ramipril or trandolapril; the angiotensin 11 receptor antagonists losartan, valsartan, telmisartan, eprosartan, tasosartan, candesartan, irbesartan; the loop diuretics furosemide, piretanide, torasemide; the thiazide diuretics hydrochlorothiazide, metolazone, indapamide; the potassium-sparing diuretics amiloride, triamterene, spironolactone; the cardiac glycosides digoxin, digitoxin, strophanthin; the antiarrhythmics amiodarone, sotalol, bretylium, flecainide; the nitrate glyceryl trinitrate; the $K^+$ (ATP) openers cromakalim, lemakalim, nocorandil, pinacidil, minoxidil; the inhibitors of the veratridine-activatable $Na^+$ channel.

Blockers of the noninactivating sodium channel (veratridine-activatable sodium channel) are an example of such a particularly advantageous combination component with NCBE inhibitors of the formula I. The combinations of an NCBE inhibitor with a blocker of the noninactivating sodium channel (veratridine-activatable sodium channel) is suitable for infarct and reinfarct prophylaxis and infarct treatment and also for the treatment of angina pectoris and the inhibition of ischemically induced cardiac arrhythmias, tachycardia and the origin and maintenance of ventricular fibrillation, the combinations of an NCBE inhibitor with a blocker of the noninactivating sodium channel also inhibiting or greatly decreasing, in a preventive manner, the pathophysiological processes in the formation of ischemically induced damage. Because of their increased protective actions against pathological hypoxic and ischemic situations, the novel combinations of an NCBE inhibitor of the formula I with a blocker of the noninactivating sodium channel can be used, as a result of increased inhibition of the $Na^+$ influx into the cell, as pharmaceuticals for the treatment of all acute or chronic damage caused by ischemia or illnesses primarily or secondarily induced thereby. This relates to their use as pharmaceuticals for surgical interventions, e.g. in organ transplantations, where the combinations of an NCBE inhibitor of the formula I with a blocker of the noninactivating sodium channel can be used both for the protection of the organs in the donor before and during removal, for the protection of removed organs, for example even during storage thereof in physiological bath fluids, and during transfer to the recipient's body. The combinations of an NCBE inhibitor of the formula I with a blocker of the noninactivating sodium channel are also valuable pharmaceuticals having a protective action when carrying out angioplastic surgical interventions, for example on the heart and also on peripheral vessels. Corresponding to their protective action against ischemically induced damage, the combinations of an NCBE inhibitor of the formula I with a blocker of the noninactivating sodium channel are also suitable as pharmaceuticals for the treatment of ischemias of the nervous system, in particular of the central nervous system, where they are suitable for the treatment of stroke or of cerebral edema. Moreover, the novel combinations of an NCBE inhibitor of the formula I with a blocker of the noninactivating sodium channel are also suitable for the treatment of forms of shock, such as, for example, of allergic, cardiogenic, hypovolemic and of bacterial shock.

In addition to administration as a fixed combination, the invention also relates to the simultaneous, separate or sequential administration of NCBE inhibitors of the formula I with NHE inhibitors and/or of an additional active substance from another class of cardiovascular active compound for the treatment of the abovementioned illnesses.

The invention additionally relates to a pharmaceutical preparation comprising a) an NCBE inhibitor of the formula I and an NHE inhibitor and/or their physiologically tolerable salts; or b) an NCBE inhibitor of the formula I and additionally an active substance from another class of cardiovascular active compound and/or their physiologically tolerable salts; or c) an NCBE inhibitor of the formula I, an NHE inhibitor and additionally an active substance from another class of cardiovascular active compound, and/or their physiologically tolerable salts.

By means of combined administration, the effect of one combination component can be potentiated by the other respective component, i.e. the action and/or duration of action of a novel combination or preparation is stronger or longer lasting than the action and/or duration of action of the respective individual components (synergistic effect). This leads on combined administration to a reduction of the dose of the respective combination component, compared with individual administration. The novel combinations and preparations accordingly have the advantage that the amounts of active compound to be administered can be significantly reduced and undesired side effects can be eliminated or greatly reduced.

The invention furthermore relates to a commercial pack comprising as pharmaceutical active compound a) an NCBE inhibitor of the formula I and an NHE inhibitor and/or their physiologically tolerable salts; or b) an NCBE inhibitor of the formula I and additionally an active substance from another class of cardiovascular active compound and/or their physiologically tolerable salts; or c) an NCBE inhibitor of the formula I, an NHE inhibitor and additionally an active substance from another class of cardiovascular active compound and/or their physiologically tolerable salts, in each case together with instructions for the use of these active compounds in combination for simultaneous, separate or sequential administration in the treatment or prophylaxis of the abovementioned syndromes, in particular for the treatment of cardiovascular disorders.

The pharmaceutical preparations according to the invention can be prepared, for example, by either intensively mixing the individual components as powders, or by dissolving the individual components in the suitable solvents such as, for example, a lower alcohol and then removing the solvent.

The weight ratio of the NCBE inhibitor to the NHE inhibitor or the substance having cardiovascular activity in the combinations and preparations according to the invention is expediently 1:0.01 to 1:100, preferably 1:0.1 to 1:10.

The combinations and preparations according to the invention in total contain preferably 0.5–99.5% by weight, in particular 4–99% by weight, of these active compounds.

When used according to the invention in mammals, preferably in man, the doses of the various active compound components, for example, vary in the range from 0.001 to 100 mg/kg/day.

List of abbreviations:

| | |
|---|---|
| BCECF | 2'7'-Bis(2-carboxyethyl)-5,6-carboxyfluorescein |
| Bn | Benzyl |
| $CH_2Cl_2$ | Dichloromethane |
| DCI | Desorption-chemical ionization |
| DIP | Diisopropyl ether |
| DMA | Dimethylacetamide |
| DME | Dimethoxyethane |
| DMF | N,N-Dimethylformamide |
| EA | Ethyl acetate (EtOAc) |
| EI | Electron impact |
| eq | equivalent |
| ES | Electrospray ionization |
| ESneg | Electrospray, negative ionization |
| Et | Ethyl |
| EtOH | Ethanol |
| FAB | Fast Atom Bombardment |
| fmoc | 9-Fluorenylmethoxycarbony |
| HEP | n-Heptane |
| HOAc | Acetic acid |
| HOOBT | 3-Hydroxy-1,2,3-benzotriazin-4(3H)-one |
| KOtBu | Potassium t-butoxide |
| Me | Methyl |
| MeOH | Methanol |
| mp | melting point |
| MTB | Methyl tertiary-butyl ether |
| NCBE | Sodium-dependent chloride/bicarbonate exchange |
| NHE | Sodium/hydrogen exchanger |
| NMP | N-Methylpyrrolidone |
| PS | Polystyrene |
| RT | Room temperature |
| THF | Tetrahydrofuran |
| TMU | N,N,N',N'-Tetramethylurea |

| | |
|---|---|
| Tol | Toluene |
| CNS | Central nervous system |

EXAMPLES
General Synthesis Procedure for Solid-phase Synthesis

The synthesis of the compounds of the formula I on solid phase is carried out by suitable bonding of the sulfonamide structures by means of a chemical linker to a polymeric matrix according to methods known to the person skilled in the art. The parent structures linked to the polymer via the sulfonamide group in this way can be subjected to further customary organic reactions of organic chemistry.

In detail, the following steps are passed through (described by way of example for a compound of the formula Ia,

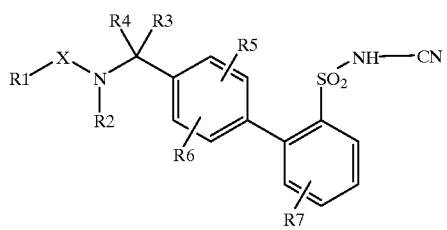

where R(1) is equal to 2-chlorophenyl, R(2) is equal to benzyl, X is equal to carbonyl and R(3) to R(7) are equal to hydrogen.

A. Synthesis of the Linker/polymer Unit

Aminomethylpolystyrene from Fluka was used as a commercially available polymer (1.1 mmol of amine/g of resin; 2% crosslinked DVB). The compound 1 known from the literature was used as a linker (G. Breipohl, J. Knolle, W. Stuber, Int. J. Peptide Protein Res. 34, 1989, 262f).

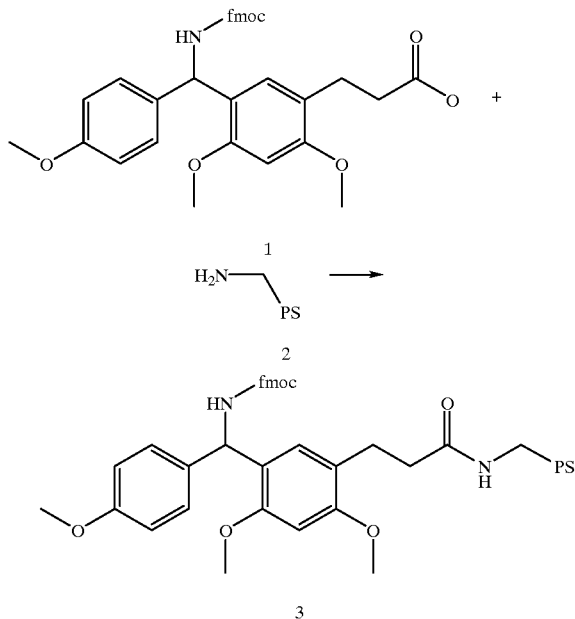

For the linkage of polymer and linker, 14.4 g of aminomethylpolystyrene 2, 28.2 g of 1, 3.2 g of HOOBt, 11.5 g of diisopropylcarbodiimide in 105 ml of DMF and 45 ml of methylene chloride were combined and shaken for 48 h. The resin was then filtered off with suction and thoroughly washed with DMF and MtB.

B. Synthesis of the Resin-bound Sulfonamide 5 g of 3 was treated at RT for 30 min with piperidine/DMF (1:3), the solution was filtered off with suction and the resin was thoroughly washed with DMF. 3.1 g of the compound 4 known from the literature (Gilman, Marker, JACS 74, 1952, 5317) in 20 ml of DMF was added to the DMF-moist resin. After addition of 0.7 ml of pyridine, the mixture was allowed to react at RT for 18 h. The resin was filtered off with suction and washed with DMF and MtB.

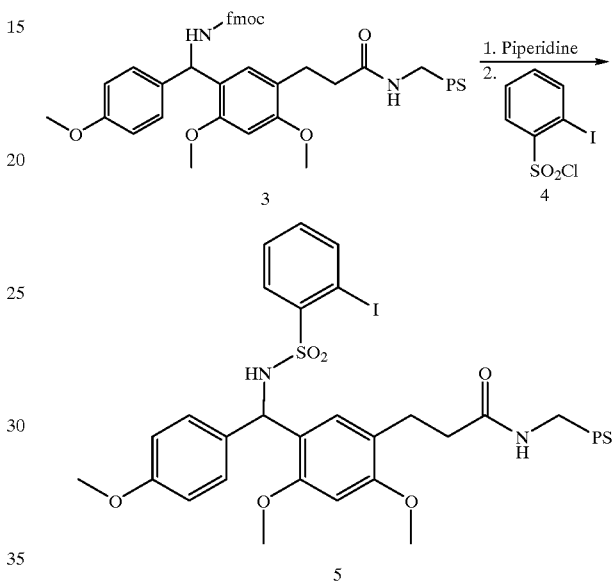

C. Synthesis of the Resin-bound Biarylsulfonamide 7

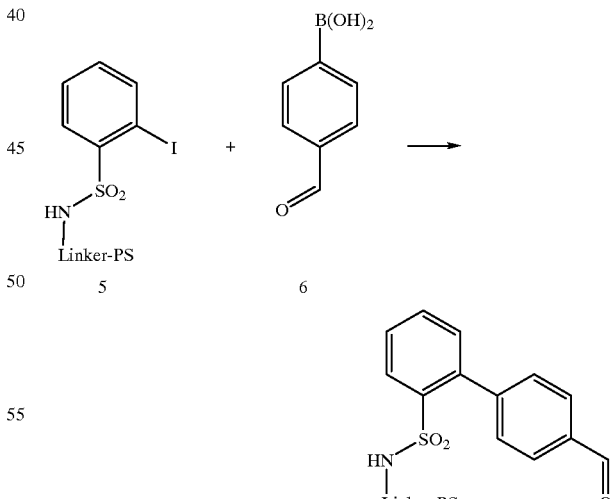

1 g of 5 was swollen in 15 ml of DMF and treated with 1.5 g of the boronic acid 6, 50 mg of Pd(PPh$_3$)$_4$ and 3.5 ml of 2 m Na$_2$CO$_3$ solution. The mixture was allowed to react at 100° C. under an argon atmosphere for 24 h. The resin was filtered off with suction and thoroughly washed with water, DMF and MtB.

D. Reductive Amination on the Solid Phase here: by Way of Example Benzylamine 200 mg of the resin-bound component 7 were treated with 1 mmol of the amine, dissolved in 1 ml of dimethoxyethane/methanol (3:1), and 0.2 ml of a 1 m acetic acid solution in dimethoxyethane and 0.5 ml of a 1 m NaBH$_3$CN solution in dimethoxyethane were added. The mixture was allowed to react at RT for 4 h. The resin was filtered off with suction and thoroughly washed with DMF and MtB.

After removal of a sample (10 mg) from the resin by treatment with 1 ml of methylene chloride/trifluoroacetic acid (3:1), the free amine 8 was characterized by HPLC and MS.

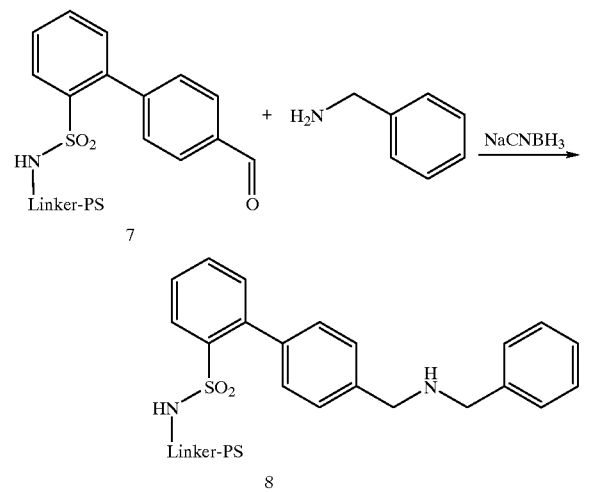

E. N-acylation on the Solid Phase
Here: by way of Example 2-Cl-benzoyl Chloride

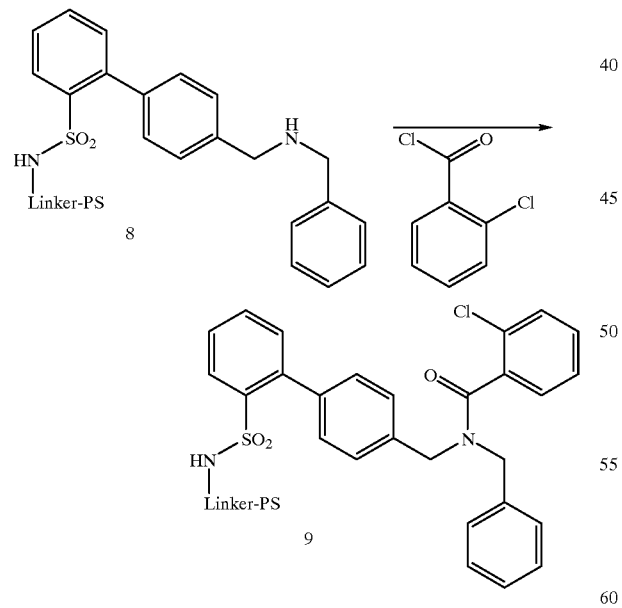

190 mg of 8 were treated with 2 ml of a 1 m solution of N-ethylmorpholine in methylene chloride. The mixture was cooled to 0° C. and 0.5 mmol of the acid chloride, dissolved in 0.5 ml of methylene chloride, was added with stirring. The mixture was allowed to react at 0° C. for 1 h. The resin was filtered off with suction and washed with DMF and MtB. The reaction conversion was checked by means of HPLC and MS by removal of a sample 9 (see D).

F. Removal from the Resin 180 mg of 9 were treated with 3 ml of a solution of methylene chloride/trifluoroacetic acid (3:1) at RT for 30 min. After separation of the solution from the polymer, it was concentrated in vacuo in a rotary evaporator. 30 mg of the free amide 10 were obtained as a residue, which was subjected directly to the cyanylation (G).

G. Synthesis of the Sulfonylcyanamide 30 mg of 10 was dissolved in 3 ml of acetonitrile and treated with 0.3 mmol of triethylamine and also with 0.12 mmol of BrCN in acetonitrile. The mixture was allowed to react at RT for 18 h, then it was treated with 3 ml of MtB and 2 ml of an aqueous buffer solution (pH6). After thorough mixing, the upper phase was removed and applied to silica gel. The silica gel was first washed with 5 ml of MtB, then the product was eluted using 5 ml of EA/HOAc (5:1). After concentration of the solvents in vacuo, 12 mg of the sulfonylcyanamide were obtained in 60–90% purity (by way of example 11.90%). The products thus obtained were further purified by preparative HPLC on RP materials. The products were characterized by HPLC and MS and by way of example by NMR spectroscopy.

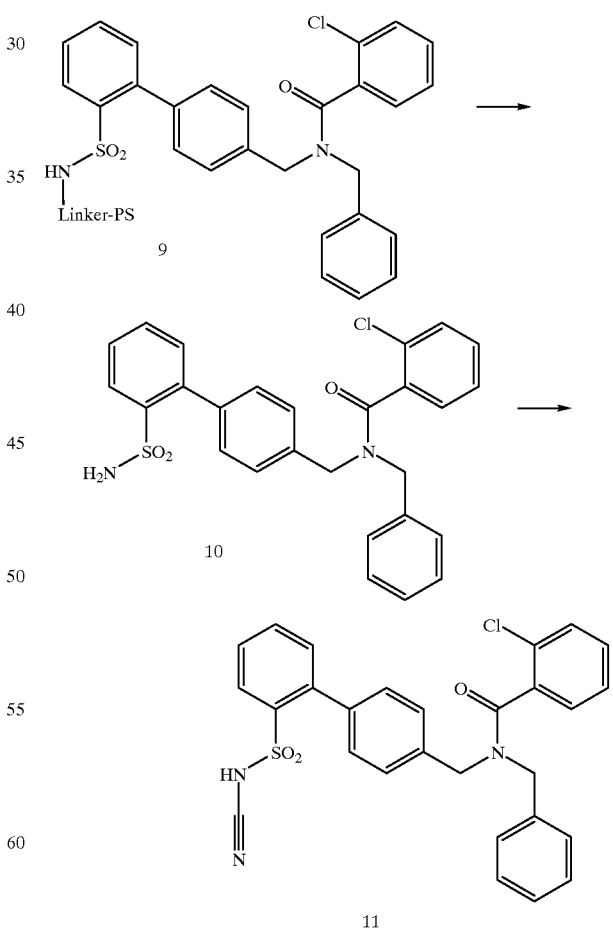

The following compounds of the formula (I) were prepared analogously (R(3) to R(7) is equal to hydrogen).

|  | R(2) | (R1)-X | MS (ES⁻): M-1)⁻ | Residual activity % of the NCBE at 10 μM |
|---|---|---|---|---|
| 1 | -Benzyl | CH3—CH2—CH2—CO— | 446 | |
| 2 | —CH2—CH2—OH | CH3—CH2—CH2—CO— | 400 | 78.1 |
| 3 | 4-Methoxybenzyl- | CH3—CH2—CH2—CO— | 476 | 80.9 |
| 4 | 4-Chlorobenzyl- | CH3—CH2—CH2—CO— | 480 | |
| 5 | -Phenyl | CH3—CH2—CH2—CO— | 431 | 89.5 |
| 6 | -Cyclohexyl | CH3—CH2—CH2—CO— | 438 | 84.5 |
| 7 | -Benzyl | Cyclohexyl-CH2—CH2—CO— | 514 | 33.0 |
| 8 | —CH2—CH2—OH | Cyclohexyl-CH2—CH2—CO— | 468 | 86.7 |
| 9 | 4-Methoxybenzyl- | Cyclohexyl-CH2—CH2—CO— | 544 | 86.6 |
| 10 | 4-Chlorobenzyl- | Cyclohexyl-CH2—CH2—CO— | 548 | 84.9 |
| 11 | -Phenyl | Cyclohexyl-CH2—CH2—CO— | 499 | 68.1 |
| 12 | -Cyclohexyl | Cyclohexyl-CH2—CH2—CO— | 506 | 92.9 |
| 13 | -Benzyl | Cyclohexyl-CO— | 486 | 74.7 |
| 14 | —CH2—CH2—OH | Cyclohexyl-CO— | 440 | 88.7 |
| 15 | 4-Methoxybenzyl- | Cyclohexyl-CO— | 516 | 67.6 |
| 16 | 4-Chlorobenzyl- | Cyclohexyl-CO— | 520 | 56.4 |
| 17 | -Phenyl | Cyclohexyl-CO— | 471 | |
| 18 | -Cyclohexyl | Cyclohexyl-CO— | 478 | |
| 19 | -Benzyl | 3-Methoxyphenyl-CH2—CO— | 524 | 25.9 |
| 20 | —CH2—CH2—OH | 3-Methoxyphenyl-CH2—CO— | 478 | 37.1 |
| 21 | 4-Methoxybenzyl- | 3-Methoxyphenyl-CH2—CO— | 554 | 52.3 |
| 22 | 4-Chlorobenzyl- | 3-Methoxyphenyl-CH2—CO— | 558 | |
| 23 | -Phenyl | 3-Methoxyphenyl-CH2—CO— | 509 | 25.9 |
| 24 | -Cyclohexyl | 3-Methoxyphenyl-CH2—CO— | 516 | 92.1 |
| 25 | -Benzyl | 2-Thienyl-CH2—CO— | 500 | 16.6 |
| 26 | —CH2—CH2—OH | 2-Thienyl-CH2—CO— | 454 | 47.6 |
| 27 | 4-Methoxybenzyl- | 2-Thienyl-CH2—CO— | 530 | 35.5 |
| 28 | 4-Chlorobenzyl- | 2-Thienyl-CH2—CO— | 534 | 95.2 |
| 29 | -Phenyl | 2-Thienyl-CH2—CO— | 485 | 55.7 |
| 30 | -Cyclohexyl | 2-Thienyl-CH2—CO— | 492 | 95.2 |
| 31 | -Benzyl | 4-t-Butylphenyl-CO— | 536 | 52.2 |
| 32 | —CH2—CH2—OH | 4-t-Butylphenyl-CO— | 490 | 68.0 |
| 33 | 4-Methoxybenzyl- | 4-t-Butylphenyl-CO— | 566 | 67.2 |
| 34 | 4-Chlorobenzyl- | 4-t-Butylphenyl-CO— | 570 | |
| 35 | -Phenyl | 4-t-Butylphenyl-CO— | 521 | 53.4 |
| 36 | -Cyclohexyl | 4-t-Butylphenyl-CO— | 528 | |
| 37 | -Benzyl | 2-Fluorophenyl-CO— | 498 | 52.0 |
| 38 | —CH2—CH2—OH | 2-Fluorophenyl-CO— | 452 | 66.7 |
| 39 | 4-Methoxybenzyl- | 2-Fluorophenyl-CO— | 528 | 51.3 |
| 40 | 4-Chlorobenzyl | 2-Fluorophenyl-CO— | 532 | |
| 41 | -Phenyl | 2-Fluorophenyl-CO— | 483 | 94.9 |
| 42 | -Cyclohexyl | 2-Fluorophenyl-CO— | 490 | |
| 43 | -Benzyl | Allyl-O—CO— | 460 | 41.6 |
| 44 | —CH2—CH2—OH | Allyl-O—CO— | 414 | 82.6 |
| 45 | 4-Methoxybenzyl- | Allyl-O—CO— | 490 | 80.1 |
| 46 | 4-Chlorobenzyl- | Allyl-O—CO— | 494 | 52.2 |
| 47 | -Phenyl | Allyl-O—CO— | 445 | 88.1 |
| 48 | -Cyclohexyl | Allyl-O—CO— | 452 | |
| 49 | -Benzyl | 3,4,5-Trimethoxyphenyl-CO— | 570 | 75.8 |
| 50 | —CH2—CH2—OH | 3,4,5-Trimethoxyphenyl-CO— | 524 | |
| 51 | 4-Methoxybenzyl- | 3,4,5-Trimethoxyphenyl-CO— | 600 | |
| 52 | 4-Chlorobenzyl- | 3,4,5-Trimethoxyphenyl-CO— | 604 | 59.9 |
| 53 | -Phenyl | 3,4,5-Trimethoxyphenyl-CO— | 555 | |
| 54 | -Cyclohexyl | 3,4,5-Trimethoxyphenyl-CO— | 562 | |
| 55 | -Benzyl | 2-Chlorophenyl-CO— | 514 | 29.3 |
| 56 | —CH2—CH2—OH | 2-Chlorophenyl-CO— | 468 | 69.0 |
| 57 | 4-Methoxybenzyl- | 2-Chlorophenyl-CO— | 544 | 82.1 |
| 58 | 4-Chlorobenzyl | 2-Chlorophenyl-CO— | 548 | 59.4 |
| 59 | -Phenyl | 2-Chlorophenyl-CO— | 499 | |
| 60 | -Cyclohexyl | 2-Chlorophenyl-CO— | 506 | |

| No. | R2 | R1-X | MS (ES-) (M-1)⁻ | Residual activity (%) of the NCBE at 10 μM |
|---|---|---|---|---|
| 61 | Benzyl- | Phenyl-CO— | 480 | 56.6 |
| 62 | 4-Chlorobenzyl- | CH3—CO— | 452 | 94.5 |
| 63 | Phenyl- | CH3—CO— | 404 | |
| 64 | 4-Methoxybenzyl- | E-CH3—CH=CH—CO— | 474 | 88.0 |
| 65 | 4-Chlorobenzyl- | CH—(CH2)3—CO— | 494 | 80.0 |

-continued

| | | | | |
|---|---|---|---|---|
| 66 | 4-Chlorobenzyl- | Phenyl-CH2—CH2—CO— | 542 | 83.1 |
| 67 | 4-Chlorobenzyl- | E-CH3—CH=CH—CO— | 478 | |
| 68 | 2-Hydroxyethyl- | 4-Methylphenyl-CO— | 448 | 94.4 |
| 69 | 4-Methoxybenzyl- | CH3—CO— | 448 | 95.4 |
| 70 | 4-Methoxybenzyl- | 4-Methylphenyl-CO— | 524 | 94.7 |
| 71 | 2-Chlorobenzyl- | Benzo[b]thiophen-2-yl-CO— | 570 | 35.2 |
| 72 | Isobutyl- | Benzo[b]thiophen-2-yl-CO— | 502 | 86.3 |
| 73 | 1(S)-Phenylethyl- | Benzo[b]thiophen-2-yl-CO— | 550 | 61.0 |
| 74 | 2-Methoxybenzyl- | Benzo[b]thiophen-2-yl-CO— | 566 | 54.7 |
| 75 | 4-Methylbenzyl | Benzo[b]thiophen-2-yl-CO— | 550 | 80.3 |
| 76 | 3-Methoxybenzyl- | Benzo[b]thiophen-2-yl-CO— | 566 | 87.3 |
| 77 | 3,4-Methylenedioxybenzyl- | Benzo[b]thiophen-2-yl-CO— | 580 | 81.8 |
| 78 | 1(R)-Phenylethyl- | Benzo[b]thiophen-2-yl-CO— | 550 | 88.5 |
| 79 | 4-Trifluoromethylbenzyl- | Benzo[b]thiophen-2-yl-CO— | 604 | 61.7 |
| 80 | 2-(4-Methoxyphenyl)ethyl- | Benzo[b]thiophen-2-yl-CO— | 580 | 66.7 |
| 81 | 2-Chlorobenzyl- | Thien-2-yl-CO— | 520 | 36.0 |
| 82 | Isobutyl- | Thien-2-yl-CO— | 452 | 99.8 |
| 83 | 1(S)-Phenylethyl- | Thien-2-yl-CO— | 500 | 97.5 |
| 84 | 2-Methoxybenzyl- | Thien-2-yl-CO— | 516 | 54.7 |
| 85 | 4-Methylbenzyl- | Thien-2-yl-CO— | 500 | 51.1 |
| 86 | 3-Methoxybenzyl | Thien-2-yl-CO— | 516 | 57.0 |
| 87 | 3,4-Methylenedioxybenzyl- | Thien-2-yl-CO— | 530 | 54.8 |
| 88 | 1(R)-Phenylethyl- | Thien-2-yl-CO— | 500 | |
| 89 | 4-Trifluoromethylbenzyl- | Thien-2-yl-CO— | 554 | 67.6 |
| 90 | 2-(4-Methoxyphenyl)ethyl- | Thien-2-yl-CO— | 530 | 84.2 |
| 91 | 2-Chlorobenzyl- | 2-Fluorophenyl-CO— | 532 | 62.7 |
| 92 | Isobutyl- | 2-Fluorophenyl-CO— | 464 | |
| 93 | 1(S)-Phenylethyl- | 2-Fluorophenyl-CO— | 512 | 92.9 |
| 94 | 2-Methoxybenzyl- | 2-Fluorophenyl-CO— | 528 | 87.7 |
| 95 | 4-Methylbenzyl- | 2-Fluorophenyl-CO— | 512 | 74.7 |
| 96 | 3-Methoxybenzyl- | 2-Fluorophenyl-CO— | 528 | |
| 97 | 3,4-Methylenedioxybenzyl- | 2-Fluorophenyl-CO— | 542 | |
| 98 | 1(R)-Phenylethyl- | 2-Fluorophenyl-CO— | 512 | 98.0 |
| 99 | 4-Trifluoromethylbenzyl- | 2-Fluorophenyl-CO— | 566 | 89.6 |
| 100 | 2-(4-Methoxyphenyl)ethyl- | 2-Fluorophenyl-CO— | 542 | 94.1 |
| 101 | 2-Chlorobenzyl- | 2-Chlorophenyl-CO— | 548 | 62.6 |
| 102 | Isobutyl- | 2-Chlorophenyl-CO— | 480 | |
| 103 | 1(S)-Phenylethyl- | 2-Chlorophenyl-CO— | 528 | |
| 104 | 2-Methoxybenzyl- | 2-Chlorophenyl-CO— | 544 | |
| 105 | 4-Methylbenzyl- | 2-Chlorophenyl-CO— | 528 | |
| 106 | 3-Methoxybenzyl- | 2-Chlorophenyl-CO— | 544 | 98.9 |
| 107 | 3,4-Methylenedioxybenzyl- | 2-Chlorophenyl-CO— | 558 | 96.4 |
| 108 | 1(R)-Phenylethyl- | 2-Chlorophenyl-CO— | 528 | 87.7 |
| 109 | 4-Trifluoromethylbenzyl- | 2-Chlorophenyl-CO— | 582 | 75.4 |
| 110 | 2-(4-Methoxyphenyl)ethyl- | 2-Chlorophenyl-CO— | 558 | |
| 111 | 2-Chlorobenzyl- | (Phenyl)2CH—CO— | 604 | 80.5 |
| 112 | Isobutyl- | (Phenyl)2CH—CO— | 536 | 90.4 |
| 113 | 1(S)-Phenylethyl- | (Phenyl)2CH—CO— | 584 | 94.6 |
| 114 | 2-Methoxybenzyl- | (Phenyl)2CH—CO— | 600 | 81.7 |
| 115 | 4-Methylbenzyl- | (Phenyl)2CH—CO— | 584 | 84.0 |
| 116 | 3-Methoxybenzyl- | (Phenyl)2CH—CO— | 600 | |
| 117 | 3,4-Methylenedioxybenzyl- | (Phenyl)2CH—CO— | 614 | |
| 118 | 1(R)-Phenylethyl- | (Phenyl)2CH—CO— | 584 | 95.3 |
| 119 | 4-Trifluoromethylbenzyl- | (Phenyl)2CH—CO— | 638 | 75.7 |
| 120 | 2-(4-Methoxyphenyl)ethyl- | (Phenyl)2CH—CO— | 614 | 81.3 |
| 121 | 2-Chlorobenzyl- | Phenyl-CH2—CO— | 528 | 72.1 |
| 122 | Isobutyl- | Phenyl-CH2—CO— | 460 | 90.6 |
| 123 | 1(S)-Phenylethyl- | Phenyl-CH2—CO— | 508 | 72.2 |
| 124 | 2-Methoxybenzyl- | Phenyl-CH2—CO— | 524 | 46.5 |
| 125 | 4-Methylbenzyl- | Phenyl-CH2—CO— | 508 | 63.6 |
| 126 | 3-Methoxybenzyl- | Phenyl-CH2—CO— | 524 | 53.7 |
| 127 | 3,4-Methylenedioxybenzyl- | Phenyl-CH2—CO— | 538 | 61.7 |
| 128 | 1(R)-Phenylethyl- | Phenyl-CH2—CO— | 508 | 61.4 |
| 129 | 4-Trifluoromethylbenzyl | Phenyl-CH2—CO— | 562 | 47.4 |
| 130 | 2-(4-Methoxyphenyl)ethyl- | Phenyl-CH2—CO— | 538 | 77.8 |
| 131 | 2-Chlorobenzyl- | Phenyl-CH2—CO—CH(phenyl)-CO— | 646 | 97.6 |
| 132 | 1(S)-Phenylethyl- | (2-Thienyl)-CH2—CO— | 514 | 63.8 |
| 133 | 1(R)-Phenylethyl- | (2-Thienyl)-CH2—CO— | 514 | 40.9 |
| 134 | Isobutyl- | Phenyl-CH2—CO—CH(phenyl)-CO— | 578 | |
| 135 | 4-Methylbenzyl- | Phenyl-CH2—CO—CH(phenyl)-CO— | 626 | 97.4 |
| 136 | 1(S)-Phenylethyl- | Phenyl-CH2—CO—CH(phenyl)-CO— | 626 | 93.6 |
| 137 | 1(S)-(4-Methylphenyl)ethyl- | (2-Thienyl)-CH2—CO— | 528 | |
| 138 | 1(R)-(4-Methylphenyl)ethyl- | (2-Thienyl)-CH2—CO— | 528 | |
| 139 | 2-Furylmethyl- | (2-Thienyl)-CH2—CO— | 490 | 48.5 |
| 140 | 4-(Dimethylamino)benzyl- | (2-Thienyl)-CH2—CO— | 543 | 54.2 |

| | | | | |
|---|---|---|---|---|
| 141 | 2-(2-Thienyl)ethyl- | (2-Thienyl)-CH2—CO— | 520 | 71.1 |
| 142 | 2-Phenoxyethyl- | (2-Thienyl)-CH2—CO— | 530 | 27.1 |
| 143 | 2-Chlorobenzyl- | (2-Thienyl)-CH2—CO— | 534 | 35.7 |
| 144 | Cyclopropylmethyl- | (2-Thienyl)-CH2—CO— | 464 | 60.3 |
| 145 | 3,4,5-Trimethoxybenzyl- | (2-Thienyl)-CH2—CO— | 590 | 39.6 |
| 146 | (4-Pyridyl)methyl | (2-Thienyl)-CH2—CO— | 501 | 69.8 |
| 147 | 4-Fluorobenzyl- | (2-Thienyl)-CH2—CO— | 518 | 53.2 |
| 148 | 2-Furylmethyl- | (4-Chlorophenyl)-CH2—CO— | 518 | 45.6 |
| 149 | 4-(Dimethylamino)benzyl- | (4-Chlorophenyl)-CH2—CO— | 571 | 77.4 |
| 150 | 2-(2-Thienyl)ethyl- | (4-Chlorophenyl)-CH2—CO— | 548 | 44.7 |
| 151 | 2-Phenoxyethyl- | (4-Chlorophenyl)-CH2—CO— | 558 | 29.0 |
| 152 | 2-Chlorobenzyl- | (4-Chlorophenyl)-CH2—CO— | 562 | 29.5 |
| 153 | Cyclopropylmethyl- | (4-Chlorophenyl)-CH2—CO— | 492 | 46.1 |
| 154 | 2,4-Dimethoxybenzyl- | (4-Chlorophenyl)-CH2—CO— | 588 | 36.2 |
| 155 | 3,4,5-Trimethoxybenzyl- | (4-Chlorophenyl)-CH2—CO— | 618 | 34.2 |
| 156 | (4-Pyridyl)methyl- | (4-Chlorophenyl)-CH2—CO— | 529 | 86.0 |
| 157 | 4-Fluorobenzyl- | (4-Chlorophenyl)-CH2—CO— | 546 | 24.9 |
| 158 | 2-Furylmethyl | (CH3)3C—CH2—CO— | 464 | 57.9 |
| 159 | 2-(2-Thienyl)ethyl- | (CH3)3C—CH2—CO— | 494 | 61.2 |
| 160 | 2-Phenoxyethyl- | (CH3)3C—CH2—CO— | 504 | 71.6 |
| 161 | Cyclopropylmethyl- | (CH3)3C—CH2—CO— | 438 | 81.6 |
| 162 | 3,4,5-Trimethoxybenzyl- | (CH3)3C—CH2—CO— | 564 | 30.2 |
| 163 | 4-Fluorobenzyl- | (CH3)3C—CH2—CO— | 492 | 93.4 |
| 164 | 2-Furylmethyl- | Phenyl-O—CH2—CO— | 500 | 76.4 |
| 165 | 2-(2-Thienyl)ethyl- | Phenyl-O—CH2—CO— | 530 | 56.8 |
| 166 | 2-Phenoxyethyl- | Phenyl-O—CH2—CO— | 540 | 57.9 |
| 167 | 2-Chlorobenzyl- | Phenyl-O—CH2—CO— | 544 | 47.5 |
| 168 | Cyclopropylmethyl- | Phenyl-O—CH2—CO— | 474 | 96.4 |
| 169 | 3,4,5-Trimethoxybenzyl- | Phenyl-O—CH2—CO— | 600 | |
| 170 | 4-Fluorobenzyl- | Phenyl-O—CH2—CO— | 528 | |
| 171 | 2-Furylmethyl- | (4-Methoxyphenyl)-CH2—CO— | 514 | |
| 172 | 2-(2-Thienyl)ethyl- | (4-Methoxyphenyl)-CH2—CO— | 544 | 89.7 |
| 173 | 2-Phenoxyethyl- | (4-Methoxyphenyl)-CH2—CO— | 554 | 76.4 |
| 174 | 2-Chlorobenzyl- | (4-Methoxyphenyl)-CH2—CO— | 558 | 50.2 |
| 175 | Cyclopropylmethyl- | (4-Methoxyphenyl)-CH2—CO— | 488 | 93.2 |
| 176 | 3,4,5-Trimethoxybenzyl- | (4-Methoxyphenyl)-CH2—CO— | 614 | 83.9 |
| 177 | 4-Fluorobenzyl- | (4-Methoxyphenyl)-CH2—CO— | 542 | 64.4 |
| 178 | 2-Furylmethyl | CH3—CO— | 408 | 70.6 |
| 179 | 2-(2-Thienyl)ethyl- | CH3—CO— | 438 | 78.3 |
| 180 | 2-Phenoxyethyl- | CH3—CO— | 448 | 70.9 |
| 181 | 2-Chlorobenzyl- | CH3—CO— | 452 | 80.8 |
| 182 | Cyclopropylmethyl- | CH3—CO— | 382 | 74.9 |
| 183 | 2,4-Dimethoxybenzyl- | CH3—CO— | 478 | |
| 184 | 3,4,5-Trimethoxybenzyl- | CH3—CO— | 508 | |
| 185 | 4-Fluorobenzyl- | CH3—CO— | 436 | 85.0 |
| 186 | 3-Phenylpropyl- | (2-Thienyl)-CH2—CH2—CH2—CO— | 556 | 9.7 |
| 187 | 2-Methoxyethyl- | (2-Thienyl)-CH2—CH2—CH2—CO— | 496 | 62.4 |
| 188 | (2-Pyridyl)methyl- | (2-Thienyl)-CH2—CH2—CH2—CO— | 529 | 52.3 |
| 189 | Cyclopropyl | (2-Thienyl)-CH2—CH2—CH2—CO— | 478 | 72.5 |
| 190 | Methyl- | (2-Thienyl)-CH2—CH2—CH2—CO— | 452 | 43.4 |
| 191 | Ethyl- | (2-Thienyl)-CH2—CH2—CH2—CO— | 466 | 39.3 |
| 192 | (2-Benzimidazolyl)methyl- | (2-Thienyl)-CH2—CH2—CH2—CO— | 568 | 49.1 |
| 193 | 1-Methoxycarbonyl-2-phenylethyl- | (2-Thienyl)-CH2—CH2—CH2—CO— | 600 | 62.8 |
| 194 | 3-Phenylpropyl- | (2-Thienyl)-CO—CO— | 542 | 61.1 |
| 195 | 2-Methoxyethyl- | (2-Thienyl)-CO—CO— | 482 | 58.3 |
| 196 | (2-Pyridyl)methyl- | (2-Thienyl)-CO—CO— | 515 | 62.8 |
| 197 | Cyclopropyl | (2-Thienyl)-CO—CO— | 464 | 79.9 |
| 198 | Methyl- | (2-Thienyl)-CO—CO— | 438 | 51.1 |
| 199 | Ethyl- | (2-Thienyl)-CO—CO— | 452 | 54.7 |
| 200 | (2-Benzimidazolyl)methyl- | (2-Thienyl)-CO—CO— | 544 | 55.2 |
| 201 | 1-Methoxycarbonyl-2-phenylethyl- | (2-Thienyl)-CO—CO— | 586 | 69.6 |
| 202 | 3-Phenylpropyl- | (Indol-3-yl)-CH2—CO— | 561 | 38.5 |
| 203 | 2-Methoxyethyl- | (Indol-3-yl)-CH2—CO— | 501 | 30.3 |
| 204 | (2-Pyridyl)methyl- | (Indol-3-yl)-CH2—CO— | 534 | 52.4 |
| 205 | Cyclopropyl- | (Indol-3-yl)-CH2—CO— | 483 | 41.7 |
| 206 | Methyl- | (Indol-3-yl)-CH2—CO— | 457 | 23.8 |
| 207 | Ethyl- | (Indol-3-yl)-CH2—CO— | 471 | 31.0 |
| 208 | (2-Benzimidazolyl)methyl- | (Indol-3-yl)-CH2—CO— | 573 | 50.7 |
| 209 | 1-Methoxycarbonyl-2-phenylethyl- | (Indol-3-yl)-CH2—CO— | 605 | 56.2 |
| 210 | 3-Phenylpropyl- | (Benzo[b]thiophen-3-yl)-CH2—CO— | 578 | 66.2 |
| 211 | 2-Methoxyethyl- | (Benzo[b]thiophen-3-yl)-CH2—CO— | 518 | 50.6 |
| 212 | (2-Pyridyl)methyl- | (Benzo[b]thiophen-3-yl)-CH2—CO— | 551 | 60.2 |
| 213 | Cyclopropyl- | (Benzo[b]thiophen-3-yl)-CH2—CO— | 500 | 45.0 |
| 214 | Methyl- | (Benzo[b]thiophen-3-yl)-CH2—CO— | 474 | 44.3 |
| 215 | Ethyl- | (Benzo[b]thiophen-3-yl)-CH2—CO— | 488 | 65.7 |

| | | | | |
|---|---|---|---|---|
| 216 | (2-Benzimidazolyl)methyl- | (Benzo[b]thiophen-3-yl)-CH2—CO— | 590 | 62.2 |
| 217 | 1-Methoxycarbonyl-2-phenylethyl- | (Benzo[b]thiophen-3-yl)-CH2—CO— | 622 | 46.0 |
| 218 | 3-Phenylpropyl | (2-Thienyl)-(CH2)4—CO— | 570 | 87.1 |
| 219 | 2-Methoxyethyl- | (2-Thienyl)-(CH2)4—CO— | 510 | 82.5 |
| 220 | (2-Pyridyl)methyl | (2-Thienyl)-(CH2)4—CO— | 543 | 73.2 |
| 221 | Cyclopropyl- | (2-Thienyl)-(CH2)4—CO— | 492 | 72.3 |
| 222 | Methyl- | (2-Thienyl)-(CH2)4—CO— | 466 | 76.7 |
| 223 | Ethyl- | (2-Thienyl)-(CH2)4—CO— | 480 | 53.8 |
| 224 | (2-Benzimidazolyl)methyl- | (2-Thienyl)-(CH2)4—CO— | 582 | 79.8 |
| 225 | 1-Methoxycarbonyl-2-phenylethyl- | (2-Thienyl)-(CH2)4—CO— | 614 | 88.1 |
| 226 | 3-Phenylpropyl- | (3-Thienyl)-CH2—CO— | 528 | 34.8 |
| 227 | 2-Methoxyethyl- | (3-Thienyl)-CH2—CO— | 468 | 50.6 |
| 228 | (2-Pyridyl)methyl- | (3-Thienyl)-CH2—CO— | 501 | 94.8 |
| 229 | Cyclopropyl- | (3-Thienyl)-CH2—CO— | 450 | 86.7 |
| 230 | Methyl- | (3-Thienyl)-CH2—CO— | 424 | 68.6 |
| 231 | Ethyl- | (3-Thienyl)-CH2—CO— | 438 | 57.8 |
| 232 | (2-Benzimidazolyl)methyl- | (3-Thienyl)-CH2—CO— | 540 | 62.6 |
| 233 | 1-Methoxycarbonyl-2-phenylethyl | (3-Thienyl)-CH2—CO— | 572 | 68.1 |
| 234 | 2-Phenylethyl- | (2-Thienyl)-CH2—CO— | 514 | |
| 235 | 4-Trifluoromethylbenzyl- | (2-Thienyl)-CH2—CO— | 568 | 67.1 |
| 236 | 3-Phenylpropyl | (2-Thienyl)-CH2—CO— | 528 | 35.1 |
| 237 | 2-Methoxyethyl- | (2-Thienyl)-CH2—CO— | 468 | 50.3 |
| 238 | (3,4-Dihydroquinazolin-2-yl)methyl- | (2-Thienyl)-CH2—CO— | 554 | 54.7 |
| 239 | Methyl- | (2-Thienyl)-CH2—CO— | 424 | 56.3 |
| 240 | Ethyl- | (2-Thienyl)-CH2—CO— | 438 | 58.0 |
| 241 | Benzyl- | Phenyl-CH(NH2)—CO— | 509 | 66.0 |
| 242 | Benzyl- | Phenyl-CH(NHCO—O-benzyl)-CO— | 643 | 72.4 |
| 243 | Benzyl- | (2-Nitrophenyl)-CH2—CO— | 539 | 99.9 |
| 244 | Benzyl- | Phenyl-(CH2)4—CO— | 536 | 60.4 |
| 245 | Benzyl- | (2-Furyl)-CO—CO— | 498 | 73.0 |
| 246 | Propargyl- | Phenyl-CH(NHCO—O-benzyl)-CO— | 591 | 65.0 |
| 247 | Propargyl- | Phenyl-(CH2)4—CO— | 484 | 74.6 |
| 248 | Propargyl- | (2-Furyl)-CO—CO— | 446 | 66.6 |
| 249 | Propargyl- | Cyclohexyl-CH2—CH2—CO— | 462 | 76.1 |
| 250 | (2-Thienyl)methyl- | (2-Thienyl)-CH2—CO— | 506 | 41.1 |
| 251 | (2-Thienyl)methyl- | Phenyl-CH(NHCO—O-benzyl)-CO— | 649 | 83.9 |
| 252 | (2-Thienyl)methyl- | (2-Nitrophenyl)-CH2—CO— | 545 | 44.5 |
| 253 | (2-Thienyl)methyl- | Phenyl-(CH2)4—CO— | 542 | 35.3 |
| 254 | (2-Thienyl)methyl- | (2-Furyl)-CO—CO— | 504 | 64.5 |
| 255 | (2-Thienyl)methyl- | Cyclohexyl-CH2—CH2—CO— | 520 | 61.0 |
| 256 | Cyclohexylmethyl- | (2-Thienyl)-CH2—CO— | 506 | 36.4 |
| 257 | Cyclohexylmethyl- | (2-Nitrophenyl)-CH2—CO— | 545 | 54.6 |
| 258 | Cyclohexylmethyl- | (2-Furyl)-CO—CO— | 504 | 95.8 |
| 259 | 3,4-Dichlorobenzyl- | (2-Thienyl)-CH2—CO— | 568 | 40.1 |
| 260 | 3,4-Dichlorobenzyl- | Phenyl-CH(NHCO—O-benzyl)-CO— | 711 | 69.8 |
| 261 | 3,4-Dichlorobenzyl- | (2-Nitrophenyl)-CH2—CO— | 607 | 67.7 |
| 262 | 3,4-Dichlorobenzyl- | Phenyl-(CH2)4—CO— | 604 | 45.3 |
| 263 | 3,4-Dichlorobenzyl- | (2-Furyl)-CO—CO— | 566 | 54.0 |
| 264 | 3,4-Dichlorobenzyl- | Cyclohexyl-CH2—CH2—CO— | 582 | 74.3 |
| 265 | Cyclohexylmethyl- | Phenyl-CH(NHCO—O-benzyl)-CO— | 649 | 68.9 |
| 266 | Cyclohexylmethyl- | Phenyl-(CH2)4—CO— | 542 | 79.7 |
| 267 | Cyclohexylmethyl- | Cyclohexyl-CH2—CH2—CO— | 520 | 57.9 |
| 268 | Phenyl-CH(COOCH3)— | (2-Thienyl)-CH2—CO— | 558 | 79.3 |
| 269 | Phenyl-CH(COOC(CH3)3)— | (2-Thienyl)-CH2—CO— | 600 | 94.4 |
| 270 | 2,4-Dichlorobenzyl- | (2-Thienyl)-CH2—CO— | 568 | 33.9 |
| 271 | (1-Naphthyl)methyl- | (2-Thienyl)-CH2—CO— | 550 | 15.9 |
| 272 | 2-(4-H2NSO2-phenyl)ethyl- | (2-Thienyl)-CH2—CO— | 593 | 65.0 |
| 273 | 3-Chlorobenzyl- | (2-Thienyl)-CH2—CO— | 534 | 32.4 |
| 274 | Phenyl-CH(COOCH3)— | (2-Bromophenyl)-CH2—CO— | 630 | 73.6 |
| 275 | Phenyl-CH(COOC(CH3)3)— | (2-Bromophenyl)-CH2—CO— | 672 | 54.6 |
| 276 | 2,4-Dichlorobenzyl- | (2-Bromophenyl)-CH2—CO— | 640 | 36.8 |
| 277 | (1-Naphthyl)methyl- | (2-Bromophenyl)-CH2—CO— | 622 | 36.3 |
| 278 | 3-Chlorobenzyl- | (2-Bromophenyl)-CH2—CO— | 606 | 31.2 |
| 279 | 2,4-Dichlorobenzyl- | Phenyl-SO2—CH2—CH2—CO— | 640 | 90.5 |
| 280 | (1-Naphthyl)methyl- | Phenyl-SO2—CH2—CH2—CO— | 622 | 63.3 |
| 281 | 3-Chlorobenzyl- | Phenyl-SO2—CH2—CH2—CO— | 606 | 68.6 |
| 282 | Phenyl-CH(COOH)— | (2-Thienyl)-CH2—CO— | 544 | 89.0 |
| 283 | 2,4-Dichlorobenzyl- | (4-Hydroxyphenyl)-CH2—CO— | 578 | 80.0 |
| 284 | (1-Naphthyl)methyl- | (4-Hydroxyphenyl)-CH2—CO— | 560 | 52.9 |
| 285 | 3-Chlorobenzyl- | (4-Hydroxyphenyl)-CH2—CO— | 544 | 58.8 |
| 286 | Phenyl-CH(COOCH3)— | (2-Thienyl)-CH2—CH2—CO— | 572 | 68.8 |
| 287 | Phenyl-CH(COOC(CH3)3)— | (2-Thienyl)-CH2—CH2—CO— | 614 | 51.1 |
| 288 | 2,4-Dichlorobenzyl- | (2-Thienyl)-CH2—CH2—CO— | 582 | 63.1 |
| 289 | (1-Naphthyl)methyl- | (2-Thienyl)-CH2—CH2—CO— | 564 | 39.2 |
| 290 | 3-Chlorobenzyl- | (2-Thienyl)-CH2—CH2—CO— | 548 | 45.8 |

-continued

| | | | | |
|---|---|---|---|---|
| 291 | 2-Chlorobenzyl- | (2-Chlorophenyl)-CH2—CO— | 562 | 23.7 |
| 292 | 2,4-Dichlorobenzyl- | (2-Chlorophenyl)-CH2—CO— | 596 | |
| 293 | (1-Naphthyl)methyl- | (2-Chlorophenyl)-CH2—CO— | 578 | 55.1 |
| 294 | 2-(4-H2NSO2-phenyl)ethyl- | (2-Chlorophenyl)-CH2—CO— | 621 | 82.7 |
| 295 | (2-Thienyl)methyl- | Phenyl-CH2—NH—CO— | 515 | 8.0 |
| 296 | (2-Thienyl)methyl- | N-Cyclohexyl-NH—CO— | 507 | 31.7 |
| 297 | Benzyl- | N-(2,6-Difluorophenyl)-NH—CO— | 531 | 80.4 |
| 298 | Benzyl- | N-Isopropyl-NH—CO— | 461 | 74.7 |
| 299 | Benzyl- | Phenyl-CH2—NH—CO— | 509 | 48.6 |
| 300 | Benzyl- | N-Cyclohexyl-NH—CO— | 501 | 29.4 |
| 301 | 3-Methoxybenzyl- | N-(2,6-Difluorophenyl)-NH—CO— | 561 | 87.9 |
| 302 | 3-Methoxybenzyl- | N-Isopropyl-NH—CO— | 491 | 80.4 |
| 303 | 3-Methoxybenzyl- | Phenyl-CH2—NH—CO— | 539 | 65.8 |
| 304 | 3-Methoxybenzyl- | N-Cyclohexyl-NH—CO— | 531 | 56.0 |
| 305 | 3-Chlorobenzyl- | N-(2,6-Difluorophenyl)-NH—CO— | 565 | 84.9 |
| 306 | 3-Chlorobenzyl- | N-Isopropyl-NH—CO— | 495 | 90.2 |
| 307 | 3-Chorobenzyl- | Phenyl-CH2—NH—CO— | 543 | 55.8 |
| 308 | 3-Chlorobenzyl- | N-Cyclohexyl-NH—CO— | 535 | 32.1 |
| 309 | 2,3-Dichlorobenzyl- | (2-Thienyl)-CH2—CO— | 568 | 88.9 |
| 310 | (2-Naphthyl)methyl- | (2-Thienyl)-CH2—CO— | 550 | 47.7 |
| 311 | 3-Methylbenzyl- | (2-Thienyl)-CH2—CO— | 514 | 10.4 |
| 312 | 2-Methylbenzyl- | (2-Thienyl)-CH2—CO— | 514 | 12.5 |
| 313 | (CH3)2C=CH—CH2—CH2—C(CH3)=CH—CH2— | (2-Thienyl)-CH2—CO— | 546 | 17.2 |
| 314 | 1-Indanyl- | (2-Thienyl)-CH2—CO— | 526 | 14.4 |
| 315 | 1,2,3,4-Tetrahydro-1-naphthyl- | (2-Thienyl)-CH2—CO— | 540 | 23.5 |
| 316 | 2-Fluorobenzyl- | (2-Thienyl)-CH2—CO— | 518 | 14.4 |
| 317 | 3-Phenylbenzyl- | (2-Thienyl)-CH2—CO— | 576 | 14.5 |
| 318 | (1,2,3,4-Tetrahydro-2-furyl)methyl- | (2-Thienyl)-CH2—CO— | 494 | 16.4 |
| 319 | 2,3-Dichlorobenzyl- | Methoxy-CH2—CH2—CO— | 530 | 38.0 |
| 320 | (2-Naphthyl)methyl- | Methoxy-CH2—CH2—CO— | 512 | 38.8 |
| 321 | 3-Methylbenzyl- | Methoxy-CH2—CH2—CO— | 476 | |
| 322 | 2-Methylbenzyl- | Methoxy-CH2—CH2—CO— | 476 | 66.3 |
| 323 | (CH3)2C=CH—CH2—CH2—C(CH3)=CH—CH2— | Methoxy-CH2—CH2—CO— | 508 | 23.6 |
| 324 | 1-Indanyl- | Methoxy-CH2—CH2—CO— | 488 | 60.5 |
| 325 | 1,2,3,4-Tetrahydro-1-naphthyl- | Methoxy-CH2—CH2—CO— | 502 | 33.8 |
| 326 | 2-Fluorobenzyl- | Methoxy-CH2—CH2—CO— | 480 | 25.6 |
| 327 | 3-Phenylbenzyl- | Methoxy-CH2—CH2—CO— | 538 | 17.4 |
| 328 | (1,2,3,4-Tetrahydro-2-furyl)methyl- | Methoxy-CH2—CH2—CO— | 456 | 87.0 |
| 329 | 2,3-Dichlorobenzyl- | 2-Methoxy-phenyl-CO— | 578 | 25.7 |
| 330 | (2-Naphthyl)methyl- | 2-Methoxy-phenyl-CO— | 560 | 14.4 |
| 331 | 3-Methylbenzyl- | 2-Methoxy-phenyl-CO— | 524 | 37.6 |
| 332 | 2-Methylbenzyl- | 2-Methoxy-phenyl-CO— | 524 | 31.7 |
| 333 | (CH3)2C=CH—CH2—CH2—C(CH3)=CH—CH2— | 2-Methoxy-phenyl-CO— | 556 | 22.3 |
| 334 | 1-Indanyl- | 2-Methoxy-phenyl-CO— | 536 | |
| 335 | 1,2,3,4-Tetrahydro-1-naphthyl- | 2-Methoxy-phenyl-CO— | 550 | 79.6 |
| 336 | 2-Fluorobenzyl- | 2-Methoxy-phenyl-CO— | 528 | 58.1 |
| 337 | 3-Phenylbenzyl- | 2-Methoxy-phenyl-CO— | 586 | 51.2 |
| 338 | (1,2,3,4-Tetrahydro-2-furyl)methyl- | 2-Methoxy-phenyl-CO— | 504 | 50.7 |
| 339 | 2,3-Dichlorobenzyl- | Phenoxy-CH2—CH2—CO— | 592 | 46.8 |
| 340 | (2-Naphthyl)methyl- | Phenoxy-CH2—CH2—CO— | 574 | 37.2 |
| 341 | 3-Methylbenzyl- | Phenoxy-CH2—CH2—CO— | 538 | 44.6 |
| 342 | 2-Methylbenzyl- | Phenoxy-CH2—CH2—CO— | 538 | 85.3 |
| 343 | (CH3)2C=CH—CH2—CH2—C(CH3)=CH—CH2— | Phenoxy-CH2—CH2—CO— | 570 | 48.1 |
| 344 | 1-Indanyl- | Phenoxy-CH2—CH2—CO— | 550 | 52.2 |
| 345 | 1,2,3,4-Tetrahydro-1-naphthyl- | Phenoxy-CH2—CH2—CO— | 564 | 39.8 |
| 346 | 2-Fluorobenzyl- | Phenoxy-CH2—CH2—CO— | 542 | 36.0 |
| 347 | 3-Phenylbenzyl- | Phenoxy-CH2—CH2—CO— | 600 | 19.3 |
| 348 | (1,2,3,4-Tetrahydro-2-furyl)methyl- | Phenoxy-CH2—CH2—CO— | 518 | 46.3 |
| 349 | 2,3-Dichlorobenzyl- | Cyclohexyl-CH2—CO— | 568 | 50.4 |
| 350 | (2-Naphthyl)methyl- | Cyclohexyl-CH2—CO— | 550 | |
| 351 | 3-Methylbenzyl- | Cyclohexyl-CH2—CO— | 514 | 27.2 |
| 352 | 2-Methylbenzyl- | Cyclohexyl-CH2—CO— | 514 | 35.2 |
| 353 | (CH3)2C=CH—CH2—CH2—C(CH3)=CH—CH2— | Cyclohexyl-CH2—CO— | 546 | 47.9 |
| 354 | 1-Indanyl- | Cyclohexyl-CH2—CO— | 526 | 37.2 |
| 355 | 1,2,3,4-Tetrahydro-1-naphthyl- | Cyclohexyl-CH2—CO— | 540 | 46.8 |

-continued

| | | | | |
|---|---|---|---|---|
| 356 | 2-Fluorobenzyl- | Cyclohexyl-CH2—CO— | 518 | 47.4 |
| 357 | 3-Phenylbenzyl- | Cyclohexyl-CH2—CO— | 576 | 61.9 |
| 358 | (1,2,3,4-Tetrahydro-2-furyl)methyl- | Cyclohexyl-CH2—CO— | 494 | 55.5 |
| 359 | 2,3-Dichlorobenzyl- | Cyclopentyl-CH2—CO— | 554 | 37.9 |
| 360 | (2-Naphthyl)methyl- | Cyclopentyl-CH2—CO— | 536 | 36.9 |
| 361 | 3-Methylbenzyl- | Cyclopentyl-CH2—CO— | 500 | 29.4 |
| 362 | 2-Methylbenzyl- | Cyclopentyl-CH2—CO— | 500 | 44.1 |
| 363 | (CH3)2C=CH—CH2—CH2—C(CH3)=CH—CH2— | Cyclopentyl-CH2—CO— | 532 | 48.3 |
| 364 | 1-Indanyl- | Cyclopentyl-CH2—CO— | 512 | 52.6 |
| 365 | 1,2,3,4-Tetrahydro-1-naphthyl- | Cyclopentyl-CH2—CO— | 526 | 45.1 |
| 366 | 2-Fluorobenzyl- | Cyclopentyl-CH2—CO— | 504 | 38.4 |
| 367 | 3-Phenylbenzyl- | Cyclopentyl-CH2—CO— | 562 | 25.5 |
| 368 | (1,2,3,4-Tetrahydro-2-furyl)methyl- | Cyclopentyl-CH2—CO— | 480 | 51.0 |
| 369 | 2,4-Difluorophenyl- | 4-Methylphenyl-SO2— | 590 | 33.7 |
| 370 | 4-tert-Butylphenyl- | 3,4-Dimethoxyphenyl-SO2— | 656 | 50.1 |
| 371 | 4-tert-Butylphenyl- | 2,5-Dimethoxyphenyl-SO2— | 656 | 38.6 |
| 372 | 2,4-Difluorophenyl- | 2,3,4,5,6-Pentamethylphenyl-SO2— | 646 | 23.1 |
| 373 | 2,6-Dichlorophenyl- | 3-Fluoro-2,4-dimethylphenyl-SO2— | 654 | 20.6 |
| 374 | 3-Chloro-4-fluorophenyl- | 4-Fluoro-3,5-dimethylphenyl-SO2— | 638 | 70.3 |
| 375 | 2-Cyanophenyl- | 4-Methyl phenyl-SO2— | 579 | 80.6 |
| 376 | 4-Chloro-2,5-dimethoxyphenyl- | 4-Methylphenyl-SO2— | 648 | 66.6 |
| 377 | 4-Chloro-2,5-dimethoxyphenyl- | 4-Chlorophenyl-SO2— | 668 | 36.8 |
| 378 | 4-Fluorophenyl- | 2,4,5-Trichlorophenyl-SO2— | 660 | 43.6 |
| 379 | 4-(4-Fluorophenoxy)phenyl- | 4-Methylphenyl-SO2— | 664 | |
| 380 | 2-Chlorophenyl- | 2,5-Dimethoxyphenyl-SO2— | 634 | 28.1 |
| 381 | 2-Cyanophenyl- | 2,5-Dimethoxyphenyl-SO2— | 625 | 60.8 |
| 382 | 2,3-Dichlorophenyl- | 3,4-Dichlorophenyl-SO2— | 676 | 47.1 |
| 383 | 4-(4-Chlorophenoxy)-phenyl- | 4-Methylphenyl-SO2— | 680 | 42.2 |
| 384 | 3-Trifluoromethylphenyl- | 4-Methylphenyl-SO2— | 622 | 57.2 |
| 385 | 2-Cyanophenyl- | 4-tert-Butylphenyl-SO2— | 621 | 64.8 |
| 386 | 2-Acetylphenyl- | 2,4-Dichlorophenyl-SO2— | 650 | 33.5 |
| 387 | 2-Acetylphenyl- | 2,3-Dichlorophenyl-SO2— | 650 | 29.8 |
| 388 | Benzyl- | (3-Thienyl)-CH—(CH3)—CO— | 514 | 63.7 |
| 389 | Benzyl- | (2-Furyl)-CH2—CO— | 484 | 51.5 |
| 390 | (1-Naphthyl)methyl- | (2-Thienyl)-CH—(CH3)—CO— | 564 | 89.8 |
| 391 | (1-Naphthyl)methyl- | (2-Furyl)-CH2—CO— | 534 | 55.4 |
| 392 | (1-Phenylcyclopentyl)methyl- | (2-Thienyl)-CH2—CO— | 568 | 55.6 |
| 393 | (1-Phenylcyclopentyl)methyl- | (2-Thienyl)-CH—(CH3)—CO— | 582 | 16.7 |
| 394 | (1-Phenylcyctopentyl)methyl- | (2-Furyl)-CH2—CO— | 552 | 72.5 |
| 395 | 2-Ethyl-2-(4-methoxyphenyl)butyl- | (2-Thienyl)-CH2—CO— | 600 | 50.9 |
| 396 | [3-(Pyrrolidine-1-carbonyl)-4,5-dihydro-isoxazol-5-yl]-methyl- | (2-Thienyl)-CH2—CO— | 590 | 53.2 |
| 397 | [3-(Pyrrolidine-1-carbonyl)-4,5-dihydro-isoxazol-5-yl]-methyl- | (2-Thienyl)-CH—(CH3)—CO— | 604 | 44.0 |
| 398 | Phenyl- | Phenyl-SO-2 | 540 | |
| 399 | 4-Acetylamino-2-methylphenyl- | 4-Chlorophenyl-SO2— | 645 | |
| 400 | 5-Aceylamino-2-methylphenyl- | 2,5-Dichlorophenyl-SO2— | 679 | |
| 401 | 4-Acetylamino-2,6-dimethylphenyl- | 4-Methylphenyl-SO2— | 639 | |
| 402 | Phenyl- | 4-Methylphenyl-SO2— | 554 | |
| 403 | 2-Acetylphenyl- | 2,4,5-Trichlorophenyl-SO2— | 684 | |
| 404 | 2-Acetylphenyl- | 4-Trifluoromethyl-phenyl-SO2— | 650 | |
| 405 | 4-Chlorophenyl | 4-Chlorophenyl-SO2— | 608 | |
| 406 | 4-Chlorophenyl- | Phenyl-SO2— | 574 | |
| 407 | 3-Acetylphenyl- | 4-Methoxyphenyl-SO2— | 612 | |
| 408 | 3-Acetylphenyl- | 2-Chlorophenyl-SO2— | 616 | |
| 409 | 3-Acetylphenyl- | 2-Chloro-6-methylphenyl-SO2— | 630 | |
| 410 | 3-Acetylphenyl- | 4-tert-Butylphenyl-SO2— | 638 | |

-continued

| | | | |
|---|---|---|---|
| 411 | 3-Acetylphenyl- | 4-Fluorophenyl-SO2— | 600 |
| 412 | 3-Acetylphenyl- | 3,4-Dichlorophenyl-SO2— | 650 |
| 413 | 3-Acetylphenyl- | 2,4-Difluorophenyl-SO2— | 618 |
| 414 | 3-Acetylphenyl- | 3-Trifluoromethylphenyl-SO2— | 650 |
| 415 | 4-Trifluoromethylphenyl- | 4-Acetylaminophenyl-SO2— | 665 |
| 416 | 2,5-Difluorophenyl- | 4-Acetylaminophenyl-SO2— | 633 |
| 417 | 4-tert-Butylphenyl- | 4-Acetylaminophenyl-SO2— | 653 |
| 418 | 4-Isopropylphenyl- | 2-Chloro-4-cyanophenyl-SO2— | 641 |
| 419 | 4-Methoxyphenyl- | 4-Acetylaminophenyl-SO2— | 627 |
| 420 | 4-Ethoxyphenyl- | 4-Chlorophenyl-SO2— | 618 |
| 421 | 5-Chloro-2-methoxyphenyl- | 4-Chlorophenyl-SO2— | 638 |
| 422 | 5-Chloro-2-methoxyphenyl- | 2,4,5-Trichlorophenyl-SO2— | 706 |
| 423 | 2-Fluorophenyl- | 4-Acetylaminophenyl-SO2— | 615 |
| 424 | 1-Naphthyl- | 4-Acetylaminophenyl-SO2— | 647 |
| 425 | 2-Trifluoromethylphenyl- | 4-Acetylaminophenyl-SO2— | 665 |
| 426 | 2-Ethylphenyl- | 4-Chlorophenyl-SO2— | 602 |
| 427 | 2,4-Dimethylphenyl- | Phenyl-SO2— | 568 |
| 428 | 2,4,5-Trimethylphenyl- | 4-Chlorophenyl-SO2— | 616 |
| 429 | 2,5-Dimethylphenyl- | 2,4,5-Trichlorophenyl-SO2— | 670 |
| 430 | 5-Chloro-2-methylphenyl- | 4-Chlorophenyl-SO2— | 622 |
| 431 | 4-Fluorophenyl- | Phenyl-SO2— | 558 |
| 432 | 3-Chloro-2-methylphenyl- | Phenyl-SO2— | 588 |
| 433 | 4-Chloro-2-methylphenyl- | Phenyl-SO2— | 588 |
| 434 | 2,3-Dichtorophenyl- | 4-Chlorophenyl-SO2— | 642 |
| 435 | 3-Trifluoromethylphenyl- | 2,4,5-Trichlorophenyl-SO2— | 710 |
| 436 | 5-Chloro-2-methylphenyl- | 2,4,5-Trichlorophenyl-SO2— | 690 |
| 437 | 2-Fluorophenyl- | 2,4,5-Trichlorophenyl-SO2— | 660 |
| 438 | 2,6-Dimethyl phenyl- | Phenyl-SO2— | 568 |
| 439 | 2,3-Dimethylphenyl- | Phenyl-SO2— | 568 |
| 440 | 1-Naphthyl- | 3,4-Dichlorophenyl-SO2— | 658 |
| 441 | 4-Ethoxyphenyl- | 3,4-Dichlorophenyl-SO2— | 652 |
| 442 | 1-Naphthyl- | 4-Chlorophenyl-SO2— | 624 |
| 443 | 3,5-Dichlorophenyl- | 3,4-Dichlorophenyl-SO2— | 676 |
| 444 | 2,4,5-Trimethylphenyl- | 4-Acetylaminophenyl-SO2— | 639 |
| 445 | 3,4-Dichlorophenyl- | 3,4-Dichlorophenyl-SO2— | 676 |
| 446 | 3,4-Dimethoxyphenyl- | 4-Methylphenyl-SO2— | 614 |
| 447 | 4-Fluorophenyl- | 4-Methylphenyl-SO2— | 572 |
| 448 | 4-Bromophenyl- | 2-Naphthyl-SO2— | 668 |
| 449 | 2-Chlorophenyl- | 2-Naphthyl-SO2— | 624 |
| 450 | 2-Methylphenyl- | 2-Naphthyl-SO2— | 604 |
| 451 | 2-Methoxyphenyl- | 2-Naphthyl-SO2— | 620 |
| 452 | Phenyl- | 2-Naphthyl-SO2— | 590 |
| 453 | 2,6-Diethylphenyl- | Phenyl-SO2— | 596 |
| 454 | 2,6-Diisopropylphenyl- | Phenyl-SO2— | 624 |
| 455 | 2-Biphenyl- | 4-Methylphenyl-SO2— | 630 |
| 456 | 2-Naphthyl- | 2-Naphthyl-SO2— | 640 |
| 457 | 4-Methylphenyl- | 2-Naphthyl-SO2— | 604 |
| 458 | 2,4-Dimethoxyphenyl- | 4-Methylphenyl-SO2— | 614 |
| 459 | 2,5-Dimethylphenyl- | 4-Acetylaminophenyl-SO2— | 625 |
| 460 | 2-Chloro-4-methoxyphenyl- | 4-Chlorophenyl-SO2— | 638 |
| 461 | 2-Methoxy-5-methylphenyl- | Phenyl-SO2— | 584 |
| 462 | 3-Methoxy-4-methylphenyl- | Phenyl-SO2— | 584 |
| 463 | 2-Methoxyphenyl- | 4-Chlorophenyl-SO2— | 604 |
| 464 | 3-Hydroxyphenyl- | 4-Chlorophenyl-SO2— | 590 |
| 465 | 3,4-Dichlorophenyl- | 4-Chlorophenyl-SO2— | 642 |
| 466 | 3-Acetylphenyl- | 4-Chlorophenyl-SO2— | 616 |
| 467 | 2,6-Diethylphenyl- | 4-Methylphenyl-SO2— | 610 |
| 468 | 5-Chloro-2-methoxyphenyl- | 4-Acetylaminophenyl-SO2— | 661 |
| 469 | 5-Chloro-2-methylphenyl- | Phenyl-SO2— | 588 |
| 470 | 2-Chloro-5-trifluoromethylphenyl- | 4-Chlorophenyl-SO2— | 676 |
| 471 | 2-Acetylphenyl- | 2,4-Difluorophenyl-SO2— | 618 |
| 472 | 1-Acetylamino-2-naphthyl- | 4-Methylphenyl-SO2— | 661 |
| 473 | 4-Ethyl phenyl- | 4-Chlorophenyl-SO2— | 602 |
| 474 | 2,5-Dichlorophenyl- | 4-Methoxyphenyl-SO2— | 638 |
| 475 | 2,4-Difluorphenyl- | 4-Fluoro-3,5-dimethylphenyl-SO2— | 622 |
| 476 | 4-Trifluoromethoxyphenyl- | 2,5-Dimethoxyphenyl-SO2— | 684 |
| 477 | 2-Chlorophenyl- | 3,4-Dimethoxyphenyl-SO20 | 634 |
| 478 | 2-Methyl-1-naphthyl- | Phenyl-SO2— | 604 |
| 479 | 2,6-Dimethylphenyl- | 4-Acetylaminophenyl-SO2— | 625 |
| 480 | 1,3-Dihydro-1-oxo-benzo[c]furan-6-yl | 4-Chlorophenyl-SO2— | 630 |

| | | -continued | | |
|---|---|---|---|---|
| 481 | Benzyl- | (5-methyl-2-thienyl)-OH—(CH3)—CO— | 528 | 62.6 |
| 482 | 3-Nitrobenzyl- | (2-Thienyl)-CH2—CO— | 545 | |
| 483 | Neopentyl- | (2-Thienyl)-CH2—CO— | 480 | |
| 484 | Isopropyl- | (2-Thienyl)-CH2—CO— | 452 | |
| 485 | 2-Ethoxybenzyl- | (2-Thienyl)-CH2—CO— | 544 | |
| 486 | 3-Nitrobenzyl- | (3-Thienyl)-CH2—CO— | 545 | |
| 487 | Neopentyl- | (3-Thienyl)-CH2—CO— | 480 | |
| 488 | Isopropyl- | (3-Thienyl)-CH2—CO— | 452 | |
| 489 | 2-Ethoxybenzyl- | (3-Thienyl)-CH2—CO— | 544 | |
| 490 | 2,2,2-Trifluoroethyl- | (3-Thienyl)-CH2—CO— | 492 | |
| 491 | 2-(3-Trifluoromethyl-phenyl)-ethyl | (3-Thienyl)-CH2—CO— | 582 | |
| 492 | 3-Nitrobenzyl- | (2-Fluorophenyl)-CH2—CO— | 557 | |
| 493 | Neopentyl- | (2-Fluorophenyl)-CH2—CO— | 492 | |
| 494 | Isopropyl | (2-Fluorophenyl)-CH2—CO— | 464 | |
| 495 | 2-Ethoxybenzyl- | (2-Fluorophenyl)-CH2—CO— | 556 | |
| 496 | 2-(3-Trifluoromethyl-phenyl)-ethyl | (2-Fluorophenyl)-CH2—CO— | 594 | |
| 497 | 1-Indanyl- | Phenyl-CH2—CO— | 520 | |
| 498 | 3-Nitrobenzyl- | Phenyl-CH2—CO— | 539 | |
| 499 | Neopentyl- | Phenyl-CH2—CO— | 474 | |
| 500 | Isopropyl- | Phenyl-CH2—CO— | 446 | |
| 501 | 2,2,2-Trifluoroethyl- | Phenyl-CH2—CO— | 486 | |
| 502 | 2-(3-Trifluoromethyl-phenyl)-ethyl | Phenyl-CH2—CO— | 576 | |
| 503 | 1-Indanyl- | (4-Chlorophenyl)-CH2—CO— | 554 | |
| 504 | 3-Nitrobenzyl- | (4-Chlorophenyl)-CH2—CO— | 573 | |
| 505 | Neopentyl- | (4-Chlorophenyl)-CH2—CO— | 508 | |
| 506 | Isopropyl- | (4-Chlorophenyl)-CH2—CO— | 480 | |
| 507 | 2-Ethoxybenzyl- | (4-Chlorophenyl)-CH2—CO— | 572 | |
| 508 | 2-(3-Trifluoromethyl-phenyl)-ethyl | (4-Chlorophenyl)-CH2—CO— | 610 | |
| 509 | 3-Nitrobenzyl- | 4-Chlorophenyl-CO— | 559 | |
| 510 | Isopropyl- | 4-Chlorophenyl-CO— | 466 | |
| 511 | 2-Ethoxybenzyl- | 4-Chlorophenyl-CO— | 558 | |
| 512 | 2-(3-Trifluoromethyl-phenyl)-ethyl | 4-Chlorophenyl-CO— | 596 | |

| No. | R2 | R1-X | R7 | MS (ES−): M-1) | Residual activity (%) of the NCBE at 10 μM |
|---|---|---|---|---|---|
| 513 | Benzyl- | (2-Thienyl)-CH2—CO— | 4-Methyl- | 514 | 88.6 |
| 514 | (1-Naphthyl)methyl- | (2-Thienyl)-CH2—CO— | 4-Methyl- | 564 | 74.9 |
| 515 | (2-Naphthyl)methyl- | (2-Thienyl)-CH2—CO— | 4-Methyl- | 564 | 68.9 |
| 516 | 2-Chlorobenzyl- | (2-Thienyl)-CH2—CO— | 4-Methyl- | 548 | 98.7 |
| 517 | (2-Thienyl)methyl- | (2-Thienyl)-CH2—CO— | 4-Methyl- | 520 | 86.2 |
| 518 | 2-Phenylethyl- | (2-Thienyl)-CH2—CO— | 4-Methyl- | 528 | 93.5 |
| 519 | 2-Fluorobenzyl- | (2-Thienyl)-CH2—CO— | 4-Methyl- | 532 | 95.6 |
| 520 | 2,3-Dichlorobenzyl- | (2-Thienyl)-CH2—CO— | 4-Methyl- | 582 | 85.9 |
| 521 | Benzyl- | (2-Thienyl)-CH(CH3)—CO— | 4-Methyl- | 528 | 88.2 |
| 522 | (1-Naphthyl)methyl- | (2-Thienyl)-CH(CH3)—CO— | 4-Methyl- | 578 | 85.6 |
| 523 | (2-Naphthyl)methyl- | (2-Thienyl)-CH(CH3)—CO— | 4-Methyl- | 578 | 92.3 |
| 524 | 2-Chlorobenzyl- | (2-Thienyl)-CH(CH3)—CO— | 4-Methyl- | 562 | |
| 525 | (2-Thienyl)methyl- | (2-Thienyl)-CH(CH3)—CO— | 4-Methyl- | 534 | 74.0 |
| 526 | 2-Phenylethyl- | (2-Thienyl)-CH(CH3)—CO— | 4-Methyl- | 542 | 64.9 |
| 527 | 2-Fluorobenzyl- | (2-Thienyl)-CH(CH3)—CO— | 4-Methyl- | 546 | 67.5 |
| 528 | 2,3-Dichlorobenzyl- | (2-Thienyl)-CH(CH3)—CO— | 4-Methyl- | 596 | 72.0 |
| 529 | Benzyl- | (4-Chlorophenyl)-CH2—CO— | 4-Methyl- | 542 | 89.4 |
| 530 | (1-Naphthyl)methyl- | (4-Chlorophenyl)-CH2—CO— | 4-Methyl- | 592 | 89.8 |
| 531 | (2-Naphthyl)methyl- | (4-Chlorophenyl)-CH2—CO— | 4-Methyl- | 592 | 75.6 |
| 532 | 2-Chlorobenzyl- | (4-Chlorophenyl)-CH2—CO— | 4-Methyl- | 576 | 71.0 |
| 533 | (2-Thienyl)methyl- | (4-Chlorophenyl)-CH2—CO— | 4-Methyl- | 548 | 75.5 |
| 534 | 2-Phenylethyl- | (4-Chlorophenyl)-CH2—CO— | 4-Methyl- | 556 | 80.0 |
| 535 | 2-Fluorobenzyl- | (4-Chlorophenyl)-CH2—CO— | 4-Methyl- | 560 | 84.0 |
| 536 | 2,3-Dichlorobenzyl- | (4-Chlorophenyl)-CH2—CO— | 4-Methyl- | 610 | 76.3 |
| 537 | Benzyl- | (3-Thienyl)-CH2—CO— | 4-Methyl- | 514 | 54.4 |
| 538 | (1-Naphthyl)methyl- | (3-Thienyl)-CH2—CO— | 4-Methyl- | 564 | 80.3 |
| 539 | (2-Naphthyl)methyl- | (3-Thienyl)-CH2—CO— | 4-Methyl- | 564 | 65.2 |
| 540 | 2-Chlorobenzyl- | (3-Thienyl)-CH2—CO— | 4-Methyl- | 548 | 64.6 |
| 541 | (2-Thienyl)methyl | (3-Thienyl)-CH2—CO— | 4-Methyl- | 520 | 52.8 |
| 542 | 2-Phenylethyl- | (3-Thienyl)-CH2—CO— | 4-Methyl- | 528 | 67.4 |
| 543 | 2-Fluorobenzyl- | (3-Thienyl)-CH2—CO— | 4-Methyl- | 532 | 55.3 |
| 544 | 2,3-Dichlorobenzyl- | (3-Thienyl)-CH2—CO— | 4-Methyl- | 582 | 82.2 |
| 545 | Benzyl- | Cyclohexyl-CH2—CO— | 4-Methyl- | 514 | 70.1 |

-continued

| | | | | | |
|---|---|---|---|---|---|
| 546 | (1-Naphthyl)methyl- | Cyclohexyl-CH2—CO— | 4-Methyl- | 564 | 63.6 |
| 547 | (2-Naphthyl)methyl- | Cyclohexyl-CH2—CO— | 4-Methyl- | 564 | 76.5 |
| 548 | 2-Chlorobenzyl | Cyclohexyl-CH2—CO— | 4-Methyl- | 548 | 65.2 |
| 549 | (2-Thienyl)methyl- | Cyclohexyl-CH2—CO— | 4-Methyl- | 520 | 67.3 |
| 550 | 2-Phenylethyl- | Cyclohexyl-CH2—CO— | 4-Methyl- | 528 | 63.3 |
| 551 | 2-Fluorobenzyl- | Cyclohexyl-CH2—CO— | 4-Methyl- | 532 | 82.6 |
| 552 | 2,3-Dichlorobenzyl- | Cyclohexyl-CH2—CO— | 4-Methyl- | 582 | 61.5 |
| 553 | Benzyl- | (2-Thienyl)-CH2—CO— | 5-Chloro- | 534 | 85.7 |

Example 554

4'-{[Benzyl-(2-thiophen-2-ylacetyl)amino]methyl}-3'-chlorobiphenyl-2-sulfonylcyanamide

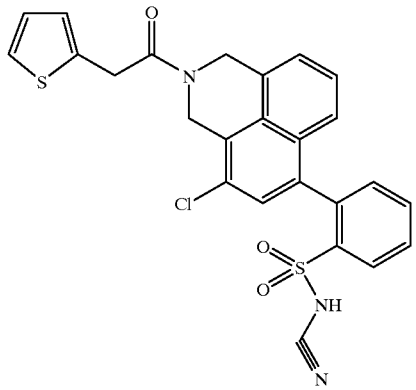

a) 4-Bromo-1-bromomethyl-2-chlorobenzene 7.1 ml of 4-bromo-2-chorotoluene are dissolved in 20 ml of chlorobenzene and treated with a mixture of 9.4 g of N-bromosuccinimide and 200 mg of dibenzoyl peroxide in portions at 130□ C. The mixture is refluxed for 30 minutes, diluted with 100 ml of $CH_2Cl_2$ after cooling and washed once with 50 ml of a saturated aqueous $Na_2SO_3$ solution each time and 100 ml of a saturated aqueous $NaHCO_3$ solution. It is dried over $Na_2SO_4$ and the solvent is removed in vacuo. 11.0 g of a pale yellow oil are obtained.

$R_f$ (EA/HEP 1:8)=0.49 MS (DCI): 283 $(M+H)^+$ b) Benzyl-(4-bromo-2-chlorobenzyl)amine 765 μl of benzylamine are dissolved in 10 ml of THF (anhydrous) and treated with 1.0 g of 4-bromo-1-bromomethyl-2-chlorobenzene at 0° C. and stirred at RT for 4 h. 100 ml of a half-saturated aqueous $Na_2CO_3$ solution are then added and the mixture is extracted three times with 100 ml of EA each time. It is dried over $MgSO_4$ and chromatographed on silica gel using DIP. 590 mg of a colorless oil are obtained.

$R_f$ (DIP)=0.30 MS (DCI): 310 $(M+H)^+$ c) 2-Thiophen-2-ylacetic acid benzyl-(4-bromo-2-chlorobenzyl)amide 580 mg of benzyl-(4-bromo-2-chlorobenzyl)amine are dissolved in 10 ml of $CH_2Cl_2$ (anhydrous) and treated first with 300 μl of pyridine, then with 330 mg of 2-thiophen-2-ylacetyl chloride. The mixture is stirred at RT for 4 h, then diluted with 100 ml of $CH_2Cl_2$ and washed with 50 ml of a saturated aqueous $Na_2CO_3$ solution. It is dried over $MgSO_4$ and the solvent is removed in vacuo. It is chromatographed on silica gel using DIP and 490 mg of a colorless oil are obtained.

$R_f$ (DIP)=0.56 MS (ES): 434 $(M+H)^+$ d) 4'-{[Benzyl-(2-thiophen-2-ylacetyl)amino]methyl}-3'-chlorobiphenyl-2-sulfonic acid t-butylamide 480 mg of 2-thiophen-2-ylacetic acid benzyl-(4-bromo-2-chlorobenzyl)-amide, 426 mg of N-t-butyl-2-dihydroxyboran-2-yl benzenesulfonamide (J. Med. Chem. 1997, 40, 547), 26.2 mg of triphenylphosphine, 11.2 mg of Pd(II) acetate and 133 mg of $Na_2CO_3$ are suspended in 1 ml of water, 0.5 ml of EtOH and 5 ml of toluene and refluxed for 2 h. The mixture is allowed to cool, then the volatile constituents are removed in vacuo. The residue is taken up using 2 ml of $CH_2Cl_2$ and chromatographed on silica gel using DIP. 520 mg of a colorless, amorphous solid are obtained.

$R_f$ (DIP)=0.20 MS (ES): 567 $(M+H)^+$ e) 4'-{[Benzyl-(2-thiophen-2-ylacetyl)amino]methyl}-3'-chlorobiphenyl-2-sulfonamide 510 mg of 4'-{[benzyl-(2-thiophen-2-ylacetyl)amino]methyl}-3'-chloro-biphenyl-2-sulfonic acid t-butylamide and 110 μl of anisole are allowed to stand at RT for 18 h in 3 ml of trifluoroacetic acid. The volatile constituents are then removed in vacuo, the residue is taken up in 5 ml of toluene and volatile constituents are again removed in vacuo. 586 g of a colorless oil are obtained, which is used further without purification.

$R_f$ (DIP)=0.12 MS (ES): 511 $(M+H)^+$ f) 4'-{[Benzyl-(2-thiophen-2-ylacetyl)amino]methyl}-3'-chlorobiphenyl-2-sulfonylcyanamide 586 mg of 4'-{[benzyl-(2-thiophen-2-ylacetyl)amino]methyl}-3'-chlorobiphenyl-2-sulfonamide, 372 mg of $K_2CO_3$ and 180 μl of a 5 molar solution of BrCN in acetonitrile are refluxed for 1.5 h. After cooling, the entire reaction mixture is chromatographed on silica gel using EA/MeOH 10:1. 181 mg of a colorless, amorphous solid are obtained.

$R_f$ (EA/MeOH 10:1)=0.22 IR (CN): 2172.5$cm^{-1}$ MS (ES): 536 $(M+H)^+$

Residual activity of the NCBE at 10 μM: 15%

The title compound of Example 555 was synthesized analogously to Example 554.

Example 555

4'-{[Benzyl-(2-thiophen-2-ylacetyl)amino]methyl}-3'-methylsulfonyl-biphenyl-2-sulfonylcyanamide

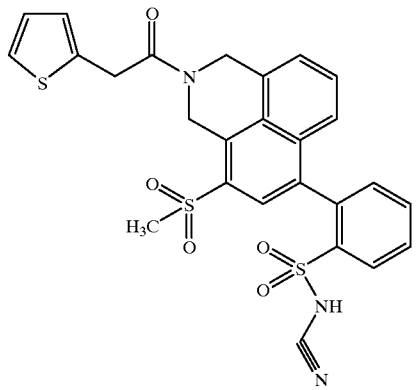

a) 2-Bromo-5-methylbenzenesulfonyl chloride 40 g of 4-bromotoluene are slowly introduced into 250 ml of chlorosulfonic acid at −10° C. with stirring. The mixture is stirred at this temperature for 30 minutes, allowed to warm to 0° C. and poured on to excess ice. The product is filtered off with suction and washed with a little water. It is dried over $P_4O_{10}$ in vacuo and 63 g of a colorless solid are obtained, which is directly reacted further.

b) 2-Bromo-5-methylbenzenesulfinic acid 37.6 g of sodium sulfite are dissolved in 500 ml of water and heated to 70° C. 62 g of 2-bromo-5-methylbenzenesulfonyl chloride are added in portions at this temperature. A 10N aqueous NaOH solution is simultaneously added dropwise here such that the pH of the solution is kept between pH=9 and pH=10. The mixture is stirred at 70° C. for 1.5 hours, and the solution is filtered off and then adjusted to pH=0 in an ice bath using a saturated aqueous HCl solution. It is subsequently stirred for 30 minutes, then the product is filtered off, washed with a little water and dried. 49.6 g of white crystals are obtained, mp 120–122° C. MS (ES): 236 (M+H)$^+$ c) Sodium 2-bromo-5-methylbenzenesulfinate 49.6 g of 2-bromo-5-methylbenzenesulfinic acid are dissolved in 400 ml of methanol and treated with an equimolar amount of NaOH in 50 ml of water. The mixture is stirred at RT for 3 hours, the solution is filtered off and the solvents are then removed in vacuo. Finally, residues of water are removed azeotropically using 50 ml of toluene. The solid residue is dried in vacuo over $P_4O_{10}$ and 54.0 g of product are obtained, mp 288–290° C. (with decomposition).

d) 1-Bromo-2-methanesulfonyl-4-methylbenzene 54.0 g of sodium 2-bromo-5-methylbenzenesulfinate are suspended in 300 ml of anhydrous DMF and treated with 45.7 ml of methyl iodide. The temperature of the solution rises to 50° C. in the course of this. It is stirred at 50° C. for 3 hours and the DMF is removed in vacuo. The residue is stirred with 500 ml of water, subsequently stirred at 0° C. for 1 hour and filtered off. The product is washed with water, dried and recrystallized from 400 ml of HEP/250 ml of EA using activated carbon. 27.0 g of colorless crystals are obtained, mp 110–114° C.

$R_f$ (EA/HEP 1:4)=0.09 MS (DCI): 250 (M+H)$^+$ e) 1-Bromo-4-bromomethyl-2-methanesulfonylbenzene 9.9 g of 1-bromo-2-methanesulfonyl-4-methylbenzene are taken up in 100 ml of chlorobenzene, 77 mg of benzoyl peroxide and 7.1 g of N-bromosuccinimide are added and the mixture is refluxed for 1 hour. The solvent is then removed in vacuo, the residue is taken up in 100 ml of $CH_2Cl_2$ and the solution is washed twice with 50 ml of a saturated aqueous $Na_2CO_3$ solution and once with 50 ml of water. It is dried over $Na_2SO_4$ and the solvent is removed in vacuo. The residue is recrystallized from 80 ml of HEP/30 ml of EA and 6.9 g of a pale yellow solid are obtained, mp 120–124° C.

$R_f$ (EA/HEP 1:2)=0.38 MS (DCI): 250 (M+H)$^+$ f) Benzyl-(4-bromo-2-methylsulfonylbenzyl)amine

652 μl of benzylamine are dissolved in 10 ml of THF (anhydrous) and 1.0 g of 1-bromo-4-bromomethyl-2-methylsulfonylbenzene is slowly added at 0° C. The mixture is stirred at RT for 4 h, then treated with 100 ml of a saturated aqueous $Na_2CO_3$ solution and extracted twice using 100 ml of EA each time. It is dried over $MgSO_4$ and the solvent is removed in vacuo. Chromatography on silica gel using MTB/DIP 1:1 yields 510 mg of a colorless oil.

$R_f$ (DIP)=0.10 MS (ES): 354 (M+H)$^+$ g) 4'-{[Benzyl-(2-thiophen-2-ylacetyl)amino]methyl}-3'-methylsulfonylbiphenyl-2-sulfonylcyanamide $R_f$ (EA/MeOH 10:1)=0.21 IR (CN): 2175.3 cm$^{-1}$ MS (ES): 580 (M+H)$_+$ Residual activity of the NCBE at 10 μM: 31%

Example 556

4'-{[Benzyl-(2-thiophen-2-sulfonyl)amino]methyl}-3'-chlorobiphenyl-2-sulfonylcyanamide

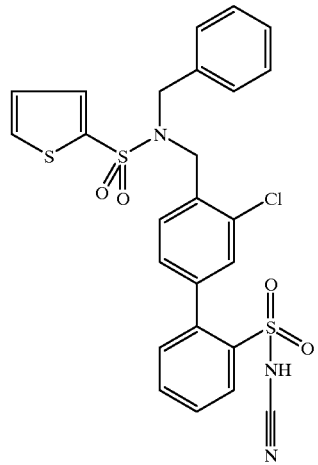

a) Thiophene-2-sulfonic acid benzyl-(4-bromo-2-chlorobenzyl)amide 2.0 g of benzyl-(4-bromo-2-chlorobenzyl)amine (Example X b) and 1.0 g of pyridine are dissolved in 20 ml of CH$_2$Cl$_2$ and slowly treated with 1.4 g of thiophene-2-sulfonyl chloride at RT. The mixture is stirred at RT for 4 h, then diluted with 200 ml of EA and washed twice with 100 ml each of a 5% aqueous sodium hydrogensulfate solution and twice with 50 ml each of a saturated aqueous sodium carbonate solution. It is dried over magnesium sulfate and the solvent is removed in vacuo. Chromatography on silica gel using DIP yields 1.5 g of a colorless oil.

R$_f$ (DIP)=0.21 MS (FAB): 456 (M+H)$^+$

Further reaction to give the title compound of Example 556 is carried out analogously to Example 554 d)–f).

b) 4'-{[Benzyl-(thiophene-2-sulfonyl)amino]methyl}-3'-chlorobiphenyl-2-sulfonylcyanamide R$_f$ (EA/MeOH 10:1)=0.17 IR (CN): 2178.5 cm$^{-1}$ MS (FAB): 580 (M+Na)$^+$ Residual activity of the NCBE at 10 μM: 0%

The title compound of Example 557 is synthesized from the title compound of Example 555 b) analogously to Example 556:

Example 557

4'-{[Benzyl(thiophene-2-sulfonyl)amino]methyl}-3'-methylsulfonylbiphenyl-2-sulfonylcyanamide

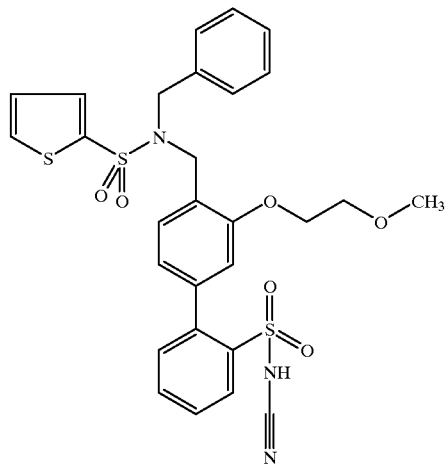

R$_f$ (EA/MeOH 10:1)=0.28 IR (CN): 2175.0 cm$^{-1}$ MS (ES): 602 (M+H)$^+$

Residual activity of the NCBE at 10 μM: 14%

Example 558

4'-{[Benzyl(thiophene-2-sulfonyl)amino]methyl}-3'-(2-methoxy)ethoxy-biphenyl-2-sulfonylcyanamide

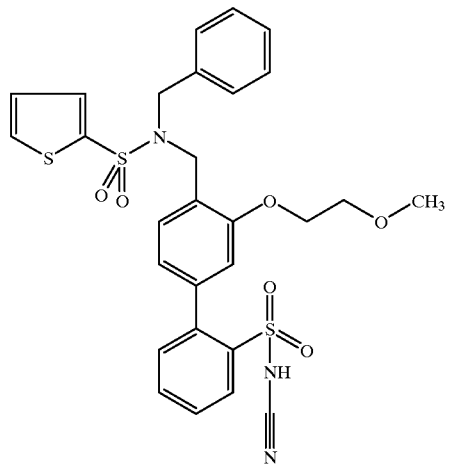

a) 4-Methyl-3-(2-methoxy)ethoxyaniline 22.0 g of 3-hydroxy-4-methylaniline, 24.9 g of 2-bromoethyl methyl ether and 233 g of Cs$_2$CO$_3$ are dissolved in 570 ml of DMF and stirred at 40° C. for 8 h. 3 l of a 10% aqueous sodium hydrogencarbonate solution are added, and the mixture is extracted 6 times with 750 ml of EA each time and washed twice with 1 l of a 10% aqueous sodium hydrogencarbonate solution each time. It is dried over sodium sulfate and the solvent is removed in vacuo. 32.9 g of a yellow oil are obtained, which is employed further as such.

R$_f$ (EAHEP 1:1)=0.33 b) 4-Methyl-3-(2-methoxy)ethoxybromobenzene 32.8 g of 4-methyl-3-(2-methoxy)ethoxyaniline are suspended in 660 ml of a half-saturated aqueous HBr solution and a solution of 12.59 of NaNO$_3$ in 25 ml of water is slowly added dropwise at 0°C. The mixture is subsequently stirred at 0° C. for 30 minutes and this solution is then slowly added to a solution of 51.9 g of CuBr in 490 ml of a saturated aqueous HBr solution heated to 50° C. The reaction mixture is then slowly heated from 50° C. to 70° C. over a period of 6 h. After subsequent cooling, it is extracted 4 times with 500 ml of diethyl ether each time, washed with 500 ml of a saturated aqueous NaCl solution and dried over sodium sulfate. Chromatography on silica gel using EA/HEP 1:8 yields 15.4 g of a colorless oil.

R$_f$ (EA/HEP 1:1)=0.41 MS (DCI): 245 (M+H)$^+$ c) 4-Bromomethyl-3-(2-methoxy)ethoxybromobenzene 15.3 g of 4-methyl-3-(2-methoxy)ethoxybromobenzene are dissolved in 300 ml of chlorobenzene and a mixture of 11.1 g of N-bromosuccinimide and 125 mg of benzoyl peroxide is added in portions under reflux. The mixture is refluxed for 24 h, the solvent is removed in vacuo and the residue is then taken up using 500 ml of CH$_2$Cl$_2$. The mixture is washed first with 200 ml of a saturated aqueous Na$_s$SO$_4$ solution, then with 100 ml of a saturated aqueous sodium carbonate solution. It is dried over sodium sulfate and the solvent is removed in vacuo. Chromatography on silica gel using EA/HEP 1:15 yields 12.8 g of a pale yellow oil.

$R_f$ (EA/HEP 1:4)=0.42 MS (DCI): 323 (M+H)$^+$ d) Benzyl-[4-bromo-2-(2-methoxy)ethoxybenzyl)amine 2.4 ml of benzylamine are dissolved in 20 ml of THF (anhydrous) and slowly treated with 3.2 g of 4-bromomethyl-3-(2-methoxy)ethoxybromobenzene at 0° C. The mixture is stirred at RT for 19 h, then diluted with 200 ml of EA and washed with 100 ml of a saturated aqueous sodium carbonate solution. It is dried over magnesium sulfate and the solvent is removed in vacuo. Chromatography on silica gel using MTB yields 1.3 g of a colorless oil.

$R_f$ (MTB)=0.20 MS (DCI): 350 (M+H)$^+$ e) Thiophene-2-sulfonic acid benzyl-[4-bromo-2-(2-methoxy)ethoxy-benzyl]amide 1.2 g of benzyl-[4-bromo-2-(2-methoxy)ethoxybenzyl)amine, 713 mg of thiophene-2-sulfonyl chloride and 430 μl of pyridine are dissolved in 50 ml of $CH_2Cl_2$ and stirred at RT for 17 h. The mixture is then diluted with 100 ml of $CH_2Cl_2$ and first washed twice with 50 ml of a 5% aqueous sodium hydrogensulfate solution each time and then with 50 ml of a saturated aqueous sodium carbonate solution. It is dried over magnesium sulfate and the solvent is removed in vacuo. Chromatography on silica gel using DIP yields 900 mg of a colorless oil.

$R_f$ (DIP)=0.2 MS (ES): 496 (M+H)$^+$ f) Dihydroxyboran-2-ylbenzenesulfonamide 50 g of N-t-butyl-2-dihydroxyboran-2-ylbenzenesulfonamide (J. Med. Chem. 1997, 40, 547) and 23.3 g of anisole are dissolved in 500 ml of trifluoroacetic acid and allowed to stand at RT for 2 days. The volatile constituents are removed in vacuo, taken up in 100 ml of water and the volatile constituents are again removed in vacuo. The residue is finally taken up in 100 ml of toluene and the volatile constituents are again removed in vacuo. 56 g of a colorless oil are obtained, which is employed further without purification.

$R_f$ (MTB)~0.4 g) Dihydroxyboran-2-ylbenzenesulfonic acid dimethylaminomethylenamide 20 g of dihydroxyboran-2-ylbenzenesulfonamide and 66 ml of dimethylformamide dimethyl acetal are dissolved in 200 ml of DMF (anhydrous) and allowed to stand at RT for 18 h. The reaction mixture is poured onto 1.5 l of water and extracted 4 times with 500 ml of EA each time. It is dried over magnesium sulfate and the solvent is removed in vacuo. Crystallization from 100 ml of EA yields 5.2 g of colorless crystals, mp 175° C. (with decomposition).

$R_f$ (EA)=0.25 h) {[Benzyl(thiophene-2-sulfonyl)amino]methyl}-3'-(2-methoxy)ethoxy-biphenyl-2-sulfonic acid dimethylaminomethylenamide 900 mg of thiophene-2-sulfonic acid benzyl-[4-bromo-2-(2-methoxy)ethoxy-benzyl]amide, 1.4 g of dihydroxyboran-2-ylbenzenesulfonic acid dimethylaminomethylenamide, 47 mg of triphenylphosphine, 20 mg of Pd(II) acetate and 575 mg of $Na_2CO_3$ are suspended in 30 ml of toluene, 5 ml of water and 5 ml of EtOH. The mixture is refluxed for 6 h, then allowed to cool and diluted with 100 ml of EA. It is washed twice with 50 ml of a saturated aqueous NaCl solution each time. It is dried over magnesium sulfate and the solvent is removed in vacuo. Chromatography on silica gel using MTB yields 560 mg of a colorless, viscous oil.

$R_f$ (MTB)=0.13 MS (ES): 628 (M+H)$^+$ i) {[Benzyl(thiophene-2-sulfonyl)amino]methyl}-3'-(2-methoxy)ethoxy-biphenyl-2-sulfonamide 550 mg of {[benzyl(thiophene-2-sulfonyl)amino]methyl}-3'-(2-methoxy)ethoxy-biphenyl-2-sulfonic acid dimethylaminomethylenamide are refluxed for 1 h in 5 ml of EtOH and 5 ml of a saturated aqueous HCl solution. 100 ml of a 10% aqueous sodium hydrogencarbonate solution are added and the mixture is extracted 3 times with 100 ml of EA each time. It is dried over magnesium sulfate and the solvent is removed in vacuo. Chromatography on silica gel using MTB/DIP 1:1 yields 188 mg of a colorless oil.

$R_f$ (MTB/DIP 1:1)=0.33 MS (ES): 573 (M+H)$^+$ j) 4'-{[Benzyl(thiophene-2-sulfonyl)amino]methyl}-3'-(2-methoxy)ethoxy-biphenyl-2-sulfonylcyanamide 180 mg of {[benzyl(thiophene-2-sulfonyl)amino]methyl}-3'-(2-methoxy)ethoxy-biphenyl-2-sulfonamide, 63 μl of a 5 molar BrCN solution in acetonitrile and 131 mg of $K_2CO_3$ are suspended in 3 ml of acetonitrile (anhydrous) and refluxed for 2 h. The entire reaction mixture is allowed to cool and is chromatographed on silica gel using EA/MeOH 10:1 and 149 mg of an amorphous solid are obtained.

$R_f$ (EA/MeOH 10:1)=0.13 IR (CN): 2175.3 cm$^{-1}$ MS (FAB): 598 (M+H)$^+$

Residual activity of the NCBE at 10 μM: 30

Example 559

4'-{[Benzyl(thiophene-2-sulfonyl)amino]methyl}-3'-(2-methoxy)ethoxy-biphenyl-2-sulfonylcyanamide

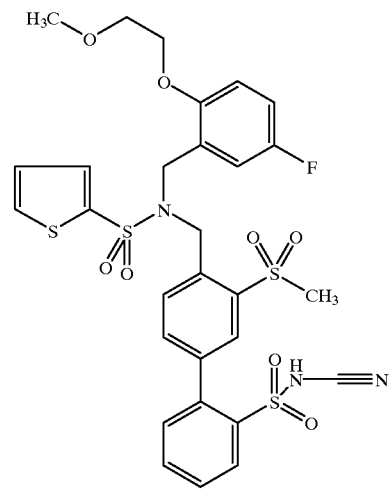

a) 4-Fluoro-1-(2-methoxyethoxy)-2-methylbenzene 10 g of 4-fluoro-2-methylphenol, 7.5 ml of 1-bromo-2-methoxyethane and 22 g of $K_2CO_3$ are suspended in 200 ml of DMF (anhydrous) and stirred at 120° C. for 12 h. The mixture is allowed to cool and the solvent is removed in vacuo. The residue is taken up using 400 ml of MTB and the solution is washed 3 times with 200 ml of a 10% aqueous NaOH solution each time and once with 100 ml of a saturated aqueous NaCl solution. It is dried over magnesium sulfate and the solvent is removed in vacuo. 10.4 g of a pale yellow oil are obtained.

$R_f$ (EA/HEP)=0.39 MS (DCI): 185 (M+H)$^+$ b) 2-Bromomethyl-4-fluoro-1-(2-methoxyethyoxy)benzene 10.4 g of 4-fluoro-1-(2-methoxyethoxy)-2-methylbenzene are dissolved in 100 ml of chlorobenzene and treated with a mixture of 10.1 g of NBS and 200 mg of benzoyl peroxide in portions at reflux temperature. The mixture is refluxed for 30 minutes. It is allowed to cool and is diluted with 300 ml of EA. It is then first washed once with 100 ml of a saturated aqueous $Na_2SO_3$ solution, then twice with 100 ml of a saturated aqueous sodium carbonate solution each time. It is dried over magnesium sulfate and the solvent is removed in vacuo. Chromatography on silica gel using EA/HEP 1:4 yields 5.2 g of a colorless oil.

$R_f$ (EA/HEP 1:4)=0.20 MS (DCI): 262 (M+H)$^+$ b1) 1-Bromo-4-bromomethyl-2-methanesulfonylbenzene 9.9 g of 1-bromo-2-methanesulfonyl-4-methylbenzene are taken up in 100 ml of chlorobenzene, 77 mg of benzoyl peroxide and 7.1 g of N-bromosuccinimide are added and the mixture is refluxed for 1 h. The solvent is then removed in vacuo, the residue is taken up in 100 ml of $CH_2Cl_2$ and the mixture is washed twice with 50 ml of a saturated aqueous $Na_2CO_3$ solution and once with 50 ml of water. It is dried over $Na_2SO_4$ and the solvent is removed in vacuo. The residue is recrystallized from 80 ml of HEP/30 ml of EA and 6.9 g of a pale yellow solid are obtained, mp 120–124° C.

$R_f$ (EA/HEP 1:2)=0.38 MS (DCI): 329 (M+H)$^+$ c) 2-(4-Bromo-2-methanesulfonylbenzyl)isoindole-1,3-dione 3.0 g of 4-bromo-1-bromomethyl-2-methanesulfonylbenzene and 2.0 g of potassium phthalimide are stirred at 100° C. for 1 h in 30 ml of anhydrous DMF. The mixture is allowed to cool, diluted with 200 ml of water and the suspension is stirred at RT for 30 minutes. The product is then filtered off and 1.8 g of a colorless solid are obtained, mp 188–190° C.

MS (ES): 393 (M+H)$^+$ d) 4-Bromo-2-methanesulfonylbenzylamine 1.8 g of 2-(4-Bromo-2-methanesulfonylbenzyl)isoindole-1,3-dione and 1.5 ml of hydrazine hydrate are first stirred at 60° C. for 1 h in 30 ml of EtOH, then refluxed for 4 h. The mixture is allowed to cool, the precipitate is filtered off and the volatile constituents of the filtrate are removed in vacuo. The residue is taken up using 100 ml of $CH_2Cl_2$ and solid constituents are again filtered off. The solvent of the filtrate is removed in vacuo and 1.3 g of a pale yellow oil are obtained.

$R_f$ (EA/MeOH 10:1)=0.10 MS (DCI): 264 (M+H)$^+$ e) (4-Bromo-2-methanesulfonylbenzyl)-[5-fluoro-2-(2-methoxyethoxy)benzyl]amine 1.3 g of 4-Bromo-2-methanesulfonylbenzylamine and 1.4 ml of triethylamine are dissolved in 20 ml of THF (anhydrous) and a solution of 1.3 g of 2-bromomethyl-4-fluoro-1-(2-methoxyethoxy)benzene in 5 ml of THF (anhydrous) is added dropwise at 0° C. The mixture is stirred at RT for 60 h, then diluted with 200 ml of EA and washed twice with 100 ml of a saturated aqueous $Na_2CO_3$ solution each time. It is dried over $MgSO_4$ and the solvent is removed in vacuo. Chromatography on silica gel using EA yields 910 mg of a colorless oil.

$R_f$ (EA)=0.43 MS (ES): 446 (M+H)$^+$

Further reaction is carried out analogously to Example 558 f)–j)

f) 4'-{[Benzyl(thiophen-2-sulfonyl)amino]methyl}-3'-(2-methoxy)ethoxy-biphenyl-2-sulfonylcyanamide $R_f$ (EA/MeOH 10:1)=0.33 IR (CN): 2174.3 cm$^{-1}$ MS (ES): 694 (M+H)$^+$ Residual activity of the NCBE at 10 μM: 12%

The title compound of Example 560 is synthesized analogously to Example 558:

Example 560

4'-{[Benzyl-2-(thiophen-2-yl)acetylamino]methyl}-3'-(2-methoxy)ethoxy-biphenyl-2-sulfonylcyanamide

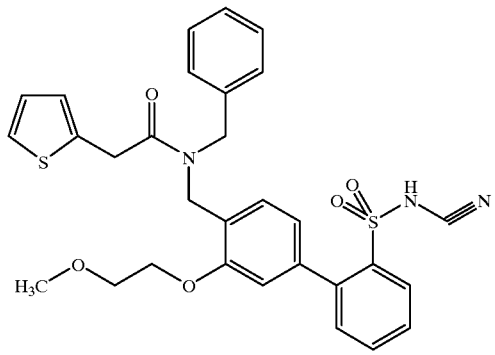

$R_f$(EA/MeOH 5:1)=0.36 IR (CN): 2175.0 cm$^{-1}$ MS (ES): 597 (M+H)$^+$ mp 95° C. (with decomposition). Residual activity of the NCBE at 10 μM: 8.0%.

Example 561

4'-{[Benzyl-2-(2-methylphenyl)acetylamino]methyl}biphenyl-2-sulfonylcyanamide

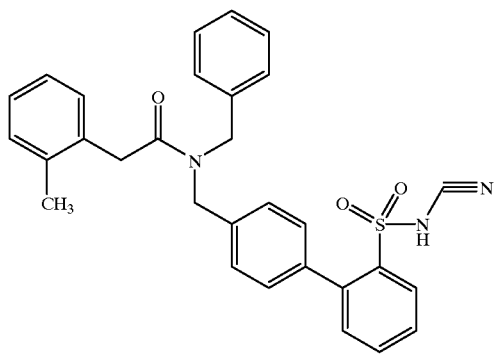

a) 4'-(Benzylaminomethyl)biphenyl-2-sulfonic acid (dimethylamino)methylenamide 4.4 ml of benzylamine are dissolved in 90 ml of THF (anhydrous) and 7.6 g of 4'-(bromomethyl)-N-[(dimethylamino)methylene]-(1,1'-biphenyl)2-sulfonamide (J. Med. Chem. 1995, 38, 2357) are added in portions at 0° C. The mixture is stirred at RT for 24 h, then diluted with 500 ml of EA and washed twice with 200 ml of a saturated aqueous $Na_2CO_3$ solution. It is dried over $Na_2SO_4$ and the solvent is removed in vacuo. Chromatography on silica gel using EA/MeOH 10:1 yields 3.8 g of a colorless oil.

$R_f$ (EA/MeOH 10:1)=0.25 MS (FAB): 408 $(M+H)^+$ b) o-Tolylacetyl chloride 4.8 g of o-tolylacetic acid are dissolved in 36 ml of $SOCl_2$ and refluxed for 12 h. The volatile constituents are then removed in vacuo and the residue is taken up 3 times in each case in 50 ml of toluene and the volatile constituents are removed in vacuo. 6.6 g of a pale yellow liquid are obtained, which is employed further without purification.

c) 4'-{[Benzyl-2-(2-methylphenyl)acetylamino]methyl}biphenyl-2-sulfonic acid (dimethylamino)methylenamide 408 mg of 4'-(benzylaminomethyl)biphenyl-2-sulfonic acid (dimethylamino)methylenamide are dissolved in 9 ml of $CH_2Cl_2$ (anhydrous) and first 162 µl of pyridine, then 220 mg of o-tolylacetyl chloride are added at RT. The mixture is stirred at RT for 24 h, diluted with 100 ml of $CH_2Cl_2$ and washed 3 times with 50 ml of a saturated aqueous $Na_2CO_3$ solution each time. It is dried over $Na_2SO_4$ and the solvent is removed in vacuo. Chromatography on silica gel using EA/HEP 2:1 yields 330 mg of a colorless oil.

$R_f$ (EA/HEP 2:1)=0.52 MS (FAB): 540 $(M+H)^+$ d) 4'-{[Benzyl-2-(2-methylphenyl)acetylamino]methyl}biphenyl-2-sulfonamide 320 mg of 4'-{[benzyl-2-(2-methylphenyl)acetylamino]methyl}biphenyl-2-sulfonic acid (dimethylamino)methylenamide are dissolved in 6 ml of MeOH and 3 ml of a saturated aqueous HCl solution are added at RT. The mixture is refluxed for 8 h and adjusted to pH=5–6 using a 6 N aqueous NaOH solution after cooling. It is diluted with 70 ml of water and extracted 3 times with 70 ml of EA each time. It is dried over $Na_2SO_4$ and the solvent is removed in vacuo. 300 mg of a colorless oil are obtained.

$R_f$ (EA)=0.68 MS (ES): 485 $(M+H)^+$ e) 4'-{[Benzyl-2-(2-methylphenyl)acetylamino]methyl}biphenyl-2-sulfonylcyanamide 280 mg of 4'-{[benzyl-2-(2-methylphenyl)acetylamino]methyl}biphenyl-2-sulfonamide and 245 mg of $K_2CO_3$ are dissolved in 6 ml of acetonitrile (anhydrous) and 116 µl of a 5 N solution of BrCN in acetonitrile are injected at RT. The entire reaction mixture is refluxed for 2 h and chromatographed on silica gel using EA/MeOH 10:1 after cooling. 130 mg of a colorless solid are obtained, mp 108° C. (with decomposition).

$R_f$ (EA/MeOH 10:1)=0.27 IR (CN): 2177.0 $cm^{-1}$ MS (FAB): 532 $(M+H)^+$

Residual activity of the NCBE at 10 µM: 16%

The title compounds of Examples 562 to 568 are synthesized analogously to Example 561:

Example 562

4'-{[Benzyl-2-(2-trifluoromethylphenyl)acetylamino]methyl}biphenyl-2-sulfonylcyanamide

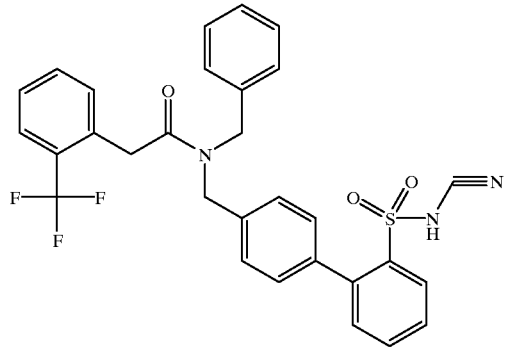

$R_f$ (EA/MeOH 10:1)=0.30 IR (CN): 2178.0 $cm^{-1}$ MS (FAB): 586 $(M+Na)^+$ mp 90° C. (with decomposition). Residual activity of the NCBE at 10 µM: 33%.

Example 563

4'-{[Benzyl-2-(2-trifluoromethoxyphenyl)acetylamino]methyl}biphenyl-2-sulfonylcyanamide

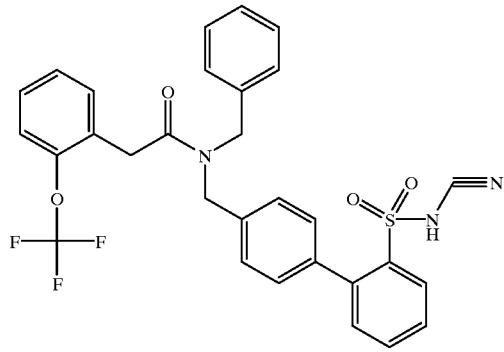

$R_f$ (EA/MeOH 10:1)=0.26 IR (CN): 2177.0 cm$^{-1}$ MS (ES): 580 (M+H)$^+$ mp 125° C. (with decomposition). Residual activity of the NCBE at 10 μM: 46%.

Example 564

4'-{[Benzyl-2-(2-trifluoromethoxyphenyl)acetylamino]methyl}biphenyl-2-sulfonylcyanamide

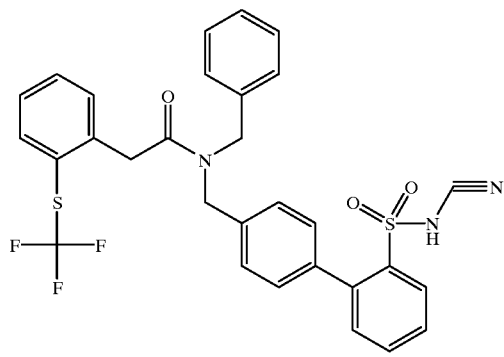

$R_f$ (EA/MeOH 10:1)=0.27 IR (CN): 2176.0 cm$^{-1}$ MS (ES): 596 (M+H)$^+$ mp 122° C. (with decomposition). Residual activity of the NCBE at 10 μM: 23%.

Example 565

4'-{[Benzyl-2-methylbenzoylamino]methyl}biphenyl-2-sulfonylcyanamide

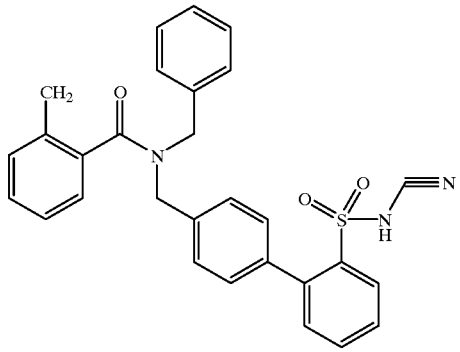

$R_f$ (EA/MeOH 10:1)=0.22 IR (CN): 2174.0 cm$^{-1}$ MS (ES): 496 (M+H)$^+$ mp 173° C. (with decomposition). Residual activity of the NCBE at 10 μM: 42%.

Example 566

4'-{[Benzyl-2-trifluoromethylbenzoylamino]methyl}biphenyl-2-sulfonylcyanamide

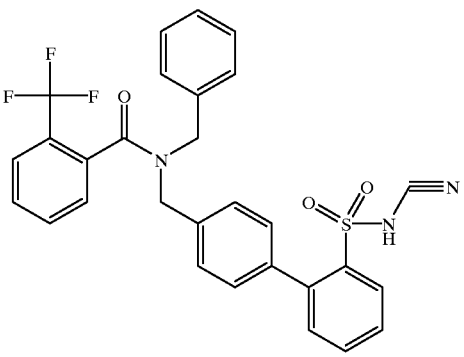

$R_f$ (EA/MeOH 10:1)=0.20 IR (CN): 2176.0 cm$^{-1}$ MS (ES): 550 (M+H)$^+$ mp 165° C. (with decomposition). Residual activity of the NCBE at 10 μM: 72%.

Example 567

4'-{[Benzyl-2-trifluoromethoxybenzoylamino]methyl}biphenyl-2-sulfonylcyanamide

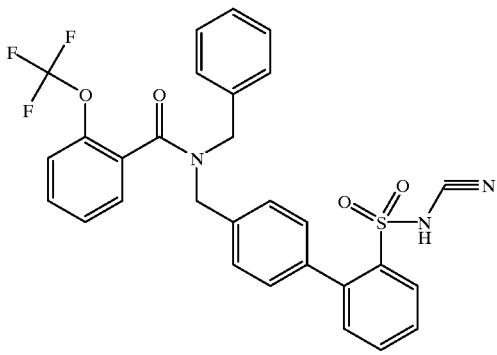

$R_f$ (EA/MeOH 10:1)=0.22 IR (CN): 2176.0 cm$^{-1}$ MS (ES): 566 (M+H)$^+$ mp 160° C. (with decomposition). Residual activity of the NCBE at 10 μM: 69%.

Example 568

4'-{[Benzyl-(5-methylthiophen-2-yl)carbonylamino]methyl}biphenyl-2-sulfonylcyanamide

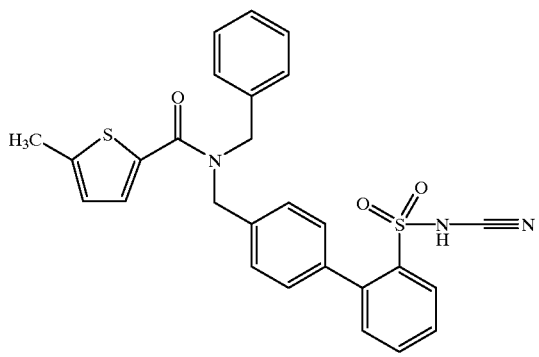

$R_f$ (EA/MeOH 10:1)=0.16 IR (CN): 2175.0 cm$^{-1}$ MS (FAB): 524 (M+Na)$^+$ mp 166° C. (with decomposition). Residual activity of the NCBE at 10 μM: 70%.

Pharmacological Data

Inhibition of the Na$^+$-dependent Cl$^-$/HCO$_3^-$ exchanger (NCBE) in human endothelial cells Human endothelial cells (ECV-304) were detached form culture flasks with the aid of trypsin/EDTA buffer (0.05/0.02% in phosphate buffer) and, after centrifugation (100 g, 5 min), taken up in a buffered saline solution (mmol/l: 115 NaCl, 20 NH$_4$Cl, 5 KCl, 1 CaCl$_2$, 1 MgSO$_4$, 20 N-(2-hydroxyethyl)-piperazine-N☐-2-ethanesulfonic acid (HEPES), 5 glucose and 1 g/l of bovine serum albumin; pH 7.4). This cell suspension was incubated at 37☐ C. for 20 min with 5 μM BCECF acetoxymethyl ester. The cells were then washed and resuspended in a sodium- and bicarbonate-free buffer solution (mmol/l: 5 HEPES, 133.8 choline chloride, 4.7 KCl, 1.25 MgCl$_2$, 0.97 K$_2$HPO$_4$, 0.23 KH$_2$PO$_4$, 5 glucose; pH 7.4).

For the subsequent fluorescence measurement in the FLIPR (Fluorescent Imaging Plate Reader), 100 μl of this cell suspension in each case containing 20,000 cells were added by pipette per well of a 96-well microtiter plate and this microtiter plate was centrifuged (100 g, 5 min). In the FLIPR, 100 μl of buffer solution in each case were then removed from a further prepared microtiter plate and added by pipette to each of the 96 wells of the measuring plate. In this case, for a 100% control, i.e. a recovery of the intracellular pH (pH$_i$) by means of the NCBE, a bicarbonate- and sodium-containing buffer solution (mmol/l: 5 HEPES, 93.8 NaCl, 40 NaHCO$_3$, 4.7 KCl, 1.25 CaCl$_2$, 1.25 MgCl$_2$, 0.97 Na$_2$HPO$_4$, 0.23 NaH$_2$PO$_4$, 5 glucose; pH 7.4) which contained 50 μM HOE 642 was used. For a 0% control, i.e. no pHi recovery at all, a bicarbonate-free, sodium-containing buffer solution (mmol/l: 5 HEPES, 133.8 NaCl, 4.7 KCl, 1.25 CaCl$_2$, 1.25 MgCl$_2$, 0.97 Na$_2$HPO$_4$, 0.23 NaH$_2$PO$_4$, 5 glucose; pH 7.4) to which 50 μM HOE 642 were also added was employed. The compounds according to the invention were added in various concentrations of the sodium- and bicarbonate-containing solution. After addition of the buffer solutions to the dye-loaded acidified cells situated in the measuring plate, the increase in the fluorescence intensity which corresponded to an increase in the pHi was determined in each well of the microtiter plate.

The kinetics were in this case recorded at 35° C. over a period of 2 minutes. The increase in the fluorescence intensities for different concentrations of the compounds according to the invention was related to the two controls and from this the inhibitory action of the substances was determined.

What is claimed is:

1. A compound of the formula (I),

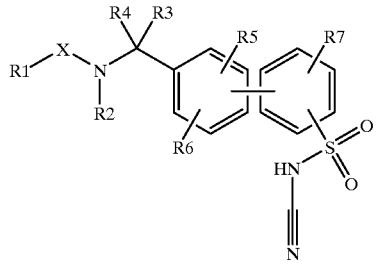

in which the symbols have the following meaning:

R(1) is
1. alkyl having 1, 2, 3, 4, 5, 6, 7 or 8 carbon atoms;
2. alkyl having 1, 2, 3, 4, 5, 6, 7 or 8 carbon atoms, in which one to all hydrogen atoms are replaced by fluorine;
3. alkenyl having 2, 3, 4, 5, 6, 7, 8, 9, 10, 11 or 12 carbon atoms;
4. —C$_n$H$_{2n-nn}$—Y,
   nn is zero or 2; and
   n is zero, 1, 2, 3 or 4; where n is unequal to zero or 1 if nn is equal to 2; or
5. —C$_n$H$_{2n-nn}$—Y,
   nn is zero or 2; and
   n is 1, 2, 3 or 4; where n is unequal to 1 if nn is equal to 2;
   where 1, 2 or 3 hydrogen atoms in the divalent radical —C$_n$H$_{2n-nn}$— independently of one another are replaced by a radical from the group consisting of
   1. aryl having 6, 7, 8, 9, 10, 11, 12, 13 or 14 carbon atoms;
   2. amino;
   3. NR(22)R(23);
   4. alkoxycarbonyl;

5. COOR(16);
6. alkyl having 1, 2, 3 or 4 carbon atoms; and
7. $(C_6-C_{14})$-aryl-$(C_1-C_4)$-alkylcarbonyl;

R(2) is
1. hydrogen;
2. alkyl having 1, 2, 3, 4, 5, 6, 7 or 8 carbon atoms;
3. alkyl having 1, 2, 3, 4, 5, 6, 7 or 8 carbon atoms, in which one to all hydrogen atoms are replaced by fluorine;
4. alkenyl having 2, 3, 4, 5, 6, 7, 8, 9, 10, 11 or 12 carbon atoms;
5. alkynyl having 2, 3, 4, 5, 6, 7 or 8 carbon atoms;
6. —$C_nH_{2n-nn}$—Z,
   nn is zero or 2; and
   n is zero, 1, 2, 3 or 4; where n is unequal to zero or 1 if nn is equal to 2; or
7. —$C_nH_{2n-nn}$—Z,
   nn is zero or 2; and
   n is 1, 2, 3 or 4, where n is unequal to 1 if nn is equal to 2;
   where 1, 2 or 3 hydrogen atoms in the divalent radical —$C_nH_{2n-nn}$— independently of one another are replaced by a radical from the group consisting of
       1. aryl having 6, 7, 8, 9, 10, 11, 12, 13 or 14 carbon atoms;
       2. amino;
       3. NR(22)R(23);
       4. $(C_1-C_4)$-alkoxycarbonyl;
       5. COOR(16); and
       6. alkyl having 1, 2, 3 or 4 carbon atoms;

R(3) and R(4) independently of one another are hydrogen or alkyl having 1, 2, 3, 4, 5, 6, 7 or 8 carbon atoms;

R(5), R(6) and R(7) independently of one another are hydrogen, alkyl having 1, 2, 3, 4, 5, 6, 7 or 8 carbon atoms, F, Cl, Br, I, $CF_3$,—CN, —$NO_2$, $SO_q$—R(8), CO—R(21) or O—R(10);

R(8) is alkyl having 1, 2, 3, 4, 5, 6, 7 or 8 carbon atoms, NR(11)R(12) or phenyl which is unsubstituted or is substituted by 1, 2 or 3 identical or different radicals from the group consisting of F, Cl, Br, I, $CF_3$, methyl, methoxy, hydroxyl and NR(11)R(12);

R(9) and R(21) independently of one another are hydrogen, alkyl having 1, 2, 3, 4, 5, 6, 7 or 8 carbon atoms or OR(13);

R(10) is hydrogen, alkyl having 1, 2, 3, 4, 5, 6, 7 or 8 carbon atoms which is unsubstituted or substituted by $(C_1-C_4)$-alkoxy; or phenyl which is unsubstituted or is substituted by 1, 2 or 3 identical or different radicals from the group consisting of F, Cl, Br, I, $CF_3$, methyl, methoxy, hydroxyl and NR(11)R(12);

R(11), R(12), R(19) and R(20) independently of one another are hydrogen, alkyl having 1, 2, 3 or 4 carbon atoms or $(C_1-C_4)$-alkanoyl;

R(13) is hydrogen or alkyl having 1, 2, 3, 4, 5, 6, 7 or 8 carbon atoms;

X is carbonyl, —CO—NH—, —CO—CO— or sulfonyl;

Y and Z independently of one another are
1. aryl having 6, 7, 8, 9, 10, 11, 12, 13 or 14 carbon atoms;
2. a radical as defined in 1., which is substituted by 1, 2, 3, 4 or 5 identical or different radicals from the group consisting of alkyl having 1, 2, 3, 4, 5, 6, 7 or 8 carbon atoms, aryl having 6, 7, 8, 9, 10, 11, 12, 13 or 14 carbon atoms, F, Cl, Br, I, $CF_3$, $SO_qR(18)$, OR(16), NR(19)R(20), —CN, $NO_2$ and CO—R(9); or where two radicals together form a fused heterocyclyl radical;
3. heteroaryl having 1, 2, 3, 4, 5, 6, 7, 8 or 9 carbon atoms;
4. a radical as defined in 3., which is substituted by 1, 2 or 3 identical or different radicals from the group consisting of F, Cl, Br, I, $CF_3$, $CH_3$, methoxy, hydroxyl and NR(11)R(12);
5. cycloalkyl having 3, 4, 5, 6, 7, 8, 9 or 10 carbon atoms;
6. a radical as defined in 5., substituted by aryl having 6, 7, 8, 9, 10, 11, 12, 13 or 14 carbon atoms;
7. O—R(14);
8. O—R(17);
9. —$SO_2$—R(14);
10. arylalkylcarbonyl; or
11. heterocyclyl;

R(14) and R(17) independently of one another are
1. hydrogen;
2. alkyl having 1, 2, 3, 4, 5, 6, 7 or 8 carbon atoms;
3. alkenyl having 2, 3, 4, 5, 6, 7, 8, 9, 10, 11 or 12 carbon atoms;
4. —$C_nH_{2n-nn}$-phenyl,
   nn is zero or 2; and
   n is zero, 1, 2, 3 or 4; where n is unequal to zero or 1 if nn is equal to 2; or
5. a radical as defined in 4., where the phenyl group is substituted by 1, 2 or 3 identical or different radicals from the group consisting of alkyl having 1, 2, 3, 4, 5, 6, 7 or 8 carbon atoms, F, Cl, Br, I, $CF_3$, $SO_qR(15)$, OR(16), NR(11)R(12), —CN, —$NO_2$ and CO—R(9);

R(15) and R(18) independently of one another are alkyl having 1, 2, 3 or 4 carbon atoms, alkyl having 1, 2, 3 or 4 carbon atoms, in which one to all hydrogen atoms are replaced by fluorine, or NR(11)R(12);

R(16) is
1. hydrogen,
2. alkyl having 1, 2, 3 or 4 carbon atoms,
3. alkyl having 1, 2, 3 or 4 carbon atoms, substituted by $(C_1-C_4)$-alkoxy,
4. alkyl having 1, 2, 3 or 4 carbon atoms, in which one to all hydrogen atoms are replaced by fluorine;
5. aryl having 6, 7, 8, 9, 10, 11, 12, 13 or 14 carbon atoms; or
6. a radical as defined in 5., which is substituted by 1, 2 or 3 identical or different radicals from the group consisting of F, Cl, Br, I, $CF_3$, NR(19)R(20), —CN, and $NO_2$;

R(22) and R(23) independently of one another are hydrogen or CO—OR(24);

R(24) is hydrogen, alkyl having 1, 2, 3, 4, 5, 6, 7 or 8 carbon atoms or —$C_nH_{2n}$-phenyl where n is equal to 1, 2, 3 or 4; and q independently of one another is zero, 1 or 2;

or a physiologically tolerable salt thereof.

2. A compound as claimed in claim 1, in which:

R(1) is
1. alkyl having 1, 2, 3, 4 or 5 carbon atoms;
2. alkyl having 1, 2, 3, 4 or 5 carbon atoms, in which one to all hydrogen atoms are replaced by fluorine;
3. alkenyl having 2, 3, 4, 5, 6, 7, 8, 9, 10, 11 or 12 carbon atoms;
4. —$C_nH_{2n-nn}$—Y,
   nn is zero or 2; and
   n is zero, 1, 2, 3 or 4; where n is unequal to zero or 1 if nn is equal to 2; or 5. —$C_nH_{2n-nn}$—Y,
  nn is zero or 2; and
  n is 1, 2, 3 or 4; where n is unequal to 1 if nn is equal to 2;
    where 1, 2 or 3 hydrogen atoms in the divalent radical —$C_nH_{2n-nn}$— independently of one another are replaced by a radical from the group consisting of
    1. aryl having 6, 7, 8, 9, 10, 11, 12, 13 or 14 carbon atoms;
    2. amino;
    3. NR(22)R(23);
    4. alkoxycarbonyl;
    5. COOR(16);
    6. alkyl having 1, 2, 3 or 4 carbon atoms; and
    7. ($C_6$–$C_{14}$)-aryl-($C_1$–$C_4$)-alkylcarbonyl;

R(2) is
1. hydrogen;
2. alkyl having 1, 2, 3, 4, or 5 carbon atoms;
3. alkyl having 1, 2, 3, 4, or 5 carbon atoms, in which one to all hydrogen atoms are replaced by fluorine;
4. alkenyl having 2, 3, 4, 5, 6, 7, 8, 9, 10, 11 or 12 carbon atoms;
5. alkynyl having 2, 3, 4, or 5 carbon atoms;
6. —$C_nH_{2n-nn}$—Z,
  nn is zero or 2; and
  n is zero, 1, 2, 3 or 4; where n is unequal to zero or 1 if nn is equal to 2; or
7. —$C_nH_{2n-nn}$—Z,
  nn is zero or 2; and
  n is 1, 2, 3 or 4, where n is unequal to 1 if nn is equal to 2;
    where 1, 2 or 3 hydrogen atoms in the divalent radical —$C_nH_{2n-nn}$— independently of one another are replaced by a radical from the group consisting of
    1 aryl having 6, 7, 8, 9, 10, 11, 12, 13 or 14 carbon atoms;
    2. amino;
    3. NR(22)R(23);
    4. ($C_1$–$C_4$)-alkoxycarbonyl;
    5. COOR(16); and
    6. alkyl having 1, 2, 3 or 4 carbon atoms;

R(3) and R(4) independently of one another are hydrogen or alkyl having 1, 2, 3 or 4 carbon atoms;
R(5), R(6) and R(7) independently of one another are hydrogen, alkyl having 1, 2, 3 or 4 carbon atoms, F, Cl, Br, $CF_3$, —CN, $SO_q$—R(8), CO—R(21) or O—R(10);
R(8) is alkyl having 1, 2, 3 or 4 carbon atoms, NR(11)R(12) or phenyl which is unsubstituted or is substituted by 1 or 2 identical or different radicals from the group consisting of F, Cl, Br, $CF_3$, methyl, methoxy, hydroxyl and NR(11)R(12);
R(9) and R(21) independently of one another are hydrogen, alkyl having 1, 2, 3 or 4 carbon atoms or OR(13);
R(10) is hydrogen, alkyl having 1, 2, 3 or 4 carbon atoms which is unsubstituted or substituted by ($C_1$–$C_4$)-alkoxy; or phenyl which is unsubstituted or is substituted by 1 or 2 identical or different radicals from the group consisting of F, Cl, Br, $CF_3$, methyl, methoxy, hydroxyl and NR(11)R(12);
R(11), R(12), R(19) and R(20) independently of one another are hydrogen, alkyl having 1, 2, 3 or 4 carbon atoms or ($C_1$–$C_4$)-alkanoyl;
R(13) is hydrogen or alkyl having 1, 2, 3 or 4 carbon atoms;
X is carbonyl, —CO—NH—, —CO—CO— or sulfonyl;
Y and Z independently of one another are
1. phenyl, 1-naphthyl or 2-naphthyl;
2. a radical as defined in 1., which is substituted by 1, 2, 3, 4 or 5 identical or different radicals from the group consisting of alkyl having 1, 2, 3 or 4 carbon atoms, phenyl, 1-naphthyl or 2-naphthyl, F, Cl, Br, $CF_3$, $SO_q$R(18), OR(16), NR(19)R(20), —CN and CO—R(9); or where two radicals together form a fused heterocyclyl radical;
3. heteroaryl having 1, 2, 3, 4, 5, 6, 7, 8 or 9 carbon atoms;
4. a radical as defined in 3., which is substituted by 1 or 2 identical or different radicals from the group consisting of F, Cl, Br, $CF_3$, $CH_3$, methoxy, hydroxyl and NR(11)R(12);
5. cycloalkyl having 3, 4, 5, 6, 7, 8, 9 or 10 carbon atoms;
6. a radical as defined in 5., substituted by phenyl, 1-naphthyl or 2-naphthyl;
7. O—R(14);
8. O—R(17);
9. —$SO_2$—R(14);
10. arylalkylcarbonyl; or
11. heterocyclyl;

R(14) and R(17) independently of one another are
1. hydrogen;
2. alkyl having 1, 2, 3 or 4 carbon atoms;
3. alkenyl having 2, 3, 4, 5 or 6 carbon atoms;
4. —$C_nH_{2n-nn}$-phenyl,
  nn is zero or 2; and
  n is zero, 1, 2, 3 or 4; where n is unequal to zero or 1 if nn is equal to 2; or
5. a radical as defined in 4., where the phenyl group is substituted by 1, 2 or 3 identical or different radicals from the group consisting of alkyl having 1, 2, 3 or 4 carbon atoms, F, Cl, Br, $CF_3$, $SO_q$R(15), OR(16), NR(11)R(12), —CN, and CO—R(9);

R(15) and R(18) independently of one another are alkyl having 1, 2, 3 or 4 carbon atoms, alkyl having 1, 2, 3 or 4 carbon atoms, in which one to all hydrogen atoms are replaced by fluorine, or NR(11)(R(12);

R(16) is
1. hydrogen,
2. alkyl having 1, 2, 3 or 4 carbon atoms,
3. alkyl having 1, 2, 3 or 4 carbon atoms substituted by ($C_1$–$C_4$)-alkoxy,
4. alkyl having 1, 2, 3 or 4 carbon atoms, in which one to all hydrogen atoms are replaced by fluorine;
5. phenyl, 1-naphthyl or 2-naphthyl; or
6. a radical as defined in 5., which is substituted by 1, 2 or 3 identical or different radicals from the group consisting of F, Cl, Br, $CF_3$, NR(19)R(20), and —CN;

R(22) and R(23) independently of one another are hydrogen or CO—OR(24);
R(24) is hydrogen, alkyl having 1, 2, 3 or 4 carbon atoms or —$C_nH_{2n}$-phenyl where n is equal to 1, 2 or 3; and
q independently of one another is zero, 1 or 2.

3. A compound as claimed in claim 1, in which:
R(1) is
1. alkyl having 1, 2, 3, 4 or 5 carbon atoms,
2. alkenyl having 2, 3 or 4 carbon atoms, 3. —$C_nH_{2n-nn}$—Y;
   Y is
   1. phenyl;
   2. a radical as defined in 1., which is substituted by 1, 2, 3, 4 or 5 identical or different radicals from the group consisting of alkyl having 1, 2, 3 or 4 carbon atoms, F, Cl, Br, cyano, $CF_3$, hydroxyl, $NO_2$, $SO_2R(18)$, OR(16), $SCF_3$, NR(19)R(20), and CO—R(9);
   3. OR(14),
   4. $SO_2$—R(14);
   5. 1-naphthyl or 2-naphthyl;
   6. a radical as defined in 5., which is substituted by a radical from the group consisting of alkyl having 1, 2, 3 or 4 carbon atoms, F, Cl, $CF_3$, $SO_2R(18)$, OR(16), NR(19)R(20) and CO—R(9);
   7. heteroaryl having 1, 2, 3, 4, 5, 6, 7, 8 or 9 carbon atoms;
   8. a radical as defined in 3., which is substituted by a radical from the group consisting of F, Cl, $CF_3$, $CH_3$, methoxy and $N(CH_3)_2$; or
   9. cycloalkyl having 3, 4, 5, 6 or 7 carbon atoms;
   nn is zero or 2; and
   n is zero, 1, 2, 3 or 4, where n is unequal to zero or 1 if nn is equal to 2; or
4. —$C_nH_{2n-nn}$—Y,
   Y is
   1. phenyl;
   2. OR(14); or
   3. heteroaryl;
   nn is zero or 2; and
   n is 1, 2 or 3, where n is unequal to 1 if nn is equal to 2; in which 1, 2 or 3 hydrogen atoms in the divalent radical —$C_nH_{2n-nn}$— independently of one another are replaced by a radical from the group consisting of
   1. aryl having 6, 7, 8, 9, 10, 11, 12, 13 or 14 carbon atoms, or phenylacetyl;
   2. amino;
   3. NR(22)R(23); and
   4. alkyl having 1, 2, 3 or 4 carbon atoms;
R(2) is
1. hydrogen
2. alkyl having 1, 2, 3, 4 or 5 carbon atoms;
3. alkyl having 1, 2, 3, 4 or 5 carbon atoms, in which one to all hydrogen atoms are replaced by fluorine;
4. alkenyl having 2, 3, 4, 5, 6, 7, 8, 9 or 10 carbon atoms;
5. alkynyl having 2, 3, 4 or 5 carbon atoms,
6. —$C_nH_{2n-nn}$—Z;
   Z is
   1. phenyl;
   2. a radical as defined in 1., which is substituted by 1, 2 or 3 identical or different radicals from the group consisting of alkyl having 1, 2, 3 or 4 carbon atoms, phenyl, F, Cl, Br, $CF_3$, $SO_2R(18)$, OR(16), nitro, cyano, NR(19)R(20), and CO—R(9), or where two radicals together form a methylenedioxy radical;
   3. 1-naphthyl, or2-naphthyl;
   4. a radical as defined in 3., which is substituted by a radical from the group consisting of alkyl having 1, 2, 3 or 4 carbon atoms, F, Cl, $CF_3$, $SO_2R(18)$, OR(16), nitro, cyano, NR(19)R(20) and CO—R(9);
   5. heteroaryl having 1, 2, 3, 4, 5, 6, 7, 8 or 9 carbon atoms;
   6. a radical as defined in 5., which is substituted by a radical from the group consisting of F, Cl, $CF_3$, $CH_3$, methoxy, hydroxyl and $N(CH_3)_2$;
   7. cycloalkyl having 3, 4, 5, 6, 7, 8, 9 or 10 carbon atoms; or
   8. a radical as defined in 7., which is substituted by phenyl;
   nn is zero or 2; and
   n is zero, 1, 2 or 3, where n is unequal to zero or 1 if nn is equal to 2;
7. —$C_nH_{2n-nn}$—Z,
   Z is
   1. phenyl; or
   2. a radical as defined in 1., which is substituted by 1, 2 or 3 identical or different radicals from the group consisting of alkyl having 1, 2, 3 or 4 carbon atoms, phenyl, F, Cl, $CF_3$, $SO_2R(18)$,—OR(16), nitro, cyano, NR(19)R(20) and CO—R(9);
   nn is zero or 2; and
   n is 1, 2 or 3, where n is unequal to 1 if nn is equal to 2; where 1, 2 or 3 hydrogen atoms in the divalent radical —$C_nH_{2n-nn}$— independently of one another are replaced by a radical from the group consisting of
   1. ($C_1$–$C_4$)-alkoxycarbonyl;
   2. COOR(16); and
   3. alkyl having 1, 2, 3 or 4 carbon atoms; or
8. —$C_nH_{2n}$—OR(17);
   n is zero, 1, 2 or 3;
R(3) and R(4) are hydrogen or methyl;
R(5), R(6) and R(7) independently of one another are hydrogen, alkyl having 1, 2, 3 or 4 carbon atoms, F, Cl, $CF_3$, CN, $SO_2$—R(8), CO—R(21) or O—R(10);
R(8) is alkyl having 1, 2, 3 or 4 carbon atoms, $N(CH_3)_2$ or phenyl which is unsubstituted or is substituted by a radical from the group consisting of F, Cl, $CF_3$, methyl, methoxy, hydroxyl and $N(CH_3)_2$;
R(9) and R(21) independently of one another are hydrogen, methyl or OR(13);
R(10) is hydrogen, alkyl having 1, 2, 3 or 4 carbon atoms, which is unsubstituted or substituted by ($C_1$–$C_4$)-alkoxy, or phenyl which is unsubstituted or is substituted by a radical from the group consisting of F, Cl, $CF_3$, methyl, methoxy and $N(CH_3)_2$;
R(11) and R(12) independently of one another are hydrogen, alkyl having 1, 2, 3 or 4 carbon atoms or ($C_1$–$C_4$)-alkanoyl;
R(13) is hydrogen or alkyl having 1, 2, 3 or 4 carbon atoms;
X is carbonyl, —CO—CO—, —NH—CO— or sulfonyl;
R(14) is
1. hydrogen;
2. alkyl having 1, 2, 3 or 4 carbon atoms;
3. alkenyl having 2, 3, 4, 5 or 6 carbon atoms;
4. —$C_nH_{2n-nn}$-phenyl,
   nn is zero or 2; and
   n is zero, 1, 2, 3 or 4; where n is unequal to zero or 1 if nn is equal to 2; or
5. a radical as defined in 4., where the phenyl group is substituted by 1, 2, or 3 identical or different radicals from the group consisting of alkyl having 1, 2, 3 or 4 carbon atoms, F, Cl, Br, $CF_3$, $SO_qR(15)$, OR(16), NR(11)R(12), —CN, and CO—R(9);
R(15) is alkyl having 1, 2, 3 or 4 carbon atoms or $N(CH_3)_2$;
R(16) is
1. hydrogen,
2. alkyl having 1, 2, 3 or 4 carbon atoms,
3. alkyl having 1, 2, 3 or 4 carbon atoms substituted by ($C_1$–$C_4$)-alkoxy,
4. alkyl having 1, 2, 3 or 4 carbon atoms, in which one to all hydrogen atoms are replaced by fluorine;

5. phenyl, 1-naphthyl or 2-naphthyl; or
6. a radical as defined in 5., which is substituted by 1, 2 or 3 identical or different radicals from the group consisting of F, Cl, Br, $CF_3$, NR(19)R(20), and —CN;

R(17) is
1. hydrogen;
2. alkyl having 1, 2, 3 or 4 carbon atoms;
3. alkenyl having 2, 3, or 4 carbon atoms;
4. —$C_nH_{2n-nn}$-phenyl,
   nn is zero or 2; and
   n is zero, 1, 2, 3 or 4; where n is unequal to zero or 1 if nn is equal to 2; or
5. a radical as defined in 4., where the phenyl group is substituted by a radical from the group consisting of alkyl having 1, 2, 3 or 4 carbon atoms, F, Cl, Br, $CF_3$, $SO_qR(15)$, OR(16), NR(11)R(12), —CN, and CO—R(9);

R(18) is alkyl having 1, 2, 3 or 4 carbon atoms, alkyl having 1, 2, 3 or 4 carbon atoms, in which one to all hydrogen atoms are replaced by fluorine, or NR(11)R(12);

R(19) and R(20) independently of one another are hydrogen, alkyl having 1, 2, 3 or 4 carbon atoms or $(C_1-C_4)$-alkanoyl;

R(22) and R(23) independently of one another are hydrogen or CO—OR(24);

R(24) is hydrogen, alkyl having 1, 2, 3 or 4 carbon atoms or —Cn—$H_{2n}$-phenyl where n is equal to 1 or 2; and q independently of one another is zero, 1 or 2.

4. A compound as claimed in claim 1, in which:

R(1) is
1. alkyl having 1, 2, 3, 4 or 5 carbon atoms,
2. alkenyl having 2, 3 or 4 carbon atoms,
3. —$C_nH_{2n-nn}$—Y:
   Y is
   1. phenyl;
   2. a radical as defined in 1., which is substituted by 1, 2, 3, 4 or 5 identical or different radicals from the group consisting of alkyl having 1, 2, 3 or 4 carbon atoms, F, Cl, Br, cyano, $CF_3$, hydroxyl, $NO_2$, $SO_2R(18)$, $OCH_3$, $OCF_3$, $SCF_3$, $N(CH_3)_2$, NH—CO—$CH_3$, CO—R(9), phenoxy and phenoxy, mono- or polysubstituted by halogen;
   3. OR(14), or
   4. $SO_2$—R(14);
   nn is zero or 2; and
   n is zero, 1, 2, 3 or 4, where n is unequal to zero or 1 if nn is equal to 2;
4. —$C_nH_{2n-nn}$—Y,
   Y is
   1. phenyl;
   2. OR(14); or
   3. heteroaryl;
   nn is zero or 2; and
   n is 1, 2 or 3, where n is unequal to 1 if nn is equal to 2; in which 1, 2 or 3 hydrogen atoms in the divalent radical —$C_nH_{2n-nn}$— independently of one another are replaced by a radical from the group consisting of
   1. aryl having 6, 7, 8, 9, 10, 11, 12, 13 or 14 carbon atoms; or phenylacetyl;
   2. amino;
   3. NR(22)R(23); and
   4. alkyl having 1, 2, 3 or 4 carbon atoms;
5. —$C_nH_{2n}$—Y;
   Y is
   1. 1-naphthyl or 2-naphthyl;
   2. a radical as defined in 1., which is substituted by a radical from the group consisting of alkyl having 1, 2, 3 or 4 carbon atoms, F, Cl, $CF_3$, $SO_2R(18)$, $OCH_3$, $N(CH_3)_2$ and CO—R(9);
   3. heteroaryl having 1, 2, 3, 4, 5, 6, 7, 8 or 9 carbon atoms;
   4. a radical as defined in 3., which is substituted by a radical from the group consisting of F, Cl, $CF_3$, $CH_3$, methoxy and $N(CH_3)_2$; or
   5. cycloalkyl having 3, 4, 5, 6 or 7 carbon atoms;
   n is zero, 1, 2, 3 or 4; or
6. —$C_nH_{2n}$—OR(14);
   n is zero 1 or 2;

R(2) is
1. alkyl having 1, 2, 3, 4 or 5 carbon atoms;
2. alkyl having 1, 2, 3, 4 or 5 carbon atoms, in which one to all hydrogen atoms are replaced by fluorine;
3. alkenyl having 2, 3, 4, 5, 6, 7, 8, 9 or 10 carbon atoms;
4. alkynyl having 2, 3, 4 or 5 carbon atoms
5. —$C_nH_{2n-nn}$—Z;
   Z is
   1. phenyl; or
   2. a radical as defined in 1., which is substituted by 1, 2 or 3 identical or different radicals from the group consisting of alkyl having 1, 2, 3 or 4 carbon atoms, phenyl, F, Cl, Br, $CF_3$, $SO_2R(18)$, —$OCH_3$, —$O(C_2H_4)OCH_3$, ethoxy, hydroxyl, nitro, cyano, $N(CH_3)_2$, —NH—CO—$CH_3$, CO—R(9), phenoxy and phenoxy, monosubstituted or polysubstituted by halogen; or where two radicals together form a methylenedioxy radical;
   nn is zero or 2; and
   n is zero, 1, 2 or 3, where n is unequal to zero or 1 if nn is equal to 2;
6. —$C_nH_{2n-nn}$—Z,
   Z is
   1. phenyl; or
   2. a radical as defined in 1., which is substituted by 1, 2 or 3 identical or different radicals from the group consisting of alkyl having 1, 2, 3 or 4 carbon atoms, phenyl, F, Cl, $CF_3$, $SO_2R(18)$, —$OCH_3$, —$O(C_2H_4)OCH_3$, ethoxy, hydroxyl, nitro, cyano, $N(CH_3)_2$ and CO—R(9);
   nn is zero or 2, and
   n is 1, 2 or 3, where n is unequal to 1 if nn is equal to 2;
   where 1, 2 or 3 hydrogen atoms in the divalent radical —$C_nH_{2n-nn}$— independently of one another are replaced by a radical from the group consisting of
   1. $(C_1-C_4)$-alkoxycarbonyl;
   2. COOR(16); and
   3. alkyl having 1, 2, 3 or 4 carbon atoms;
7. —$C_nH_{2n}$—Z;
   Z is
   1. 1-naphthyl, or 2-naphthyl;
   2. a radical as defined in 1., which is substituted by a radical from the group consisting of alkyl having 1, 2, 3 or 4 carbon atoms, F, Cl, $CF_3$, $SO_2R(18)$, $OCH_3$, —$O(C_2H_4)OCH_3$, ethoxy, hydroxyl, nitro, cyano, $N(CH_3)_2$, —$NHCOCH_3$ and CO—R(9);
   3. heteroaryl having 1, 2, 3, 4, 5, 6, 7, 8 or 9 carbon atoms;
   4. a radical as defined in 3., which is substituted by a radical from the group consisting of F, Cl, $CF_3$, $CH_3$, methoxy, hydroxyl and $N(CH_3)_2$;

5. cycloalkyl having 3, 4, 5, 6, 7, 8, 9 or 10 carbon atoms; or;
6. a radical as defined in 5., which is substituted by phenyl;
n is zero, 1, 2 or 3; or
8. —$C_nH_{2n}$—OR(17);
n is 2 or 3;
R(3) and R(4) are hydrogen;
R(5), R(6) and R(7) independently of one another are hydrogen, alkyl having 1, 2, 3 or 4 carbon atoms, F, Cl, $CF_3$, $SO_2$—R(8), CO—R(21) or O—R(10);
R(8) is methyl or $N(CH_3)_2$;
R(9) and R(21) independently of one another are hydrogen, methyl or OR(13);
R(10) is hydrogen, methyl or ethyl, which is unsubstituted or substituted by methoxy, or phenyl which is unsubstituted or is substituted by a radical from the group consisting of F, Cl, $CF_3$, methyl, methoxy and $N(CH_3)_2$;
R(13) is hydrogen or alkyl having 1, 2, 3 or 4 carbon atoms;
X is carbonyl, —CO—CO—, —NH—CO— or sulfonyl;
R(14) is
1. hydrogen;
2. methyl or ethyl;
3. alkenyl having 2, 3, 4, 5 or 6 carbon atoms;
4. —$C_nH_{2n}$-phenyl where n is equal to zero or 1;
5. a radical as defined in 4., where the phenyl group is substituted by a radical from the group consisting of alkyl having 1, 2, 3 or 4 carbon atoms, F, Cl, $CF_3$, $SO_2R(15)$, $OCH_3$, $N(CH_3)_2$ and CO—R(9); or
6. alkenyl having 2, 3 or 4 carbon atoms;
R(15) is methyl or $N(CH_3)_2$;
R(16) is hydrogen or alkyl having 1, 2, 3, or 4 carbon atoms;
R(17) is
1. hydrogen;
2. methyl;
3. —$C_nH_{2n}$-pnenyl where n is equal to zero or 1;
4. a radical as defined in 3., where the phenyl group is substituted by a radical from the group consisting of alkyl having 1, 2, 3 or 4 carbon atoms, F, Cl, $CF_3$, $SO_2R(15)$, $OCH_3$, $N(CH_3)_2$ and CO—R(9); or
5. alkenyl having 2, 3 or 4 carbon atoms;
R(18) is methyl, $CF_3$, amino or $N(CH_3)_2$;
R(22) and R(23) independently of one another are hydrogen or CO—OR(24); and
R(24) is hydrogen, alkyl having 1, 2, 3 or 4 carbon atoms or —$C_nH_{2n}$-phenyl where n is equal to 1 or 2.
5. A compound as claimed in claim 1, which is a compound of the formula Ia,

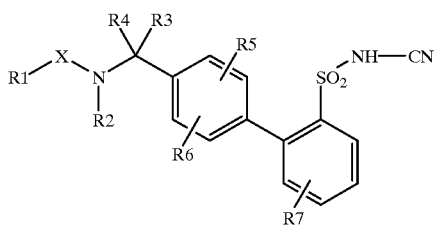

in which the radicals X and R(1) to R(7) have the meaning mentioned in claim 1.
6. A compound as claimed in claim 4, wherein R(1) is —$C_nH_{2n-nn}$—Y, and Y is thienyl.
7. A compound as claimed in claim 4, wherein R(1) is —$C_nH_{2n}$—Y, and Y is thienyl, benzothiophenyl, indolyl, or furyl.

8. A compound as claimed in claim 4, wherein R(2) is —$C_nH_{2n}$—Z, and Z is benzimadozolyl, pyridyl, thienyl, furyl, tetrahydrofuryl, pyrrolidinyl, pyrrolidine-1-carbonyl-4,5-dihydroisoxazolyl, benzofuranyl, or quinazolinyl.
9. A compound as claimed in claim 4, wherein R(2) is —$C_nH_{2n}$—Z, and Z is 1,3-dihydro1-oxobenzo[c]furanyl or 3,4-dihydroquinazolinyl.
10. A compound as claimed in claim 4, wherein R(2) is —$C_nH_{2n}$—Z, and Z is cyclopropyl, cyclopentyl, cyclohexyl, 1,2,3,4-tetrahydronaphthyl, or indanyl.
11. A compound as claimed in claim 4, wherein R(2) is —$C_nH_{2n}Z$, and Z is phenylcyclopentyl.
12. A compound as claimed in claim 4, wherein R(14) is allyl.
13. A pharmaceutical preparation, which comprises an effective amount of a compound as claimed in claim 4 and a carrier.
14. A pharmaceutical preparation as claimed in claim 13, which further comprises an effective amount of an NHE inhibitor or another active substance from another class of cardiovascular active compounds.
15. A method for inhibiting the sodium-dependent bicarbonate/chloride exchanger, which comprises administering to a host in need of the inhibition an effective amount of a compound as claimed in claim 1.
16. A method for the treatment of cardiac infarct, which comprises administering to a host in need of the treatment an effective amount of a compound as claimed in claim 1.
17. A method for the treatment of angina pectoris, which comprises administering to a host in need of the treatment an effective amount of a compound as claimed in claim 1.
18. A method for the treatment of an illness caused by an ischemic condition, which comprises administering to a host in need of the treatment an effective amount of a compound as claimed in claim 1.
19. A method for the treatment of an ischemic condition of the heart, which comprises administering to a host in need of the treatment an effective amount of a compound as claimed in claim 1.
20. A method for the treatment of an ischemic condition of the peripheral or central nervous system or of stroke, which comprises administering to a host in need of the treatment an effective amount of a compound as claimed in claim 1.
21. A method for the treatment of an ischemic condition of a peripheral organ or limb, which comprises administering to a host in need of the treatment an effective amount of a compound as claimed in claim 1.
22. A method for the treatment of a state of shock, which comprises administering to a host in need of the treatment an effective amount of a compound as claimed in claim 1.
23. A method for the preservation or storage of a transplant, which comprises contacting the transplant with an effective amount of a compound as claimed in claim 1.
24. A method for the treatment of cancer, which comprises administering to a host in need of the treatment a compound as claimed in claim 1.
25. A pharmaceutical preparation as claimed in claim 13, which further comprises an effective amount of an NHE inhibitor and another active substance from another class of cardiovascular active compounds.
26. A compound as claimed in claim 1, in which:
R(1) is $CH_3$—$CH_2$—$CH_2$—, Cyclohexyl-$CH_2$—$CH_2$—, Cyclohexyl-, 3-Methoxy-phenyl-$CH_2$—, 2-Methylphenyl-$CH_2$—, 2-Methylphenyl, 2-Thienyl-$CH_2$—, 4-t-Butyl-phenyl-, 2-Fluoro-phenyl-, Allyl-O—, 3,4,5-Trimethoxy-phenyl-, 2-Chloro-phenyl-, Phenyl-, CH₃—, E—CH₃—CH=CH—, CH₃—(CH₂)₃—, Phenyl-CH₂—CH₂—, 4-Methyl-phenyl-, Benzo[b]thiophen-2-yl-, Thien-2-yl-, (Phenyl)CH₂—, Phenyl-CH₂—CO—CH(Phenyl)-, (4-Chlorophenyl)-CH₂—, (CH₃)₃C—CH₂—, Phenyl-O—CH₂—, (4-Methoxyphenyl)-CH₂—, 2-Thienyl-CH₂—CH₂—CH₂—, (2-Thienyl)-, (Indol-3-yl)-CH₂—, Benzo[b]thiophen-3yl)-CH₂—, (3-Thienyl)-CH₂—, Phenyl-CH(NH₂)—, Phenyl-CH(NHCO—O-Benzyl)-, (2-Nitrophenyl)-CH₂—, Phenyl-(CH₂)₄—, (2-Furyl)-, Cyclohexyl-CH₂—CH₂—, (2-Bromophenyl)-CH₂—, Phenyl-SO₂—CH₂—CH₂—, (4-Hydroxyphenyl)-CH₂—, Phenyl-CH₂—NH—, N-Cyclohexyl-NH—, N-(2,6-Difluorophenyl)-NH—, N-Isopropyl-NH—, N-Cyclohexyl-NH—, Methoxy-CH₂—CH₂—, 2-Methoxy-phenyl-, Phenoxy-CH₂—CH₂—, Cyclohexyl-CH₂—, 4-Fluorophenyl-, Phenyl-CH₂—, Cyclopentyl-CH₂—, 4-Methylphenyl-, 3,4-Dimethoxyphenyl-, 2,5-Dimethoxyphenyl-, 2,3,4,5,6-Pentamethylphenyl-, 3-Fluoro-2,4-dimethylphenyl-, 4-Fluoro-3,5-dimethylphenyl-, 2,4,5-Trichlorophenyl-, 4-tert. Butylphenyl-, 2,3-Dichlorophenyl-, (3-Thienyl)-CH—(CH₃)—, (2-Thienyl)-CH—(CH₃)—, 4-Chlorophenyl-, 4-Trifluoromethyl-phenyl-, 4-Methoxyphenyl-, 2-Chlorophenyl-, 2-Fluorophenyl-, (2-Thienyl)-(CH₂)₄—, Phenyl-(CH₂)₄—, (2-Thienyl)-CH₂—CH₂—, (2-Chlorophenyl)-CH₂—, 3,4-Dichlorophenyl-, 2,4-Dichlorophenyl-, 2,5-Dichlorophenyl-, 2,4-Difluorophenyl-, (2-Fluorophenyl)-CH₂—, (2-Furyl)-CH₂—, 2-Chlorophenyl-, 2-Chloro-6-methylphenyl-, (2-Thienyl)-CH₂—, (3-Thienyl)-CH₂—, 4-Acetylaminophenyl-, 3-Trifluoromethyl-phenyl-, 2-Trifluoromethyl-phenyl-, 5-Methyl-2thienyl-, 2-Trifluoromethoxyphenyl, 2-Trifluoromethylphenyl-CH₂, 2-Trifluoromethoxyphenyl-CH₂—, 2-Trifluoromethylthiophenyl-CH₂—, 2-Naphtyl-, 4-Fluoro-3,5-dimethylphenyl-, (5-methyl-2-thienyl)-CH—(CH₃)—;

R(2) is Benzyl, CH₂—CH₂—OH, 4-Methoxy-benzyl, 4-Chloro-benzyl, Phenyl, Cyclohexyl, 2-Methoxy-benzyl, 2-Hydroxy-ethyl, 2-Chloro-benzyl, Isobutyl, 1(S)-Phenylethyl, 4-Methyl-benzyl, 3-Methoxy-benzyl, 3,4-Methylenedioxy-benzyl, 5-Fluor-(2-Methoxy) ethoxy-benzyl, 1(R)-Phenyl-ethyl, 4-Trifluoromethyl-benzyl, 2-(4-Methoxyphenyl)-ethyl, 1(S)-(4-Methylphenyl)-ethyl, 2-Furylmethyl, 1(R)-(4-Methylphenyl)-ethyl, 4-(Dimethylamino)-benzyl, 2-(2-Thienyl)-ethyl, 2-Phenoxyethyl, 2,3-Dichloro-benzyl, Cyclopropylmethyl, 3,4,5-Trimethoxy-benzyl, (4-Pyridyl)-methyl, 4-Fluoro-benzyl,2, 4-Dimethoxy-benzyl, 3-Phenyl-propyl, 2-Methoxy-ethyl, Methyl, Ethyl, (2-Pyridyl)-methyl, Cyclopropyl, (2-Benzimidazolyl)-methyl, 1-Methoxycarbonyl-2-phenyl-ethyl, (3,4-Dihydro-quinazolin-2-yl)-methyl, Propargyl, (2-Thienyl)-methyl, Cyclohexyl-methyl, 3,4-Dichloro-benzyl, Phenyl-CH(COOC(CH₃)3), Phenyl-CH(COOCH₃), 2,4-Dichloro-benzyl, (1-Naphthyl)-methyl, 2-(4-H₂NSO₂—-Phenyl)-ethyl, 3-Chloro-benzyl, 2,3-Dichloro-benzyl, 3-Methyl-benzyl, 2-Methyl-benzyl, (CH₃)2C=CH—CH₂—CH₂—C(CH₃)=CH—CH₂, 1-Indanyl, 1,2,3,4-Tetrahydro-1-naphthyl, 2-Fluoro-benzyl, 3-Fluoro-benzyl, (1,2,3,4-Tetrahydro-2-furyl)-methyl, 2,4-Difluorophenyl, 4-tert.-Butylphenyl, 2,6-Dichlorophenyl, 3-Chloro4-fluorophenyl, 4-Chloro-2,5-dimethyloxyphenyl, 2-Cyanophenyl, 2-Chlorophenyl, 2,3-Dichlorophenyl, 4-Fluorophenyl, 2,3-Dichlorophenyl, 4-(4-Fluorophenoxy)-phenyl, 3-Trifluoromethyl-phenyl, 2-Chloro-4-cyanophenyl, 2-Acetyl-phenyl, (1-Phenylcylopentyl)-methyl, 2-Ethyl-2-(4-Methoxyphenyl)-butyl, [3-(Pyrrolidine-1-carbonyl)-4,5-dihydro-isoxazol-5-yl]-methyl, 4-Acetylamino-2-methylphenyl, 5-Acetylamino-2-methylphenyl, 4-Acetylamino-2,6-dimethylphenyl, 4-Chlorophenyl, 3-Acetylphenyl, 4-Trifluoromethyl-phenyl, 2,5-Difluorophenyl, 4-Isopropylphenyl, 4-Methoxyphenyl, 4-Ethoxyphenyl, 5-Chloro-2-methoxyphenyl, 2-Fluorophenyl, 1-Naphthyl, 2-Trifluoromethyl-phenyl, 2-Ethylphenyl, 2, 4-Dimethylphenyl, 2,4,5-Trimethylphenyl, 2,5-Dimethylphenyl, 3-Chloro-2-methylphenyl, 4-Chloro-2-methylphenyl, 3-Trifluoromethyl-phenyl, 2,6-dimethylphenyl, 2,3-Dimethylphenyl, 4-Ethoxyphenyl, 3,5-Dichlorophenyl, 3,4-Dichlorophenyl, 3,4-Dimethoxyphenyl, 4-Bromophenyl, 2-Chlorophenyl, 2-Methylphenyl, 2-Methoxyphenyl, 2,6-Diethylphenyl, 2,6-Diisopropylphenyl, 2-Biphenylyl, 2-Naphthyl, 4-Methylphenyl, 2,4-Dimethoxyphenyl, 2,5-Dimethylphenyl, 2-Chloro-4-methoxyphenyl, 2-Methoxy-5-methylphenyl, 3-Methoxy-4-methylphenyl, 2-Methoxyphenyl, 3-Hydroxyphenyl, 2-Chloro-5-trifluoromethyl-phenyl, 1-Acetylamino-2-naphthyl, 4-Ethylphenyl, 2,5-Dichlorophenyl, 4-Trifluoromethoxyphenyl, 2 Chlorophenyl, 2-Methyl-1-naphthyl-, 1,3-Dihydro-1-oxo-benzo[c]furan-6-yl, Neopentyl, Isopropyl, 3-Nitro-benzyl, 2-Ethoxy-benzyl, 2,2,2-Trifluoroethyl, 2-(3-Trifluoromethyl-phenyl)ethyl, 1-Indanyl, 2-Phenyl-ethyl, (2-Naphthyl)-methyl, 2-Phenylethyl, Phenyl-CH(COOH)—, 3-Phenyl-benzyl-, 4-(4-Chlorophenoxy)-phenyl, 5-Chloro-2-methylphenyl-, 2-Fluorophenyl, 1-Naphthyl-;

R(3) is hydrogen;
R(4) hydrogen;
R(5) hydrogen, Chloro, —SO₂CH₃, (2-Methoxy)ethoxy-;
R(6) hydrogen;
R(7) hydrogen, Methyl-, Chloro; and
X is —CO—, —CO—CO—, —CO—NH—, —SO₂—.

27. A compound as claimed in claim 5, in which:
R(1) is CH₃—CH₂—CH₂—, Cyclohexyl-CH₂-CH₂—, Cyclohexyl-, 3-Methoxy-phenyl-CH₂—, 2-Methylphenyl-CH₂—, 2-Methylphenyl, 2-Thienyl-CH₂—, 4-t-Butyl-phenyl-, 2-Fluorophenyl-, Allyl-O—, 3,4,5-Trimethoxy-phenyl-, 2-Chloro-phenyl-, Phenyl-, CH₃—, E—CH₃—CH=CH—, CH₃—(CH₂)₃, Phenyl-CH₂—CH₂—, 4-Methyl-phenyl-, Benzo[b]thiophen-2-yl-, Thien-2-yl-, (Phenyl)CH₂—, Phenyl-CH₂—CO—CH(Phenyl)-, (4-Chlorophenyl)-CH₂—, (CH₃)₃C—CH₂—, Phenyl-O—CH₂—, (4-Methoxyphenyl)-CH₂—, 2-Thienyl-CH₂—CH₂—CH₂—, (2-Thienyl)-, (Indol-3-yl)-CH₂—, Benzo[b]thiophen-3-yl)-CH₂—, (3-Thienyl)-CH₂—, Phenyl-CH(NH₂)—, Phenyl-CH(NHCO—O-Benzyl)-, (2-Nitrophenyl)-CH₂—, Phenyl-(CH₂)₄—, (2-Furyl)-, Cyclohexyl-CH₂—CH₂—, (2-Bromophenyl)-CH₂—, Phenyl-SO₂—CH₂—CH₂—, (4-Hydroxyphenyl)-CH₂—, Phenyl-CH₂—NH—, N-Cyclohexyl-NH—, N-(2,6-Difluorophenyl)-NH—, N-Isopropyl-NH—, N-Cyclohexyl-NH—, Methoxy-CH₂—CH₂—, 2-Methoxy-phenyl-, Phenoxy-CH₂—CH₂—, Cyclohexyl-CH₂—, 4-Fluorophenyl-, Phenyl-CH₂—, Cyclopentyl-CH₂—, 4-Methylphenyl-, 3,4-Dimethoxyphenyl-, 2,5-Dimethoxyphenyl-, 2,3,4,5,6-Pentamethylphenyl-, 3-Fluoro-2,4-dimethylphenyl-, 4-Fluoro-3,5-dimethylphenyl-, 2,4,5-Trichlorophenyl-, 4-tert. Butylphenyl-, 2,3-Dichlorophenyl-, (3-Thienyl)-CH—(CH₃)—, (2-Thienyl)-CH—(CH₃)—, 4-Chlorophenyl-, 4-Trifluoromethyl-phenyl-, 4-Methoxyphenyl-, 2-Chlorophenyl-, 2-Fluorophenyl-, (2-Thienyl)-$(CH_2)_4$—, Phenyl-$(CH_2)_4$—, (2-Thienyl)-$CH_2$—$CH_2$—, (2-Chlorophenyl)-$CH_2$—, 3,4-Dichlorophenyl-, 2,4-Dichlorophenyl-, 2,5-Dichlorophenyl-, 2,4-Difluorophenyl-, (2-Fluorophenyl)-$CH_2$—, (2-Furyl)-$CH_2$—, 2-Chlorophenyl-, 2-Chloro-6-methylphenyl-, (2-Thienyl)-$CH_2$—, (3-Thienyl)-$CH_2$—, 4-Acetylaminophenyl-, 3-Trifluoromethyl-phenyl-, 2-Trifluoromethyl-phenyl-, 5-Methyl-2thienyl-, 2-Trifluoromethoxyphenyl, 2-Trifluoromethylphenyl-$CH_2$, 2-Trifluoromethoxyphenyl-$CH_2$—, 2-Trifluoromethylthiophenyl-$CH_2$—, 2-Naphtyl-, 4-Fluoro-3,5-dimethylphenyl-, (5-methyl-2-thienyl)-CH—$(CH_3)$—;

R(2) is Benzyl, $CH_2$—$CH_2$—OH, 4-Methoxy-benzyl, 4-Chloro-benzyl, Phenyl, Cyclohexyl, 2-Methoxy-benzyl, 2-Hydroxy-ethyl, 2-Chloro-benzyl, Isobutyl, 1(S)-Phenylethyl, 4-Methyl-benzyl, 3-Methoxy-benzyl, 3,4-Methylenedioxy-benzyl, 5-Fluor-(2-Methoxy) ethoxy-benzyl, 1(R)-Phenyl-ethyl, 4-Trifluoromethyl-benzyl, 2-(4-Methoxyphenyl)-ethyl, 1(S)-(4-Methylphenyl)-ethyl, 2-Furylmethyl, 1(R)-(4-Methylphenyl)-ethyl, 4-(Dimethylamino)-benzyl, 2-(2-Thienyl)-ethyl, 2-Phenoxyethyl, 2,3-Dichloro-benzyl, Cyclopropylmethyl, 3,4,5-Trimethoxy-benzyl, (4-Pyridyl)-methyl, 4-Fluoro-benzyl, 2,4-Dimethoxy-benzyl, 3-Phenyl-propyl, 2-Methoxy-ethyl, Methyl, Ethyl, (2-Pyridyl)-methyl, Cyclopropyl, (2-Benzimidazolyl)-methyl, 1-Methoxycarbonyl-2-phenyl-ethyl, (3,4-Dihydro-quinazolin-2-yl)-methyl, Propargyl, (2-Thienyl)-methyl, Cyclohexyl-methyl, 3,4-Dichloro-benzyl, Phenyl-CH(COOC$(CH_3)$3), Phenyl-CH(COOCH$_3$), 2,4-Dichloro-benzyl, (1-Naphthyl)-methyl, 2-(4-$H_2NSO_2$— Phenyl)-ethyl, 3-Chloro-benzyl, 2,3-Dichloro-benzyl, 3-Methyl-benzyl, 2-Methyl-benzyl, $(CH_3)2C$=CH—$CH_2$—$CH_2$—C$(CH_3)$=CH—$CH_2$, 1-Indanyl, 1,2,3,4-Tetrahydro-1-naphthyl, 2-Fluoro-benzyl, 3-Fluoro-benzyl, (1,2,3,4-Tetrahydro-2-furyl)-methyl, 2,4-Difluorophenyl, 4-tert.-Butylphenyl, 2,6-Dichlorophenyl, 3-Chloro-4-fluorophenyl, 4-Chloro-2,5-dimethyloxyphenyl, 2-Cyanophenyl, 2-Chlorophenyl, 2,3-Dichlorophenyl, 4-Fluorophenyl, 2,3-Dichlorophenyl, 4-(4-Fluorophenoxy)-phenyl, 3-Trifluoromethyl-phenyl, 2-Chloro-4-cyanophenyl, 2-Acetyl-phenyl, (1-Phenylcylopentyl)-methyl, 2-Ethyl-2-(4-Methoxyphenyl)-butyl, [3-(Pyrrolidine-1-carbonyl)-4,5-dihydro-isoxazol-5-yl]-methyl, 4-Acetylamino-2-methylphenyl, 5-Acetylamino-2-methylphenyl, 4-Acetylamino-2,6-dimethylphenyl, 4-Chlorophenyl, 3-Acetylphenyl, 4-Trifluoromethyl-phenyl, 2,5-Difluorophenyl, 4-Isopropylphenyl, 4-Methoxyphenyl, 4-Ethoxyphenyl, 5-Chloro-2-methoxyphenyl, 2-Fluorophenyl, 1-Naphthyl, 2-Trifluoromethyl-phenyl, 2-Ethylphenyl, 2,4-Dimethylphenyl, 2,4,5-Trimethylphenyl, 2,5-Dimethylphenyl, 3-Chloro-2-methylphenyl, 4-Chloro-2-methylphenyl, 3-Trifluoromethyl-phenyl, 2,6-dimethylphenyl, 2,3-Dimethylphenyl, 4-Ethoxyphenyl, 3,5-Dichlorophenyl, 3,4-Dichlorophenyl, 3,4-Dimethoxyphenyl, 4-Bromophenyl, 2-Chlorophenyl, 2-Methylphenyl, 2-Methoxyphenyl, 2,6-Diethylphenyl, 2,6-Diisopropylphenyl, 2-Biphenylyl, 2-Naphthyl, 4-Methylphenyl, 2,4-Dimethoxyphenyl, 2,5-Dimethylphenyl, 2-Chloro-4-methoxyphenyl, 2-Methoxy-5-methylphenyl, 3-Methoxy-4-methylphenyl, 2-Methoxyphenyl, 3-Hydroxyphenyl, 2-Chloro-5-trifluoromethyl-phenyl, 1-Acetylamino-2-naphthyl, 4-Ethylphenyl, 2,5-Dichlorophenyl, 4-Trifluoromethoxyphenyl, 2 Chlorophenyl, 2-Methyl-1-naphthyl-, 1,3-Dihydro-1-oxo-benzo[c]furan-6-yl, Neopentyl, Isopropyl, 3-Nitro-benzyl, 2-Ethoxy-benzyl, 2,2,2-Trifluoroethyl, 2-(3-Trifluoromethyl-phenyl)ethyl, 1-Indanyl, 2-Phenyl-ethyl, (2-Naphthyl)-methyl, 2-Phenylethyl, Phenyl-CH(COOH)—, 3-Phenyl-benzyl-, 4-(4-Chlorophenoxy)-phenyl, 5-Chloro-2-methylphenyl-, 2-Fluorophenyl, 1-Naphthyl-;

R(3) is hydrogen;
R(4) hydrogen;
R(5) hydrogen, Chloro, —$SO_2CH_3$, (2-Methoxy)ethoxy-;
R(6) hydrogen;
R(7) hydrogen, Methyl-, Chloro; and
X is —CO—, —CO—CO—, —CO—NH—, —$SO_2$—.

28. A compound as claimed in claim 5, wherein
R(1) is 2-Chlorophenyl;
R(2) is 4-Methylbenzyl;
R(3)–R(7) is hydrogen; and
X is —CO—.

29. A compound as claimed in claim 1, which is 4'-{[Benzyl-thiophen-2-sulfonyl)amino]-methyl}-3'-chlor-biphenyl-2-sulfonylcyanamid, or a physiologically tolerable salt thereof.

\* \* \* \* \*